US009005621B2

(12) United States Patent
Vogels et al.

(10) Patent No.: US 9,005,621 B2
(45) Date of Patent: Apr. 14, 2015

(54) HUMAN BINDING MOLECULES CAPABLE OF BINDING TO AND NEUTRALIZING INFLUENZA B VIRUSES AND USES THEREOF

(71) Applicant: Crucell Holland B.V., Leiden (NL)

(72) Inventors: Ronald Vogels, Linschoten (NL); Theodorus H. J. Kwaks, Voorschoten (NL)

(73) Assignee: Crucell Holland B.V., Leiden (NL)

( * ) Notice: Subject to any disclaimer, the term of this patent is extended or adjusted under 35 U.S.C. 154(b) by 63 days.

(21) Appl. No.: 14/323,908

(22) Filed: Jul. 3, 2014

(65) Prior Publication Data

US 2014/0341929 A1 Nov. 20, 2014

Related U.S. Application Data

(63) Continuation of application No. 14/051,365, filed on Oct. 10, 2013, which is a continuation of application No. 13/789,284, filed on Mar. 7, 2013, now Pat. No. 8,834,881.

(60) Provisional application No. 61/608,414, filed on Mar. 8, 2012.

(30) Foreign Application Priority Data

Mar. 8, 2012 (EP) .................................... 12158525

(51) Int. Cl.
| | | |
|---|---|---|
| A61K 49/00 | (2006.01) | |
| A61K 39/395 | (2006.01) | |
| A61K 39/42 | (2006.01) | |
| A61K 39/38 | (2006.01) | |
| A61K 39/145 | (2006.01) | |
| C12Q 1/70 | (2006.01) | |
| C07K 16/10 | (2006.01) | |
| A61K 47/48 | (2006.01) | |
| G01N 33/569 | (2006.01) | |

(52) U.S. Cl.
CPC ............. *C07K 16/1018* (2013.01); *A61K 39/42* (2013.01); *A61K 47/4853* (2013.01); *G01N 33/56983* (2013.01)

(58) Field of Classification Search
CPC .................... G01N 2333/11; G01N 33/56983; G01N 33/558; G01N 2469/10; G01N 2469/20; G01N 33/53; C07K 14/005; C07K 16/1018; C07K 2319/00; C07K 14/11; C07K 2316/96; C07K 2317/34; C07K 2317/56
See application file for complete search history.

(56) References Cited

U.S. PATENT DOCUMENTS

| | | |
|---|---|---|
| 2003/0157109 A1 | 8/2003 | Corvalan et al. |
| 2006/0286112 A1 | 12/2006 | Kellermann et al. |
| 2006/0293506 A1 | 12/2006 | Corvalan et al. |
| 2010/0096364 A1 | 4/2010 | Balemi et al. |
| 2010/0330103 A1 | 12/2010 | Rinkenberger et al. |
| 2011/0076284 A1 | 3/2011 | Corbin et al. |
| 2012/0039898 A1 | 2/2012 | Throsby et al. |
| 2012/0134994 A1 | 5/2012 | Kim et al. |
| 2013/0243792 A1 | 9/2013 | Vogels et al. |
| 2014/0065165 A1 | 3/2014 | Vogels et al. |

FOREIGN PATENT DOCUMENTS

| | | |
|---|---|---|
| WO | 8403564 A1 | 9/1984 |
| WO | 9309872 A1 | 5/1993 |
| WO | 0063403 A2 | 10/2000 |
| WO | 02103012 A1 | 12/2002 |
| WO | 03057857 A2 | 7/2003 |
| WO | 2006124269 A2 | 11/2006 |
| WO | 2008028946 A2 | 3/2008 |
| WO | 2008112004 A2 | 9/2008 |
| WO | 2009002380 A2 | 12/2008 |
| WO | 2010054265 A2 | 5/2010 |
| WO | 2010130636 A1 | 11/2010 |
| WO | 2011038302 A1 | 3/2011 |

OTHER PUBLICATIONS

Nakagawa et al., Rapid detection and identification of two lineages of influenza B strains with monoclonal antibodies, 1999, Journal of Virological Methods, vol. 79, pp. 113-120.
Dreyfus et al., Highly Conserved Protective Epitopes on Influenza B Viruses, Science, Sep. 14, 2012, pp. 1343-1348, vol. 337.
Ekiert et al., Antibody Recognition of a Highly Conserved Influenza Virus Epitope, Science, Apr. 10, 2009, pp. 246-251, vol. 324.
Ekiert et al., A Highly Conserved Neutralizing Epitope on Group 2 Influenza A Viruses, Science, Aug. 12, 2011, pp. 843-850, vol. 333.
Whittle et al., Broadly Neutralizing Human Antibody that Recognizes the Receptor-Binding Pocket of Influenza Virus Hemagglutinin, PNAS, Aug. 23, 2011, pp. 14216-14221, vol. 108, No. 34.
Krause et al., A Broadly Neutralizing Human Monoclonal Antibody That Recognizes a Conserved, Novel Epitope on the Globular Head of the Influenza H1N1 Virus Hemagglutinin, Journal of Virology, Oct. 2011, pp. 10905-10908, vol. 85, No. 20.
Throsby et al., Heterosubtypic Neutralizing Monoclonal Antibodies Cross-Protective Against H5N1 and H1N1 Recovered from Human IgM+ Memory B Cells, PLOS ONE, Dec. 2008, e3942 (15 pages); vol. 3, No. 12.

(Continued)

*Primary Examiner* — Benjamin P Blumel
(74) *Attorney, Agent, or Firm* — TraskBritt, P.C.

(57) ABSTRACT

Described are binding molecules, such as human monoclonal antibodies, that bind to hemagglutinin of influenza B viruses, and have a broad neutralizing activity against such influenza viruses. These binding molecules do not bind to hemagglutinin of influenza A viruses. Further provided are nucleic acid molecules encoding the binding molecules, and compositions comprising the binding molecules. The binding molecules can be used in the diagnosis of, prophylaxis against, and/or treatment of influenza B virus infections.

16 Claims, 5 Drawing Sheets

(56) References Cited

OTHER PUBLICATIONS

Brochet et al., IMGT/V-Quest; The Highly Customized and Integrated System for IG and TR Standardized V-J and V D-J Sequence Analysis, Nucleic Acids Research, 2008, W503-08, vol. 36.

De Kruif et al., Rapid Selection of Cell Subpopulation-Specific Human Monoclonal Antibodies form a Synthetic Phage Antibody Library, Proc. Natl. Acad. Sci, Apr. 1995, pp. 3938-3942, vol. 92, USA.

Kanegae et al., Evolutionary Pattern of the Hemagglutinin Gene of Influenza B Viruses Isolated in Japan: Cocirculating Lineages in the Same Epidemic Season, Journal of Virology, Jun. 1990, pp. 2860-2865, vol. 65, No. 6.

Kubota-Koketsu et al., Broad neutralizing Human Monoclonal Antibodies Against Influenza Virus From Vaccinated Healthy Donors, Biochemical and Biophysical Research Communications, 2009, pp. 180-85, vol. 387.

Rota et al., Antigenic and Genetic Characterization of the Haemagglutinins of Recent Cocirculating Strains of Influenza B Virus, Journal of General Virology, 1992, pp. 2737-2742, vol. 73.

Thompson et al., Mortality Associated With Influenza and Respiratory Syncytial Virus in the United States, JAMA, Jan. 8, 2003, pp. 179-186, vol. 289.

Thompson et al., Influenza-Associated Hospitalizations in the United States, JAMA, Sep. 15, 2004, pp. 1333-1340, vol. 292, No. 11.

Wrammert et al., Rapid Cloning of High-Affinity Human Monoclonal Antibodies Against Influenza Virus, May 29, 2008, pp. 667-672, vol. 453.

European Search Report for EP 12 15 8525 dated Mar. 7, 2013.

A.

B.

Scale bars represent 1 μm

HUMAN BINDING MOLECULES CAPABLE OF BINDING TO AND NEUTRALIZING INFLUENZA B VIRUSES AND USES THEREOF

CROSS-REFERENCE TO RELATED APPLICATIONS

This application is a continuation of co-pending U.S. patent application Ser. No. 14/051,365, filed Oct. 10, 2013, now U.S. Pat. No. 8,852,595, issued Oct. 7, 2014, which is a continuation of co-pending U.S. patent application Ser. No. 13/789,284, filed Mar. 7, 2013, now U.S. Pat. No. 8,834,881, issued Sep. 16, 2014, which application claims the benefit under 35 U.S.C. §119(e) of U.S. Provisional Patent Application Ser. No. 61/608,414, filed Mar. 8, 2012, and benefit under the Paris Convention to EP 12158525.1 filed Mar. 8, 2012, the contents of the entirety of each of which are incorporated herein by this reference.

STATEMENT ACCORDING TO 37 C.F.R. §1.821(c) or (e)—SEQUENCE LISTING SUBMITTED AS PDF FILE WITH A REQUEST TO TRANSFER CRF FROM PARENT APPLICATION

Pursuant to 37 C.F.R. §1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

The application relates to biotechnology and medicine generally, in particular to binding molecules, e.g., human monoclonal antibodies or antigen-binding fragments thereof, capable of binding to and neutralizing influenza B viruses, in particular neutralizing binding molecules binding to and neutralizing influenza B viruses from both the B/Yamagata and/or B/Victoria lineage. In addition, the invention relates to the diagnosis, prophylaxis and/or treatment of infections caused by an influenza B virus, in particular of infections caused by influenza B viruses from the B/Yamagata and B/Victoria lineages.

BACKGROUND

Influenza infection (also referred to as "influenza" or "the flu") is one of the most common diseases known to man causing between three and five million cases of severe illness and between 250,000 and 500,000 deaths every year around the world. Influenza rapidly spreads in seasonal epidemics affecting 5 to 15% of the population and the burden on health care costs and lost productivity are extensive (World Healthcare Organization (WHO)). There are three types of influenza flu virus (types A, B and C) responsible for infectious pathologies in humans and animals. Currently, the type A and type B viruses are the agents responsible for the influenza epidemics and pandemics observed in humans.

Current approaches to dealing with annual influenza epidemics include annual vaccination, preferably generating heterotypic cross-protection. However, circulating influenza viruses in humans are subject to permanent antigenic changes which require annual adaptation of the influenza vaccine formulation to ensure the closest possible match between the influenza vaccine strains and the circulating influenza strains. Alternatively, antiviral drugs, such as oseltamivir (TAMIFLU®) can be effective for prevention and treatment of influenza infection. The number of influenza virus strains showing resistance against antiviral drugs such as oseltamivir is, however, increasing.

An alternative approach is the development of antibody-based prophylactic or therapeutic means to neutralize various seasonal influenza viruses.

Broadly cross-neutralizing antibodies recognizing epitopes in the conserved stem-region of HA of influenza A viruses of phylogenetic group 1 (such as influenza viruses comprising HA of the H1 or H5 subtype) have recently been disclosed (e.g., CR6261, see WO2008/028946), as well as cross-neutralizing antibodies recognizing a highly conserved epitope in the stem-region of HA of influenza A viruses of phylogenetic group 2, such as influenza viruses comprising HA of the H3 and/or H7 subtypes (e.g., CR8020, CR8043; see WO 2010/130636). More recently, antibodies capable of binding to and neutralizing influenza A viruses of both phylogenetic group 1 and group 2, as well as influenza B viruses were discovered (e.g., CR9114, described in application no. EP11173953.8).

To date, less attention has been paid to influenza B viruses. This may be due to the fact that—primarily being restricted to humans as host—influenza B viruses lack the large animal reservoirs that key to the emergence of pandemic influenza A strains. However, the cumulative impact of annual epidemics during interpandemic periods exceeds that of pandemics and although the morbidity and mortality rates attributable to influenza B are lower than those of e.g., H3N2 viruses, they are higher than those of H1N1 viruses (Thompson (2003), Thompson (2004)).

The evolution of influenza B viruses is characterized by co-circulation of antigenically and genetically distinct lineages for extended periods of time. Two lineages, represented by the prototype viruses B/Victoria/2/87 (Victoria lineage) and B/Yamagata/16/88 (Yamagata lineage), are currently distinguished (Kanegae (1990), Rota (1990)). B/Yamagata was the major lineage circulating until the 1980s, when B/Victoria lineage viruses appeared. Since then, drift variants of both influenza B lineages have been co-circulating globally, with both lineages concurrently circulating in recent influenza seasons.

SUMMARY OF THE DISCLOSURE

Since influenza B viruses are the major cause of seasonal influenza epidemics every two to four years, and in view of the severity of the respiratory illness caused by certain influenza B viruses, as well has the high economic impact of the seasonal epidemics, an ongoing need exists for alternative and effective means for preventing and treating influenza B subtypes.

Provided are binding molecules, in particular human binding molecules, able to specifically bind to and neutralizing influenza B virus strains from both the B/Yamagata and B/Victoria lineages. The binding molecules do not bind to influenza A virus subtypes.

Also provided are immunoconjugates and/or pharmaceutical compositions comprising the binding molecules, as well as nucleic acid molecules ("polynucleotides") encoding at least the binding region of the human binding molecules.

The binding molecules, immunoconjugates and/or nucleic acid molecules hereof are suitable for use as a universal prophylactic, diagnostic, and/or treatment agent for influenza B viruses, irrespective of the causative influenza B virus subtype.

DETAILED DESCRIPTION

Figure 1:
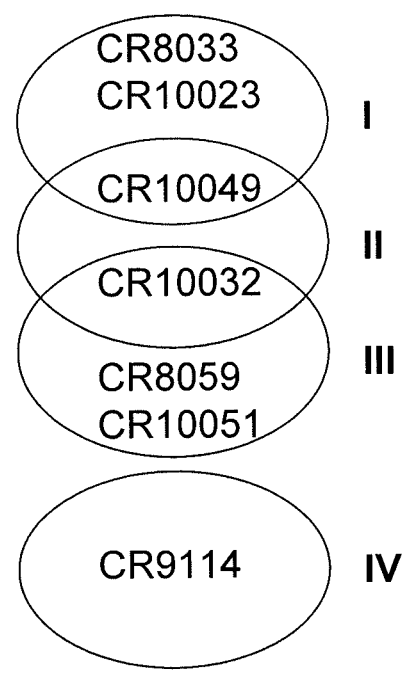
FIG. 1 is a schematic epitope map based upon competition experiments. Anti-influenza B antibodies identified herein cluster into 4 groups based upon binding/competition to influenza B HA.

Definitions of terms as used in the instant disclosure are given below.

The term "included" or "including" is deemed to be followed by the words "without limitation."

The term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g., HA. Regardless of structure, the antigen-binding fragment binds with the same antigen that is recognized by the intact immunoglobulin. An antigen-binding fragment can comprise a peptide or polypeptide comprising a peptide of at least 2, 5, 10, 15, 20, 25, 30, 35, 40, 50, 60, 70, 80, 90, 100, 125, 150, 175, 200, or 250 contiguous amino acid residues of the peptide of the binding molecule.

The term "binding molecule," includes all immunoglobulin classes and subclasses known in the art. Depending on the peptide of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule but can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is therefore applied in definition to the naked or unconjugated binding molecule in vitro, not in vivo.

As used herein, the term "biological sample" encompasses a variety of sample types, including blood and other liquid samples of biological origin, solid tissue samples such as a biopsy specimen or tissue cultures, or cells derived there from and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

The term "complementarity determining regions" (CDR) as used herein means sequences within the variable regions of binding molecules, such as immunoglobulins, that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of posttranslational modifications of proteins.

The term "deletion" denotes a change in either amino acid or polynucleotide in which one or more amino acid or nucleotide residues, respectively, are absent as compared to the reference, often the naturally occurring, molecule.

The term "expression-regulating polynucleotide" refers to polynucleotides necessary for and/or affecting the expression of an operably linked coding sequence in a particular host organism. The expression-regulating polynucleotides, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any polynucleotide showing activity in the host organism of choice and can be derived from genes encoding proteins, which are either homologous or heterologous to the host organism. The identification and employment of expression-regulating sequences is routine to the person skilled in the art.

The term "functional variant" refers to a nucleic acid molecule or binding molecule that comprises a nucleotide and/or peptide that is altered by one or more nucleotides and/or amino acids compared to the nucleotide and/or peptides of the reference nucleic acid molecule or binding molecule. A functional variant of a binding molecule hereof is capable of competing for binding to the binding partner, i.e., the influenza virus, with the reference binding molecule. In other words, the modifications in the amino acid and/or polynucleotide of the reference binding molecule do not significantly affect or alter the binding characteristics of the binding molecule encoded by the polynucleotide or containing the peptide, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), non-polar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that also other classifications of amino acid residue families than the one used above can be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs known in the art.

A mutation in a polynucleotide can be a single alteration made at a locus (a point mutation), such as transition or transversion mutations, or alternatively, multiple nucleotides may be inserted, deleted or changed at a single locus. In addition, one or more alterations may be made at any number of loci within a polynucleotide. The mutations may be performed by any suitable method known in the art.

The term "influenza virus subtype" in relation to influenza A viruses refers to influenza A virus variants that are characterized by various combinations of the hemagglutinin (H) and neuramidase (N) viral surface proteins. Influenza A virus subtypes may be referred to by their H number, such as for example "influenza virus comprising HA of the H1 or H3 subtype," or "H1 influenza virus" "H3 influenza virus," or by a combination of an H number and an N number, such as for example "influenza virus subtype H3N2" or "H3N2." The term influenza virus "subtype" specifically includes all individual influenza virus "strains" within each subtype, which usually result from mutations and show different pathogenic profiles. Such strains may also be referred to as various "isolates" of a viral subtype. Accordingly, as used herein, the terms "strains" and "isolates" may be used interchangeably.

The term "neutralizing" as used herein in relation to the binding molecule hereof refers to a binding molecule that inhibits an influenza virus from replication, in vitro and/or within a subject, regardless of the mechanism by which neutralization is achieved. Thus, neutralization can e.g., be achieved by inhibiting the attachment or adhesion of the virus to the cell surface, or by inhibition of the fusion of viral and cellular membranes following attachment of the virus to the target cell, or by inhibiting viral egress from infected cells, and the like.

The term "cross-neutralizing" or "cross-neutralization" as used herein in relation to the binding molecules hereof refers to the ability of the binding molecules hereof to neutralize influenza B viruses from both the B/Yamagata and the B/Victoria lineage, and/or different influenza B virus strains within these lineages.

The term "host" is intended to refer to an organism or a cell into which a vector such as a cloning vector or an expression vector has been introduced. The organism or cell can be prokaryotic or eukaryotic. Preferably, the hosts isolated host cells, e.g., host cells in culture. The term "host cells" merely signifies that the cells are modified for the (over)-expression of the binding molecule hereof and include B-cells that originally express these binding molecule and which cells have been modified to over-express the binding molecule by immortalization, amplification, enhancement of expression etc. It should be understood that the term host is intended to refer not only to the particular subject organism or cell but to the progeny of such an organism or cell as well. Because certain modifications may occur in succeeding generations due to either mutation or environmental influences, such progeny may not, in fact, be identical to the parent organism or cell, but are still included within the scope of the term "host."

The term "human," when applied to binding molecules as defined herein, refers to molecules that are either directly derived from a human or based upon a human germ line sequence. When a binding molecule is derived from or based upon a human sequence and subsequently modified, it is still to be considered human as used throughout the specification. In other words, the teem human, when applied to binding molecules is intended to include binding molecules having variable and constant regions derived from human germline immunoglobulin sequences or based upon variable or constant regions occurring in a human or human lymphocyte and modified in some form. Thus, the human binding molecules may include amino acid residues not encoded by human germline immunoglobulin sequences; comprise substitutions and/or deletions (e.g., mutations introduced by for instance random or site-specific mutagenesis in vitro or by somatic mutation in vivo). "Based upon" as used herein refers to the situation that a polynucleotide may be exactly copied from a template, or with minor mutations, such as by error-prone PCR methods, or synthetically made matching the template exactly or with minor modifications.

The term "insertion," also known as the term "addition," denotes a change in an amino acid or polynucleotide resulting in the addition of one or more amino acid or nucleotide residues, respectively, as compared to the parent sequence.

The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium components, and when the binding molecules are produced by chemical synthesis, they are preferably substantially free of chemical precursors or other chemicals, i.e., they are separated from chemical precursors or other chemicals which are involved in the synthesis of the protein. The term "isolated" when applied to nucleic acid molecules encoding binding molecules as defined herein, is intended to refer to nucleic acid molecules in which the polynucleotides encoding the binding molecules are free of other polynucleotides, particularly polynucleotides encoding binding molecules that bind other binding partners. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as cDNA molecules, can be substantially free of other cellular material or culture medium when produced by recombinant techniques, or substantially free of chemical precursors or other chemicals when chemically synthesized.

The term "monoclonal antibody" refers to a preparation of antibody molecules of single specificity. A monoclonal antibody displays a single binding specificity and affinity for a particular epitope. Accordingly, the term "human monoclonal antibody" refers to an antibody displaying a single binding specificity that has variable and constant regions derived from or based upon human germline immunoglobulin sequences or derived from completely synthetic sequences. The method of preparing the monoclonal antibody is not relevant for the binding specificity.

The term "naturally occurring" as applied to an object refers to the fact that an object or compound can be found in nature. For example, a polypeptide or polynucleotide that is present in an organism that can be isolated from a source in nature and which has not been intentionally modified by man in the laboratory is naturally occurring.

The term "nucleic acid molecule" refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a polynucleotide encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

The term "operably linked" refers to two or more polynucleotide elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the used dosages and concentrations, and is compatible with other ingredients of the formulation comprising the drug, agent or binding molecule. Pharmaceutically acceptable excipients are widely applied and known in the art.

The term "specifically binding" in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In other words, the term "specifically binding" means immunospecifically binding to an antigenic determinant or epitope and not immunospecifically binding to other antigenic determinants or epitopes. A binding molecule that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Binding molecules or fragments thereof that immunospecifically bind to an antigen may be cross-reactive with related antigens, carrying the same epitope. Preferably, binding molecules or fragments thereof that immunospecifically bind to an antigen do not cross-react with other antigens.

A "substitution" denotes the replacement of one or more amino acids or nucleotides by different amino acids or nucleotides, respectively.

The term "therapeutically effective amount" refers to an amount of the binding molecule as defined herein that is effective for preventing, ameliorating and/or treating a condition resulting from infection with an influenza B virus. Amelioration as used in herein may refer to the reduction of visible or perceptible disease symptoms, viremia, or any other measurable manifestation of influenza infection.

The term "treatment" refers to therapeutic treatment as well as prophylactic or preventative measures to cure or halt or at least retard disease progress. Those in need of treatment include those already inflicted with a condition resulting from infection with influenza virus as well as those in which infection with influenza virus is to be prevented. Subjects partially or totally recovered from infection with influenza virus might also be in need of treatment. Prevention encompasses inhibiting or reducing the spread of influenza virus or inhibiting or reducing the onset, development or progression of one or more of the symptoms associated with infection with influenza virus.

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

In one aspect, provided are binding molecules able to specifically bind to hemagglutinin (HA) of influenza B virus strains of the B/Yamagata and B/Victoria lineage, and able to neutralize the influenza B virus strains of the B/Yamagata and/or B/Victoria lineage. These binding molecules do not bind to HA of influenza A viruses. The binding molecules are able to neutralize influenza B viruses both in vitro and in vivo.

The binding molecules may be human antibodies or antigen-binding fragments thereof.

In certain embodiments, the binding molecules bind to a different epitope as compared to the epitope of CR9114 (as described in the co-pending application EP11173953.8), comprising a heavy chain variable region comprising the peptide of SEQ ID NO:116, and a light chain variable region comprising the peptide of SEQ ID NO:117. CR9114 has been shown to be capable of binding to and in vivo neutralizing influenza A viruses of both phylogenetic group 1 and 2, as well as influenza B viruses.

In certain embodiments, the binding molecules bind to the head region of the HA protein of influenza B viruses, in particular to the head region of HA1 of influenza B viruses.

In certain embodiments, the binding molecules block the cellular receptor binding of influenza B viruses of the B/Yamagata lineage and/or the B/Victoria lineage.

In certain embodiments, the binding molecules do not block the cellular receptor binding of influenza viruses of the B/Yamagata lineage and/or the B/Victoria lineage.

In certain embodiments, the binding molecules block egress of influenza B viruses, in particular of influenza virus strains of both the B/Victoria and the B/Yamagata lineage, from infected cells.

In certain embodiments, the isolated binding molecules are able to specifically bind to the hemagglutinin protein (HA) of an influenza B virus and able to neutralize influenza B virus strains of both the B/Victoria/2/87 lineage and the B/Yamagata/16/88 lineage, wherein the binding molecules do not bind to the HA protein of influenza A virus subtypes, and comprise a heavy chain variable region comprising the peptide of SEQ ID NO:71 or a peptide having at least or at least about 80%, 90%, 91%, 92%, 93%, 94%, 95%, 96%, 97%, 98%, 99% or more sequence identity thereto.

In certain embodiments, the binding molecules comprise a light chain variable region comprising the peptide of SEQ ID NO:73, or a peptide (i.e., a "peptide") having at least or at least about 80%, 90%, 91%, 92%, 93%, 94%, 95%, 96%, 97%, 98%, 99% or more sequence identity thereto.

In one embodiment, the binding molecule comprises a heavy chain variable region comprising the peptide of SEQ ID NO:71 and a light chain variable region comprising the peptide of SEQ ID NO:73.

Also provided are binding molecules able to specifically bind to the hemagglutinin protein (HA) of an influenza B virus and able to neutralize influenza B virus strains of both the B/Victoria/2/87 lineage and the B/Yamagata/16/88 lineage, wherein the binding molecules do not bind to the HA protein of influenza A virus subtypes, and wherein the binding molecules comprise a heavy chain CDR1, comprising the peptide of SEQ ID NO:1; a heavy chain CDR2, comprising the peptide of SEQ ID NO:2, and a heavy chain CDR3, comprising the peptide of SEQ ID NO:3. Hereof, CDR regions are according to Kabat et al. (1991) as described in Sequences of Proteins of Immunological Interest.

In certain embodiments, the binding molecules comprise a light chain CDR1, comprising the peptide of SEQ ID NO:4, a light chain CDR2, comprising the peptide of SEQ ID NO:5, and a light chain CDR3, comprising the peptide of SEQ ID NO:6.

In certain embodiments, the binding molecule comprises a heavy chain CDR1 comprising the peptide of SEQ ID NO:1, a heavy chain CDR2 comprising the peptide of SEQ ID NO:2, and a heavy chain CDR3 comprising the peptide of SEQ ID NO:3, and a light chain CDR1 comprising the peptide of SEQ ID NO:4, a light chain CDR2 comprising the peptide of SEQ ID NO:5, and a light chain CDR3 comprising the peptide of SEQ ID NO:6.

Further provided are binding molecules that immunospecifically bind to the same epitope on an influenza B virus HA protein as a binding molecule, comprising a heavy chain variable sequence comprising the peptide of SEQ ID NO:71 and a light chain variable region comprising the peptide of SEQ ID NO:73.

In certain embodiments, the binding molecule comprises a heavy chain CDR1 comprising the peptide of SEQ ID NO:14, a heavy chain CDR2 comprising the peptide of SEQ ID NO:15, and a heavy chain CDR3 comprising the peptide of SEQ ID NO:16, and a light chain CDR1 comprising the peptide of SEQ ID NO:17, a light chain CDR2 comprising the peptide of SEQ ID NO:18, and a light chain CDR3 comprising the peptide of SEQ ID NO:19.

In certain embodiments, the binding molecule comprises a heavy chain CDR1 comprising the peptide of SEQ ID NO:26, a heavy chain CDR2 comprising the peptide of SEQ ID NO:27, and a heavy chain CDR3 comprising the peptide of SEQ ID NO:28, and a light chain CDR1 comprising the peptide of SEQ ID NO:29, a light chain CDR2 comprising the peptide of SEQ ID NO:24, and a light chain CDR3 comprising the peptide of SEQ ID NO:30.

Also provided are binding molecules, able to specifically bind to the hemagglutinin protein (HA) and able to neutralize influenza B virus strains of the B/Victoria lineage, in particular the influenza B virus strain B/Malaysia/2506/2004, when the amino acid on position 168 of HA of the influenza B virus, in particular the influenza B virus strain B/Malaysia/2506/2004, is proline (P), and is unable to neutralize influenza B virus strains of the B/Victoria lineage, in particular B/Malaysia/2506/2004, when the amino acid on position 168 of the HA of the influenza B virus, in particular B/Malaysia/2506/2004, is glutamine (Q).

In certain embodiments, provided are binding molecules, able to specifically bind to the hemagglutinin protein (HA) and able to neutralize influenza B virus strains of the B/Yamagata lineage, in particular the influenza B virus strain B/Florida/04/2006, when the amino acid on position 38 of HA of the influenza B virus, in particular the influenza B virus strain B/Florida/04/200, is lysine (K), and is also able to neutralize influenza B virus strains of the B/Yamagata lineage, in particular B/Florida/04/2006, when the amino acid on position 38 of HA of the influenza B virus, in particular B/Florida/04/2006, is glutamic acid (E).

Further provided are binding molecules able to specifically bind to the hemagglutinin protein (HA) of an influenza B virus and able to neutralize influenza B virus strains of both the B/Victoria/2/87 lineage and the B/Yamagata/16/88 lineage, and do not bind to the HA protein of influenza A virus subtypes, and comprise a heavy chain variable region comprising the peptide of SEQ ID NO:75, or a peptide having at least or at least about 80%, 90%, 91%, 92%, 93%, 94%, 95%, 96%, 97%, 98%, 99% or more sequence identity thereto.

In certain embodiments, the binding molecules comprise a light chain variable region comprising the peptide of SEQ ID NO:77, or a peptide having at least or at least about 80%, 90%, 91%, 92%, 93%, 94%, 95%, 96%, 97%, 98%, 99% or more sequence identity thereto.

In certain embodiments, the binding molecules comprise heavy chain variable region comprising the peptide of SEQ ID NO:75 and a light chain variable region comprising the peptide of SEQ ID NO:77.

In certain embodiments, the binding molecule comprises a heavy chain variable region consisting of the peptide of SEQ ID NO:78 and a light chain variable region consisting of the peptide of SEQ ID NO:79.

In certain embodiments, provided are binding molecules able to specifically bind to the hemagglutinin protein (HA) of an influenza B virus and able to neutralize influenza B virus strains of both the B/Victoria/2/87 lineage and the B/Yamagata/16/88 lineage, wherein the binding molecules do not bind to the HA protein of influenza A virus subtypes, and wherein the binding molecules comprise a heavy chain CDR1, comprising the peptide of SEQ ID NO:7; a heavy chain CDR2, comprising the peptide of SEQ ID NO:8, and a heavy chain CDR3, comprising the peptide of SEQ ID NO:9.

In certain embodiments, the binding molecules comprise a light chain CDR1, comprising the peptide of SEQ ID NO:10, a light chain CDR2, comprising the peptide of SEQ ID NO:11, and a light chain CDR3, comprising the peptide of SEQ ID NO:12 or 13.

In certain embodiments, the binding molecule comprises a heavy chain CDR1 comprising the peptide of SEQ ID NO:7, a heavy chain CDR2 comprising the peptide of SEQ ID NO:8, and a heavy chain CDR3 comprising the peptide of SEQ ID NO:9, and a light chain CDR1 comprising the peptide of SEQ ID NO:10, a light chain CDR2 comprising the peptide of SEQ ID NO:11, and a light chain CDR3 comprising the peptide of SEQ ID NO:12.

In certain embodiments, the binding molecule comprises a heavy chain CDR1 comprising the peptide of SEQ ID NO:7, a heavy chain CDR2 comprising the peptide of SEQ ID NO:8, and a heavy chain CDR3 comprising the peptide of SEQ ID NO:9, and a light chain CDR1 comprising the peptide of SEQ ID NO:10, a light chain CDR2 comprising the peptide of SEQ ID NO:11, and a light chain CDR3 comprising the peptide of SEQ ID NO:13.

Further provided are binding molecules that immunospecifically bind to the same epitope on an influenza B virus HA protein as a binding molecule, comprising a heavy chain variable sequence comprising the peptide of SEQ ID NO:75 and a light chain variable region comprising the peptide of SEQ ID NO:77.

In certain embodiments, the binding molecule comprises a heavy chain CDR1 comprising the peptide of SEQ ID NO:20, a heavy chain CDR2 comprising the peptide of SEQ ID NO:21, and a heavy chain CDR3 comprising the peptide of SEQ ID NO:22, and a light chain CDR1 comprising the peptide of SEQ ID NO:23, a light chain CDR2 comprising the peptide of SEQ ID NO:24, and a light chain CDR3 comprising the peptide of SEQ ID NO:25.

In certain embodiments, the binding molecule comprises a heavy chain CDR1 comprising the peptide of SEQ ID NO:31, a heavy chain CDR2 comprising the peptide of SEQ ID NO:32, and a heavy chain CDR3 comprising the peptide of SEQ ID NO:33, and a light chain CDR1 comprising the peptide of SEQ ID NO:4, a light chain CDR2 comprising the peptide of SEQ ID NO:5, and a light chain CDR3 comprising the peptide of SEQ ID NO:34.

In certain embodiments, provided are binding molecules, able to specifically bind to the hemagglutinin protein (HA) and able to neutralize influenza B virus strains of the B/Victoria lineage, in particular the influenza B virus strain B/Malaysia/2506/2004, when the amino acid on position 168 of HA of the influenza B virus, in particular the influenza B virus strain B/Malaysia/2506/2004, is proline (P), and also able to neutralize influenza B virus strains of the B/Victoria lineage, in particular B/Malaysia/2506/2004, when the amino acid on position 168 of the HA of the influenza B virus, in particular B/Malaysia/2506/2004, is glutamine (Q).

In certain embodiments, provided are binding molecules, able to specifically bind to the hemagglutinin protein (HA) and able to neutralize influenza B virus strains of the B/Yamagata lineage, in particular the influenza B virus strain B/Florida/04/2006, when the amino acid on position 38 of HA of the influenza B virus, in particular the influenza B virus strain B/Florida/04/200, is lysine (K), and unable to neutralize influenza B virus strains of the B/Yamagata lineage, in particular B/Florida/04/2006, when the amino acid on position 38 of HA of the influenza B virus, in particular B/Florida/04/2006, is glutamic acid (E).

Further provided are binding molecules, able to specifically bind to the hemagglutinin protein (HA) of an influenza B virus and able to neutralize influenza B virus strains of both the B/Victoria/2/87 lineage and the B/Yamagata/16/88 lineage, wherein the binding molecules do not bind to the HA protein of influenza A virus subtypes, and wherein the binding molecules comprise a heavy chain variable region comprising the peptide of SEQ ID NO:113 or a peptide having at least or at least about 80%, 90%, 91%, 92%, 93%, 94%, 95%, 96%, 97%, 98%, 99% or more sequence identity thereto.

In certain embodiments, the binding molecules comprise a light chain variable region comprising the peptide of SEQ ID NO:115, or a peptide having at least or at least about 80%, 90%, 91%, 92%, 93%, 94%, 95%, 96%, 97%, 98%, 99% or more sequence identity thereto.

In one embodiment, the binding molecule comprises a heavy chain variable region comprising the peptide of SEQ ID NO:113 and a light chain variable region comprising the peptide of SEQ ID NO:115.

In certain embodiments, provided are binding molecules able to specifically bind to the hemagglutinin protein (HA) of an influenza B virus and able to neutralize influenza B virus strains of both the B/Victoria/2/87 lineage and the B/Yamagata/16/88 lineage, wherein the binding molecules do not bind to the HA protein of influenza A virus subtypes, and wherein the binding molecules comprise a heavy chain CDR1, comprising the peptide of SEQ ID NO:54; a heavy chain CDR2, comprising the peptide of SEQ ID NO:55 and a heavy chain CDR3, comprising the peptide of SEQ ID NO:56.

In certain embodiments, the binding molecules comprise a light chain CDR1, comprising the peptide of SEQ ID NO:57, a light chain CDR2, comprising the peptide of SEQ ID NO:5, and a light chain CDR3, comprising the peptide of SEQ ID NO:58.

In certain embodiments, the binding molecule comprises a heavy chain CDR1 comprising the peptide of SEQ ID NO:54, a heavy chain CDR2 comprising the peptide of SEQ ID NO:55, and a heavy chain CDR3 comprising the peptide of SEQ ID NO:56, and a light chain CDR1 comprising the peptide of SEQ ID NO:57 a light chain CDR2 comprising the peptide of SEQ ID NO:5, and a light chain CDR3 comprising the peptide of SEQ ID NO:58.

Further provided are binding molecules that immunospecifically bind to the same epitope on an influenza B virus HA protein as a binding molecule, comprising a heavy chain variable sequence comprising the peptide of SEQ ID NO:113 and a light chain variable region comprising the peptide of SEQ ID NO:115.

Influenza B viruses, like influenza A viruses, infect cells by binding to sialic acid residues on the cell surface of target cells and following transfer into endosomes, by fusing their membranes with the endosomal membranes and releasing the genome-transcriptase complex into the cell. Both receptor binding and membrane fusion process are mediated by the HA glycoprotein. The HA of both influenza A and B viruses comprises two structurally distinct regions, i.e., a globular head region, which contains a receptor binding site which is responsible for virus attachment to the target cell, and which is involved in the hemagglutination activity of HA, and a stem region, containing a fusion peptide which is necessary for membrane fusion between the viral envelope and the endosomal membrane of the cell. The HA protein is a trimer in which each monomer consists of two disulphide-linked glycopolypeptides, HA1 and HA2, that are produced during infection by proteolytic cleavage of a precursor (HA0). Cleavage is necessary for virus infectivity since it is required to prime the HA for membrane fusion, to allow conformational change. Activation of the primed molecule occurs at low pH in endosomes, between pH5 and pH6, and requires extensive changes in HA structure.

In certain embodiments, the binding molecules are able to specifically bind to the HA1 subunit of the HA protein, in particular to the head region of the HA1 subunit. The binding molecules may be able to specifically bind to linear or structural and/or conformational epitopes on the HA1. subunit of the HA protein. The HA molecule may be purified from viruses or recombinantly produced and optionally isolated before use. Alternatively, HA may be expressed on the surface of cells.

The binding molecules hereof may be able to specifically bind to influenza B viruses that are viable, living and/or infective or that are in inactivated/attenuated form. Methods for inactivating/attenuating virus, e.g., influenza viruses are well known in the art and include, but are not limited to, treatment with formalin, β-propiolactone (BPL), merthiolate, and/or ultraviolet light.

The binding molecules may also be able to specifically bind to one or more fragments of the influenza B viruses, such as inter alia a preparation of one or more proteins and/or (poly)peptides, derived from subtypes of influenza B viruses or one or more recombinantly produced proteins and/or polypeptides of influenza B viruses. The nucleotide and/or peptide information of proteins of various influenza B strains can be found in the GenBank-database, NCBI Influenza Virus Sequence Database, Influenza Sequence Database (ISD), EMBL-database and/or other databases. A skilled person can find such sequences in the respective databases.

In another embodiment, the binding molecules hereof are able to specifically bind to a fragment of the above-mentioned proteins and/or polypeptides, wherein the fragment at least comprises an epitope recognized by the binding molecules hereof. An "epitope" as used herein is a moiety that is capable of binding to a binding molecule hereof with sufficiently high affinity to form a detectable antigen-binding molecule complex.

The binding molecules hereof can be intact immunoglobulin molecules such as monoclonal antibodies, or the binding molecules can be antigen-binding fragments thereof, including, but not limited to, heavy and light chain variable regions, Fab, F(ab'), F(ab)$_2$, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to influenza virus strains or a fragment thereof. In a preferred embodiment the binding molecules hereof are human monoclonal antibodies, and/or antigen-binding fragments thereof. The binding molecules may also be nanobodies, alphabodies, affibodies, FN3-domain scaffolds and other scaffolds based upon domains in (human) repeat proteins, like Adnectins, Anticalins, Darpins, etc., or other scaffolds comprising epitope binding sequences.

In certain embodiments, the binding molecules are intact antibodies comprising complete heavy and light chain variable regions as well as complete heavy and light chain constant regions.

In certain embodiments, the binding molecules have complement-dependent cytotoxic activity (CDC) and/or antibody-dependent cell-mediated cytotoxic (ADCC) activity.

The binding molecules hereof can be used in non-isolated or isolated form. Furthermore, the binding molecules can be used alone or in a mixture comprising at least one binding molecule (or variant or fragment thereof) hereof, and one or more other binding molecules that bind to influenza and have influenza virus inhibiting effect. In other words, the binding molecules can be used in combination, e.g., as a pharmaceutical composition comprising two or more binding molecules, variants or fragments thereof. For example, binding molecules having different, but complementary activities can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. Optionally, the mixture may also comprise at least one binding molecule hereof and at least one other therapeutic agent. Preferably, the therapeutic agent such as, e.g., M2 inhibitors (e.g., amantidine, rimantadine) and/or neuraminidase inhibitors (e.g., zanamivir, oseltamivir) is useful in the prophylaxis and/or treatment of an influenza virus infection Typically, a binding molecule can bind to its binding partners, i.e., an influenza B virus of the B/Yamagata and/or B/Victoria lineage, and/or fragments thereof, with an affinity constant ($K_d$-value) that is lower than $0.2 \times 10^{-4}$ M, $1.0 \times 10^{-5}$ M, $1.0 \times 10^{-6}$ M, $1.0 \times 10^{-7}$ M, preferably lower than $1.0 \times 10^{-8}$ M, more preferably lower than $1.0 \times 10^{-9}$ M, more preferably lower than $1.0 \times 10^{-10}$ M, even more preferably lower than $1.0 \times 10^{-11}$ M, and in particular lower than $1.0 \times 10^{-12}$ M. The affinity constants can vary for antibody isotypes. For example, affinity binding for an IgM isotype refers to a binding affinity of at least about $1.0 \times 10^{-7}$ M. Affinity constants can for instance be measured using surface plasmon resonance, for example using the BIACORE system (Pharmacia Biosensor AB, Uppsala, Sweden).

The binding molecules hereof exhibit neutralizing activity. Neutralizing activity can, for instance, be measured as described herein. Alternative assays measuring neutralizing activity are described in for instance WHO Manual on Animal Influenza Diagnosis and Surveillance, Geneva: World Health Organization, 2005, version 2002.5.

Typically, the binding molecules hereof have a neutralizing activity of 50 µg/ml or less, preferably 20 pg/ml or less, more preferably a neutralizing activity of 10 µg/ml or less, even more preferably 5 µg/ml or less, as determined in an in vitro virus neutralization assay (VNA) as described in Example 6. The binding molecules hereof may bind to influenza virus or a fragment thereof in soluble form such as for instance in a sample or in suspension or may bind to influenza viruses or fragments thereof bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the binding molecules may bind to influenza virus in purified/isolated or non-purified/non-isolated form.

As discussed above, the instant disclosure in certain embodiments provides isolated human binding molecules that are able to recognize and bind to an epitope in the influenza hemagglutinin protein (HA) of influenza B viruses, wherein the binding molecules have neutralizing activity against influenza B viruses of both the B/Yamagata and/or B/Victoria lineages, both in vitro and in vivo. Hereof, it has been shown that binding molecules hereof cross-neutralize influenza virus subtypes belonging to both phylogenetic lineages. The skilled person, based upon what has been disclosed herein, can determine whether an antibody indeed cross-reacts with HA proteins from different subtypes and can also determine whether they are able to neutralize influenza viruses of different subtypes in vitro and/or in vivo.

Another aspect includes functional variants of the binding molecule as defined herein. Molecules are considered to be functional variants of a binding molecule hereof, if the variant binding molecules are capable of competing for immunospecifically binding to an influenza virus or a fragment thereof with the "parental" or "reference" binding molecules. In other words, molecules are considered to be functional variants of a binding molecule hereof when the functional variants are still capable of binding to the same or overlapping epitope of the influenza virus or a fragment thereof. For the sake of this application "parental" and "reference" will be used as synonyms meaning that the information of the reference or parental molecule, or the physical molecule itself may form the basis for the variation. Functional variants include, but are not limited to, derivatives that are substantially similar in primary structural sequence, including those that have modifications in the Fc receptor or other regions involved with effector functions, and/or which contain e.g., in vitro or in vivo modifications, chemical and/or biochemical, that are not found in the parental binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like. Alternatively, functional variants can be binding molecules as defined in the instant disclosure comprising a peptide containing substitutions, insertions, deletions or combinations thereof of one or more amino acids compared to the peptides of the parental binding molecules. Furthermore, functional variants can comprise truncations of the peptide at either or both the amino or carboxyl termini. Functional variants hereof may have the same or different, either higher or lower, binding affinities compared to the parental binding molecule but are still capable of binding to the influenza virus or a fragment thereof. For instance, functional variants hereof may have increased or decreased binding affinities for an influenza virus or a fragment thereof compared to the parental binding molecules. In certain embodiments, the peptides of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope hereof have at least about 80% to about 99%, preferably at least about 70% to about 99%, more preferably at least about 80% to about 99%, even more preferably at least about 90% to about 99%, most preferably at least about 95% to about 99%, in particular at least about 97% to about 99% peptide identity and/or homology with the parental binding molecules as defined herein. Computer algorithms such as inter alia Gap or Bestfit known to a person skilled in the art can be used to optimally align peptides to be compared and to define similar or identical amino acid residues. Functional variants can be obtained by altering the parental binding molecules or parts thereof by general molecular biology methods known in the art including, but not limited to, error-prone PCR, oligonucleotide-directed mutagenesis, site-directed mutagenesis and heavy and/or light chain shuffling.

In certain embodiments, the functional variants have neutralizing activity against influenza B viruses. The neutralizing activity may either be identical, or higher or lower compared to the parental binding molecules. As used herein, when the term (human) binding molecule is used, this also encompasses functional variants of the (human) binding molecule. Assays for verifying if a variant binding molecule has neutralizing activity are well known in the art (see *WHO Manual on Animal Influenza Diagnosis and Surveillance*, Geneva: World Health Organization, 2005 version 2002.5).

In certain embodiments, the functional variants are binding molecules comprising a heavy chain variable sequence comprising one or more amino acid mutations, such as one, two, three, four, five, six, seven, eight, nine, ten, eleven, twelve, thirteen, fourteen or fifteen amino acid mutations, as compared to SEQ ID NO:71 and/or a light chain variable region comprising one or more amino acid mutations, such as one, two, three, four, five, six, seven, eight, nine, ten, eleven, twelve, thirteen, fourteen or fifteen amino acid mutations as compared to SEQ ID NO:73.

In certain embodiments, the functional variants are binding molecules comprising a heavy chain variable sequence comprising one or more amino acid mutations, such as one, two, three, four, five, six, seven, eight, nine, ten, eleven, twelve, thirteen, fourteen or fifteen amino acid mutations, as compared to SEQ ID NO:75 and/or a light chain variable region comprising one or more amino acid mutations, such as one, two, three, four, five, six, seven, eight, nine, ten, eleven, twelve, thirteen, fourteen or fifteen amino acid mutations as compared to SEQ ID NO:77.

In certain embodiments, the functional variants are binding molecules comprising a heavy chain variable sequence comprising one or more amino acid mutations, such as one, two, three, four, five, six, seven, eight, nine, ten, eleven, twelve, thirteen, fourteen or fifteen amino acid mutations, as compared to SEQ ID NO:113 and/or a light chain variable region comprising one or more amino acid mutations, such as one, two, three, four, five, six, seven, eight, nine, ten, eleven, twelve, thirteen, fourteen or fifteen amino acid mutations as compared to SEQ ID NO:115.

In certain embodiments, the binding molecule is selected from the group binding molecules consisting of:
- (a) a heavy chain CDR1 comprising the peptide of SEQ ID NO:59, a heavy chain CDR2 comprising the peptide of SEQ ID NO:2, and a heavy chain CDR3 comprising the peptide of SEQ ID NO:3, and a light chain CDR1 comprising the peptide of SEQ ID NO:17, a light chain CDR2 comprising the peptide of SEQ ID NO:18, and a light chain CDR3 comprising the peptide of SEQ ID NO:60;
- (b) a heavy chain CDR1 comprising the peptide of SEQ ID NO:61, a heavy chain CDR2 comprising the peptide of SEQ ID NO:2, and a heavy chain CDR3 comprising the peptide of SEQ ID NO:3, and a light chain CDR1 comprising the peptide of SEQ ID NO:62, a light chain CDR2 comprising the peptide of SEQ ID NO:18, and a light chain CDR3 comprising the peptide of SEQ ID NO:63;
- (c) a heavy chain CDR1 comprising the peptide of SEQ ID NO:59, a heavy chain CDR2 comprising the peptide of SEQ ID NO:2, and a heavy chain CDR3 comprising the peptide of SEQ ID NO:3, and a light chain CDR1 comprising the peptide of SEQ ID NO:64, a light chain CDR2 comprising the peptide of SEQ ID NO:65, and a light chain CDR3 comprising the peptide of SEQ ID NO:66; and
- (d) a heavy chain CDR1 comprising the peptide of SEQ ID NO:59, a heavy chain CDR2 comprising the peptide of SEQ ID NO:2, and a heavy chain CDR3 comprising the peptide of SEQ ID NO:3, and a light chain CDR1 comprising the peptide of SEQ ID NO:67, a light chain CDR2 comprising the peptide of SEQ ID NO:68, and a light chain CDR3 comprising the peptide of SEQ ID NO:69;
- (e) a heavy chain CDR1 comprising the peptide of SEQ ID NO:35, a heavy chain CDR2 comprising the peptide of SEQ ID NO:36 and a heavy chain CDR3 comprising the peptide of SEQ ID NO:37, and a light chain CDR1 comprising the peptide of SEQ ID NO:4, a light chain CDR2 comprising the peptide of SEQ ID NO:38, and a light chain CDR3 comprising the peptide of SEQ ID NO:39;
- (f) a heavy chain CDR1 comprising the peptide of SEQ ID NO:40, a heavy chain CDR2 comprising the peptide of SEQ ID NO:41, and a heavy chain CDR3 comprising the peptide of SEQ ID NO:42, and a light chain CDR1 comprising the peptide of SEQ ID NO:43, a light chain CDR2 comprising the peptide of SEQ ID NO:5, and a light chain CDR3 comprising the peptide of SEQ ID NO:44;
- (g) a heavy chain CDR1 comprising the peptide of SEQ ID NO:45, a heavy chain CDR2 comprising the peptide of SEQ ID NO:46, and a heavy chain CDR3 comprising the peptide of SEQ ID NO:47, and a light chain CDR1 comprising the peptide of SEQ ID NO:48, a light chain CDR2 comprising the peptide of SEQ ID NO:38, and a light chain CDR3 comprising the peptide of SEQ ID NO:49; and
- (h) a heavy chain CDR1 comprising the peptide of SEQ ID NO:45, a heavy chain CDR2 comprising the peptide of SEQ ID NO:50, and a heavy chain CDR3 comprising the peptide of SEQ ID NO:47, and a light chain CDR1 comprising the peptide of SEQ ID NO:51, a light chain CDR2 comprising the peptide of SEQ ID NO:52, and a light chain CDR3 comprising the peptide of SEQ ID NO:53.

In certain embodiments, the binding molecule is selected from the group consisting of:
- (a) a binding molecule comprising a heavy chain variable region of SEQ ID NO:119 and a light chain variable region of SEQ ID NO:121;
- (b) a binding molecule comprising a heavy chain variable region of SEQ ID NO:123 and a light chain variable region of SEQ ID NO:125;
- (c) a binding molecule comprising a heavy chain variable region of SEQ ID NO:127 and a light chain variable region of SEQ ID NO:129;
- (d) a binding molecule comprising a heavy chain variable region of SEQ ID NO:131 and a light chain variable region of SEQ ID NO:133;
- (e) a binding molecule comprising a heavy chain variable region of SEQ ID NO:77 and a light chain variable region of SEQ ID NO:79;
- (f) a binding molecule comprising a heavy chain variable region of SEQ ID NO:101 and a light chain variable region of SEQ ID NO:103;
- (g) a binding molecule comprising a heavy chain variable region of SEQ ID NO:105 and a light chain variable region of SEQ ID NO:107; and
- (h) a binding molecule comprising a heavy chain variable region of SEQ ID NO:109 and a light chain variable region of SEQ ID NO:111.

In certain embodiments, the binding molecules are for use as a medicament, and preferably for use in the therapeutic and/or prophylactic treatment of influenza infection caused by influenza B viruses. The influenza virus that causes the influenza infection and that can be treated using the binding molecules hereof may be an influenza B virus of the B/Yamagata and/or B/Victoria lineage.

Also disclosed are pharmaceutical compositions comprising at least one binding molecule hereof, and at least a pharmaceutically acceptable excipient.

In yet another embodiment, disclosed is the use of a binding molecule in the preparation of a medicament for the prophylaxis, and/or treatment of an influenza virus infection.

The influenza virus infections that can be prevented and/or treated using the binding molecules hereof may occur in small populations, but can also spread around the world in seasonal epidemics or, worse, in global pandemics where millions of individuals are at risk. Provided are binding molecules that can neutralize the infection of influenza strains that cause such seasonal epidemics, as well as potential pandemics.

In yet a further aspect, provided are immunoconjugates, i.e., molecules comprising at least one binding molecule as defined herein and further comprising at least one tag, such as inter alia a detectable moiety/agent. Also contemplated in the instant disclosure are mixtures of immunoconjugates hereof or mixtures of at least one immunoconjugates hereof and another molecule, such as a therapeutic agent or another binding molecule or immunoconjugate. In further embodiments, the immunoconjugates hereof may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates hereof may be therapeutic agents, but they can also be detectable moieties/agents. Tags suitable in therapy and/or prevention may be toxins or functional parts thereof, antibiotics, enzymes, other binding molecules that enhance phagocytosis or immune stimulation. Immunoconjugates comprising a detectable agent can be used diagnostically to, for example, assess if a subject has been infected with an influenza virus or to monitor the development or progression of an influenza virus infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

Furthermore, the binding molecules or immunoconjugates hereof can also be attached to solid supports, which are particularly useful for in vitro immunoassays or purification of influenza viruses or fragments thereof. Such solid supports might be porous or nonporous, planar or non-planar. The binding molecules hereof can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect, the binding molecules may be conjugated/attached to one or more antigens. Preferably, these antigens are antigens that are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules hereof will bind to influenza virus HA and the antigens attached to the binding molecules will initiate a powerful T-cell attack on the conjugate, which will eventually lead to the destruction of the influenza virus.

Next to producing immunoconjugates chemically by conjugating, directly or indirectly, via for instance a linker, the immunoconjugates can be produced as fusion proteins comprising the binding molecules hereof and a suitable tag. Fusion proteins can be produced by methods known in the art such as, e.g., recombinantly by constructing nucleic acid molecules comprising polynucleotides encoding the binding molecules in frame with polynucleotides encoding the suitable tag(s) and then expressing the nucleic acid molecules.

Also provided are nucleic acid molecules encoding at least a binding molecule, functional variant or immunoconjugate hereof. Such nucleic acid molecules can be used as intermediates for cloning purposes, e.g., in the process of affinity maturation as described above. In a preferred embodiment, the nucleic acid molecules are isolated or purified.

The skilled man will appreciate that functional variants of these nucleic acid molecules are also intended to be a part hereof. Functional variants are polynucleotides that can be directly translated, using the standard genetic code, to provide a peptide identical to that translated from the parental nucleic acid molecules.

Preferably, the nucleic acid molecules encode binding molecules comprising the CDR regions as described above. In a further embodiment the nucleic acid molecules encode binding molecules comprising two, three, four, five or even all six CDR regions of the binding molecules hereof.

In another embodiment, the nucleic acid molecules encode binding molecules comprising a heavy chain comprising the variable heavy chain sequences as described above. In another embodiment the nucleic acid molecules encode binding molecules comprising a light chain comprising the variable light chain sequences as described above. The polynucleotides and the peptides of the heavy and light chain variable regions of the binding molecules hereof are given below.

Also provided are vectors (e.g., nucleic acid constructs) comprising one or more nucleic acid molecules according to the instant disclosure. Vectors can be derived from plasmids such as inter alia F, R1, RP1, Col, pBR322, TOL, Ti, etc; cosmids; phages such as lambda, lambdoid, M13, Mu, P1, P22, Qr3, T-even, T-odd, T2, T4, T7, etc; plant viruses. Vectors can be used for cloning and/or for expression of the binding molecules hereof and might even be used for gene therapy purposes. Vectors comprising one or more nucleic acid molecules hereof operably linked to one or more expression-regulating nucleic acid molecules are also covered by the instant disclosure. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, and thymidine kinase gene from Herpes simplex virus (HSV-TK), dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional aspect hereof. The hosts may be host cells. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells, NSO cells or Bowes melanoma cells are preferred in the instant disclosure. Mammalian cells provide expressed proteins with posttranslational modifications that are most similar to natural molecules of mammalian origin. Since the instant disclosure deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a polynucleotide encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application "PER.C6 cells" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403 the disclosure of which is incorporated herein by reference in its entirety.

A method of producing a binding molecule hereof is an additional aspect. Such a method comprises the steps of a) culturing a host hereof under conditions conducive to the expression of the binding molecule, and b) optionally, recovering the expressed binding molecule. The expressed binding molecules can be recovered from the cell free extract, but preferably they are recovered from the culture medium. This method of producing can also be used to make functional variants of the binding molecules and/or immunoconjugates hereof. Methods to recover proteins, such as binding molecules, from cell free extracts or culture medium are well known to the man skilled in the art. Binding molecules, functional variants and/or immunoconjugates obtainable by the above-described method are also a part hereof.

Alternatively, next to the expression in hosts, such as host cells, the binding molecules and immunoconjugates hereof can be produced synthetically by conventional peptide synthesizers or in cell-free translation systems using RNA nucleic acid derived from DNA molecules hereof. Binding molecules and immunoconjugates as obtainable by the above described synthetic production methods or cell-free translation systems are also a part hereof.

In yet another embodiment, binding molecules hereof can also be produced in transgenic, non-human, mammals such as inter alia rabbits, goats or cows, and secreted into for instance the milk thereof.

In yet another alternative embodiment, binding molecules hereof may be generated by transgenic non-human mammals, such as, for instance, transgenic mice or rabbits that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of influenza virus or a fragment thereof. Protocols for immunizing non-human mammals are well established in the art. See *Using Antibodies: A Laboratory Manual*, edited by: E. Harlow, D. Lane (1998), Cold Spring Harbor Laboratory, Cold Spring Harbor, N.Y.; and *Current Protocols in Immunology*, edited by: J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B-cells, plasma and/or memory cells derived from the transgenic animals. In yet another embodiment, the human binding molecules are produced by hybridomas, which are prepared by fusion of B-cells obtained from the above-described transgenic non-human mammals to immortalized cells. B-cells, plasma cells and hybridomas as obtainable from the above-described transgenic non-human mammals and human binding molecules as obtainable from the above-described transgenic non-human mammals, B-cells, plasma and/or memory cells and hybridomas are also a part hereof.

In yet a further aspect, provided are compositions comprising at least a binding molecule, preferably a human monoclonal antibody, at least a functional variant thereof, at least an immunoconjugate hereof and/or a combination thereof. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. If necessary, the human binding molecules hereof may be coated in or on a material to protect them from the action of acids or other natural or non-natural conditions that may inactivate the binding molecules.

In yet a further aspect, provided are compositions comprising at least a nucleic acid molecule as defined in the instant disclosure. The compositions may comprise aqueous solutions such as aqueous solutions containing salts (e.g., NaCl or salts as described above), detergents (e.g., SDS) and/or other suitable components.

Furthermore, the disclosure pertains to pharmaceutical compositions comprising at least a binding molecule, such as a human monoclonal antibody, hereof (or functional fragment or variant thereof), at least an immunoconjugate hereof, at least a composition hereof, or combinations thereof. The phaimaceutical composition hereof further comprises at least one pharmaceutically acceptable excipient. Pharmaceutically acceptable excipients are well known to the skilled person.

The pharmaceutical composition hereof may further comprise at least one other therapeutic agent. Suitable agents are also well known to the skilled artisan.

In certain embodiments the pharmaceutical composition comprises at least one additional binding molecule, i.e., the pharmaceutical composition can be a cocktail or mixture of binding molecules. The pharmaceutical composition may comprise at least two binding molecules hereof, or at least one binding molecule hereof and at least one further influenza virus binding and/or neutralizing molecule, such as another antibody directed against the HA protein or against other antigenic structures present on influenza viruses, such as M2, and/or a binding molecules neutralizing one or more other pathogens. In another embodiment the additional binding molecule may be formulated for simultaneous separate or sequential administration.

In certain embodiments, the binding molecules exhibit synergistic neutralizing activity, when used in combination. As used herein, the term "synergistic" means that the combined effects of the binding molecules when used in combination are greater than their additive effects when used individually. The synergistically acting binding molecules may bind to different structures on the same or distinct fragments of influenza virus. A way of calculating synergy is by means of the combination index. The concept of the combination index (CI) has been described by Chou and Talalay (1984). The compositions may, e.g., comprise one binding molecule having neutralizing activity and one non-neutralizing binding molecule. The non-neutralizing and neutralizing binding molecules may also act synergistically in neutralizing influenza virus.

In certain embodiments, the pharmaceutical composition may comprise at least one binding molecule hereof and at least one further binding molecule, preferably a further influenza virus neutralizing binding molecule. The binding molecules in the pharmaceutical composition preferably are capable of reacting with influenza viruses of different subtypes. The binding molecules may be of high affinity and have a broad specificity. Preferably, both binding molecules are cross-neutralizing molecules in that they each neutralize influenza viruses of different subtypes. In addition, preferably they neutralize as many strains of each of the different influenza virus subtypes as possible.

In certain embodiments, the pharmaceutical composition comprises at least one other prophylactic and/or therapeutic agent. Preferably, the further therapeutic and/or prophylactic agents are agents capable of preventing and/or treating an influenza virus infection and/or a condition resulting from such an infection. Therapeutic and/or prophylactic agents include, but are not limited to, anti-viral agents. Such agents can be binding molecules, small molecules, organic or inorganic compounds, enzymes, polynucleotides, anti-viral peptides, etc. Other agents that are currently used to treat patients infected with influenza viruses are M2 inhibitors (e.g., amantidine, rimantadine) and/or neuraminidase inhibitors (e.g., zanamivir, oseltamivir). These can be used in combination with the binding molecules hereof "In combination" herein means simultaneously, as separate formulations, or as one single combined formulation, or according to a sequential administration regimen as separate formulations, in any order. Agents capable of preventing and/or treating an infection with influenza virus and/or a condition resulting from such an infection that are in the experimental phase might also be used as other therapeutic and/or prophylactic agents useful in the instant disclosure.

The binding molecules or pharmaceutical compositions hereof can be tested in suitable animal model systems prior to use in humans. Such animal model systems include, but are not limited to, mouse, ferret and monkey.

Typically, pharmaceutical compositions must be sterile and stable under the conditions of manufacture and storage. The binding molecules, immunoconjugates, or compositions hereof can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, or compositions hereof can be in solution and the appropriate pharmaceutically acceptable excipient can be added and/or mixed before or at the time of delivery to provide a unit dosage injectable form. Preferably, the pharmaceutically acceptable excipient used in the instant disclosure is suitable to high drug concentration, can maintain proper fluidity and, if necessary, can delay absorption.

The choice of the optimal route of administration of the pharmaceutical compositions will be influenced by several factors including the physicochemical properties of the active molecules within the compositions, the urgency of the clinical situation and the relationship of the plasma concentrations of the active molecules to the desired therapeutic effect. For instance, if necessary, the binding molecules hereof can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration. The preferred administration route is intravenous or by inhalation.

Oral dosage forms can be formulated inter alia as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutically excipients including, but not limited to, inert diluents, granulating and disintegrating agents, binding agents, lubricating agents, preservatives, coloring, flavoring or sweetening agents, vegetable or mineral oils, wetting agents, and thickening agents.

The pharmaceutical compositions hereof can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anesthetic agents, preservatives, buffers, viscosity or solubility increasing agents, water-soluble antioxidants, oil-soluble antioxidants and metal chelating agents.

In a further aspect, the binding molecules such as human monoclonal antibodies (functional fragments and variants thereof), immunoconjugates, compositions, or pharmaceutical compositions hereof can be used as a medicament or diagnostic agent. So, methods of diagnosis, treatment and/or prevention of an influenza virus infection using the binding molecules, immunoconjugates, compositions, or pharmaceutical compositions hereof are another aspect hereof. The above-mentioned molecules can inter alia be used in the diagnosis, prophylaxis, treatment, or combination thereof, of an influenza virus infection caused by an influenza B virus. They are suitable for treatment of yet untreated patients suffering from an influenza virus infection and patients who have been or are treated for an influenza virus infection.

The above-mentioned molecules or compositions may be employed in conjunction with other molecules useful in diagnosis, prophylaxis and/or treatment. They can be used in vitro, ex vivo or in vivo. For instance, the binding molecules such as human monoclonal antibodies (or functional variants thereof), immunoconjugates, compositions or pharmaceutical compositions hereof can be co-administered with a vaccine against influenza virus (if available). Alternatively, the vaccine may also be administered before or after administration of the molecules hereof. Instead of a vaccine, anti-viral agents can also be employed in conjunction with the binding molecules hereof. Suitable anti-viral agents are mentioned above.

The molecules are typically formulated in the compositions and pharmaceutical compositions hereof in a therapeutically or diagnostically effective amount. Alternatively, they may be formulated and administered separately. For instance the other molecules such as the anti-viral agents may be applied systemically, while the binding molecules hereof may be applied intravenously.

Treatment may be targeted at patient groups that are susceptible to influenza infection. Such patient groups include, but are not limited to e.g., the elderly (e.g., ≥50 years old, ≥60 years old, and preferably ≥65 years old), the young (e.g., ≤5 years old, ≤1 year old), hospitalized patients and already infected patients who have been treated with an antiviral compound but have shown an inadequate antiviral response.

Dosage regimens can be adjusted to provide the optimum desired response (e.g., a therapeutic response). A suitable dosage range may for instance be 0.01 to 100 mg/kg body weight, preferably 0.1 to 50 mg/kg body weight, preferably 0.01 to 15 mg/kg body weight. Furthermore, for example, a single bolus may be administered, several divided doses may be administered over time or the dose may be proportionally reduced or increased as indicated by the exigencies of the therapeutic situation. The molecules and compositions according to the instant disclosure are preferably sterile. Methods to render these molecules and compositions sterile are well known in the art. The other molecules useful in diagnosis, prophylaxis and/or treatment can be administered in a similar dosage regimen as proposed for the binding molecules hereof. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more of the human binding molecules or pharmaceutical compositions hereof. The exact dosing regimen is usually sorted out during clinical trials in human patients.

Human binding molecules and pharmaceutical compositions comprising the human binding molecules are particularly useful, and often preferred, when to be administered to human beings as in vivo therapeutic agents, since recipient immune response to the administered antibody will often be substantially less than that occasioned by administration of a monoclonal murine, chimeric or humanized binding molecule.

In another aspect, disclosed is the use of the binding molecules (e.g., neutralizing human monoclonal antibodies, functional fragments, of variants thereof), immunoconjugates, nucleic acid molecules, compositions or pharmaceutical compositions hereof in the preparation of a medicament for the diagnosis, prophylaxis, treatment, or combination thereof; of an influenza virus infection, in particular an influenza virus infection caused by influenza B viruses.

Also, kits comprising at least a binding molecule such as a neutralizing human monoclonal antibody (functional fragments and variants thereof), at least an immunoconjugate, at least a nucleic acid molecule, at least a composition, at least a pharmaceutical composition, at least a vector, at least a host hereof or a combination thereof are also an aspect hereof. Optionally, the above-described components of the kits hereof are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about for example the indications, usage, dosage, manufacture, administration, contra-indications and/or warnings concerning the use of such therapeutic, prophylactic or diagnostic products.

The binding molecules can also be advantageously used as a diagnostic agent in an in vitro method for the detection of influenza virus. Thus, also described is a method of detecting influenza B subtype influenza virus in a sample, wherein the method comprises the steps of (a) assaying the level of influenza B virus antigen in a biological sample using a binding molecule hereof and/or an immunoconjugate hereof; and (b) comparing the assayed level of influenza B virus antigen with a control level whereby an increase in the assayed level of influenza B virus antigen compared to the control level of the influenza B virus antigen is indicative of an influenza B virus infection.

The biological sample may be a biological sample including, but not limited to blood, serum, stool, sputum, nasopharyngeal aspirates, bronchial lavages, urine, tissue or other biological material from (potentially) infected subjects, or a non-biological sample such as water, drink, etc. The (potentially) infected subjects may be human subjects, but also animals that are suspected as carriers of influenza virus might be tested for the presence of the virus using the human binding molecules or immunoconjugates hereof. The sample may first be manipulated to make it more suitable for the method of detection. Manipulation means inter alia treating the sample suspected to contain and/or containing the virus in such a way that the virus will disintegrate into antigenic components such as proteins, (poly)peptides or other antigenic fragments. Preferably, the human binding molecules or immunoconjugates hereof are contacted with the sample under conditions which allow the formation of an immunological complex between the human binding molecules and the virus or antigenic components thereof that may be present in the sample. The formation of an immunological complex, if any, indicating the presence of the virus in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products are ELISA and Western blot techniques. ELISA tests are particularly preferred. For use as reagents in these assays, the binding molecules or immunoconjugates hereof are conveniently bonded to the inside surface of microtiter wells. The binding molecules or immunoconjugates hereof may be directly bonded to the microtiter well. However, maximum binding of the binding molecules or immunoconjugates hereof to the wells might be accomplished by pretreating the wells with polylysine prior to the addition of the binding molecules or immunoconjugates hereof. Furthermore, the binding molecules or immunoconjugates hereof may be covalently attached by known means to the wells. Generally, the binding molecules or immunoconjugates are used in a concentration between 0.01 to 100 μg/ml for coating, although higher as well as lower amounts may also be used. Samples are then added to the wells coated with the binding molecules or immunoconjugates hereof.

Further provided are methods of treating or preventing an influenza B virus infection in a subject, comprising administering to the subject a therapeutically or prophylactically effective amount of the binding molecules, immunoconjugates and/or pharmaceutical compositions hereof. In certain embodiments, the subject is a mammal, preferably a human.

Furthermore, binding molecules hereof can be used to identify specific binding structures of influenza virus. The binding structures can be epitopes on proteins and/or polypeptides. They can be linear, but also structural and/or conformational. In one embodiment, the binding structures can be analyzed by means of PEPSCAN analysis (see inter alia WO 84/03564, WO 93/09872, Slootstra et al., 1996). Alternatively, a random peptide library comprising peptides from a protein of influenza virus can be screened for peptides capable of binding to the binding molecules hereof.

The application is further described by the following Examples and Figures. The examples are not intended to limit the scope hereof in any way.

EXAMPLES

Example 1

Construction of scFv Phage Display Libraries Using RNA Extracted from Memory B Cells Peripheral blood was collected from normal healthy donors by venapuncture in EDTA anti-coagulation sample tubes. Single chain Fv (scFv) phage display libraries were obtained as described in WO 2008/028946, which is incorporated by reference herein. The final library was checked for insert frequency with a colony PCR using a primer set flanking the inserted VH-VL regions (100 to 150 single colonies). Typically, more than 95% of the colonies showed a correct length insert (see Table 1). The colony PCR products were used for subsequent DNA sequence analysis to check sequence variation and to assess the percentage of colonies showing a complete ORF. This was typically above 70% (see Table 1). The frequency of mutations in the V genes was also analyzed. About 95% of the sequences were not in germline configuration indicative of a maturation process and consistent with the memory phenotype of the B cells used as an RNA source for the library.

A two-round PCR amplification approach was applied, using the primer sets shown in WO 2008/028946, to isolate the immunoglobulin VH and VL regions from the respective donor repertoire.

First round amplification on the respective cDNA yielded seven, six and nine products of about 650 base pairs for VH, Vkappa and Vlambda regions, respectively. For IgM memory B cell VH region amplification, the OCM constant primer (IgM constant heavy chain specific) was used in combination with OH1 to OH7. The thermal cycling program for first round amplifications was: 2 minutes 96° C. (denaturation step), 35 cycles of 30 seconds 96° C./30 seconds 60° C./50 seconds 72° C., 10 minutes 72° C. final elongation and 6° C. refrigeration. The products were loaded on and isolated from a 1% agarose gel using gel-extraction columns (Macherey-Nagel, Minn.) and eluted in 50 μl 5 mM Tris-HCl pH 8.0. Ten percent of first round products (5 μl) were subjected to second round amplification. These primers were extended with restriction sites enabling the directional cloning of the respective VL and VH regions into phage display vector PDV-006. The PCR program for second round amplifications was as follows: 2 minutes 96° C. (denaturation step), 30 cycles of 30 seconds 96° C./30 seconds 60° C./50 seconds 72° C., 10 minutes 72° C. final elongation and 6° C. refrigeration. The second round products (~350 base pairs) were first loaded on gel and extracted from the agarose as above. Then the fragments were pooled according to natural occurrence of J segments found in immunoglobulin gene products, resulting in seven, six and nine pools for respectively the VH, Vkappa and Vlambda variable regions as shown in Table 1 and 2.

To obtain a normalized distribution of immunoglobulin sequences in the immune library the six Vkappa and nine Vlambda light chain pools were mixed according to the percentages mentioned in Table 1. This single final VL pool (5 μg) was digested with SalI and NotI restriction enzymes, loaded on and isolated from a 1.5% agarose gel (~350 base pairs) using MN-extraction columns and ligated in SalI-NotI cut PDV-006 vector (5000 base pairs) as follows: 500 ng PDV-006 vector, 70 ng VL insert, 5 μl 10× ligation buffer (NEB), 2.5 T4 DNA Ligase (400 U/μl) (NEB), and ultrapure water was added up to a total volume of 50 μl (vector to insert ratio was 1:2). Ligation was performed overnight in a water bath of 16° C. Next, the volume was doubled with water, extracted with an equal volume of phenol-chloroform-isoamylalcohol (75:24:1) (Invitrogen) followed by chloroform (Merck) extraction and precipitated with 1 μl Pellet Paint (Novogen), 10 μl sodium acetate (3 M pH 5.0) and 100 μl isopropanol for 2 hours at −20° C. The obtained sample was subsequently centrifuged at 20,000×g for 30 minutes at 4° C. The obtained precipitate was washed with 70% ethanol and centrifuged for 10 minutes at 20,000×g at room temperature. Ethanol was removed and the pellet was air dried for several minutes and then dissolved in 50 µl buffer containing 10 mM Tris-HCl, pH 8.0. 2 µl ligation mixture was used for the transformation of 40 µl TG-1 electro-competent cells (Agilent) in a chilled 0.1 cm electroporation cuvette (Biorad) using a Genepulser II apparatus (Biorad) set at 1.7 kV, 200 Ohm, 25 µF (time constant ~4.5 msec). Directly after pulse, the bacteria were flushed from the cuvette with 750 µl SOC medium (Invitrogen) containing 5% (w/v) glucose (Sigma) at 37° C. and transferred to a 15 ml round bottom culture tube. Another 750 µl SOC/glucose was used to flush residual bacteria from the cuvette and was added to the culture tube. Bacteria were recovered by culturing for exactly one hour at 37° C. in a shaker incubator at 220 rpm. The transformed bacteria were plated over large 240 mm square petridishes (NUNC) containing 200 ml 2TY agar (16 g/l bacto-tryptone, 10 g/l bacto-yeast extract, 5 g/l NaCl, 15 g/l agar, pH 7.0) supplemented with 50 µg/ml ampicillin and 5% (w/v) glucose (Sigma). A 1 to 1000 and a 1 to 10,000 dilution were plated for counting purposes on 15 cm petridishes containing the same medium. This transformation procedure was repeated sequentially twenty times and the complete library was plated over a total of ten large square petridishes and grown overnight in a 37° C. culture stove. Typically, around $1 \times 10^7$ cfu were obtained using the above protocol. The intermediate VL light chain library was harvested from the plates by mildly scraping the bacteria into 12 ml 2TY medium per plate. The cell mass was determined by OD600 measurement and two times 500 OD of bacteria was used for maxi plasmid DNA preparation using two maxiprep columns (MN) according to manufacturer's instructions.

Analogous to the VL variable regions, the second round VH-JH products were first mixed together to obtain the normal J segment usage distribution (see Table 2), resulting in seven VH subpools called PH1 to PH7. The pools were mixed to acquire a normalized sequence distribution using the percentages depicted in Table 2, obtaining one VH fraction that was digested with SfiI and XhoI restriction enzymes and ligated in SfiI-XhoI cut PDV-VL intermediate library obtained as described above. The ligation set-up, purification method, subsequent transformation of TG1 and harvest of bacteria was exactly as described for the VL intermediate library (see above), with the exception of the number of 240 mm plates used. For the final library twenty plates were used, resulting in approximately $2 \times 10^7$ cfu. The final library was checked for insert frequency with a colony PCR using a primer set flanking the inserted VH-VL regions (100 to 150 single colonies). Typically, more than 95% of the colonies showed a correct length insert (see Table 3). The colony PCR products were used for subsequent DNA sequence analysis to check sequence variation and to assess the percentage of colonies showing a complete ORF. This was typically above 70% (see Table 3). The frequency of mutations in the V genes was also analyzed. About 95% of the sequences were not in germline configuration indicative of a maturation process and consistent with the memory phenotype of the B cells used as an RNA source for the library. Finally, the library was rescued and amplified by using CT helper phages (see WO 02/103012) and was used for phage antibody selection by panning methods as described below.

Example 2

Selection of Phages Carrying Single Chain Fv Fragments Against Influenza B

Selection was performed using the antibody phage display libraries against recombinant hemagglutinin (HA) of influenza B (B/Ohio/01/2005, B/Florida/04/2006 and B/Brisbane/60/2008). HA antigens were diluted in PBS (5.0 µg/ml), added to MAXISORP™ Nunc-Immuno Tubes (Nunc), 2 ml per tube, and incubated overnight at 4° C. on a rotating wheel. The immunotubes were emptied and washed three times with block buffer (2% non-fat dry milk (ELK) in PBS). Subsequently, the immunotubes were filled completely with block buffer and incubated for 1 to 2 hours at room temperature. Aliquots of the phage display library (350 to 500 amplified using CT helper phage (see WO 02/103012)) were blocked in blocking buffer (optionally: supplemented with 10% non-heat inactivated fetal bovine serum and 2% mouse serum) for 1 to 2 hours at room temperature. The blocked phage library was added to the immunotubes, incubated for 2 hours at room temperature, and washed with wash buffer (0.05% (v/v) TWEEN®-20 in PBS) to remove unbound phages. Bound phages were eluted from the respective antigen by incubation with 1 ml of 100 mM triethylamine (TEA) for 10 minutes at room temperature. Subsequently, the eluted phages were mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for 10 minutes at 3000×g at room temperature and the bacterial pellet was resuspended in 0.5 ml 2-trypton yeast extract (2TY) medium. The obtained bacterial suspension was divided over two 2TY agar plates supplemented with tetracycline, ampicillin and glucose. After incubation overnight of the plates at 37° C., the colonies were scraped from the plates and used to prepare an enriched phage library, essentially as described by De Kruif et al. (1995a) and in WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of PBS with 1% bovine serum albumin (BSA), filter-sterilized and used for the next round of selection. The second round of selection was performed either on the same HA subtype or on HA of a different subtype.

Two consecutive rounds of selections were performed before isolation of individual single-chain phage antibodies. After the second round of selection, individual *E. coli* colonies were used to prepare monoclonal phage antibodies. Essentially, individual colonies were grown to log-phase in 96-well plate format and infected with VCS-M13 helper phages after which phage antibody production was allowed to proceed overnight. The supernatants containing phage antibodies were used directly in ELISA for binding to HA antigens. Alternatively, phage antibodies were PEG/NaCl-precipitated and filter-sterilized for both ELISA and flow cytometry analysis (usually done with clones which are positive in ELISA).

Example 3

Validation of the HA Specific Single-Chain Phage Antibodies

Selected supernatants containing single-chain phage antibodies that were obtained in the screenings described above were validated in ELISA for specificity, i.e., binding to different HA antigens. For this purpose, baculovirus-expressed recombinant influenza B HA (B/Ohio/01/2005, B/Malaysia/2506/2004, B/Jilin/20/2003, B/Brisbane/60/2008 and B/Florida/04/2006) (Protein Sciences, Conn., USA) was coated (0.5 µg/ml) to MAXISORP™ ELISA plates. After coating, the plates were washed three times with PBS containing 0.1% v/v TWEEN®-20 and blocked in PBS containing 2% ELK for 1 hour at room temperature. The selected single-chain phage antibodies were incubated for 1 hour in an equal volume of PBS containing 4% ELK to obtain blocked phage antibodies. The plates were emptied, washed three times with PBS/0.1% TWEEN®-20 and the blocked single-chain phage antibodies were added to the wells. Incubation was allowed to proceed for one hour; the plates were washed five times with PBS/0.1% TWEEN®-20. Bound phage antibodies were detected (using OD 492 nm measurement) using an anti-M13 antibody conjugated to peroxidase. As a control, the procedure was performed simultaneously without single-chain phage antibody and with an unrelated negative control single-chain phage antibody.

From the selections on the different HA antigens with the immune libraries, fourteen unique single-chain phage antibodies specific for both Yamagata-like and Victoria-like influenza B HA were obtained (sc08-031, sc08-032, sc08-033, sc08-034, sc08-035, sc08-059, sc10-023, sc10-032, sc10-049, sc10-051, sc11-035, sc11-036, sc11-038 and sc11-039). See Table 4.

These fourteen phage antibodies were used for construction of fully human immunoglobulins for further characterization (see Example 4).

Example 4

Construction of Fully Human Immunoglobulin Molecules (Human Monoclonal Antibodies) from the Selected Single Chain Fvs From the selected specific single-chain phage antibodies (scFv) clones, plasmid DNA was obtained and polynucleotides were determined using standard sequencing techniques. The VH and VL gene identity of the scFvs was determined (see Table 5) using the IMGT/V-QUEST search page (Brochet, et al. (2008)).

The heavy chain variable region (VH) of the scFvs was cloned by restriction digestion (SfiI/XhoI) for expression in the IgG expression vector pIg-C911-HCgammal, which was digested with the same enzymes. The light variable region (VL) was also cloned into its IgG designated expression vector pIG-C909-Ckappa, or pIg-C910-Clambda using SalI/NotI for the insert fragment and XhoI/NotI for the target vector, as described previously in WO 2008/028946.

To remove a potential de-amidation site in one of the antibodies (CR8059), a single amino acid mutant antibody (CR8071) was generated by assembly PCR. Two overlapping PCR fragments that each contained the desired mutation were generated. These fragments were mixed in equimolar ratios and served as template in a second round PCR to obtain the full length LC sequence. Polynucleotides for all constructs were verified using standard sequencing techniques. The resulting expression constructs encoding the human IgG1 heavy and light chains were transiently expressed together in HEK293T cells. After one week, the supernatants containing human IgG1 antibodies were obtained and processed using standard purification procedures. The human IgG1 antibodies were titrated in a concentration range of between 10 to 0.003 µg/ml against influenza B HA antigen (data not shown). An unrelated antibody was included as a control antibody.

The peptide of the CDRs of both, heavy and light chain, of the selected immunoglobulin molecules is given in Table 5. The polynucleotide and peptide of the heavy and light chain variable regions are given below.

Example 5

Cross-Binding Reactivity of Anti-Influenza B IgGs

The selected anti-influenza B antibodies were used to test breadth of binding by FACS analysis. For this purpose, full-length recombinant influenza B expression vectors coding for HA (B/Mississippi/04/2008, B/Houston/B60/1997, B/Nashville/45/1991, B/Florida/01/2009, B/Mississippi/07/2008 and B/Ohio/01/2005) were transfected into PER.C6® cells using lipofectamin (Invitrogen) in a 1 to 5 ratio. Forty-eight hours after transfection, the PER.C6® cells expressing the Influenza B HA on the surface were analyzed by FACS (Cantoll, BD bioscience). Hereto the cells were incubated with IgG antibodies for 1 hour followed by three sequential wash steps with PBS containing 0.1% BSA. Bound antibodies were detected using a PE-conjugated secondary anti-human antibody which was also incubated for 1 hour. As a negative control, untransfected PER.C6® cells were used and incubated with the secondary antibody. The FACS results showed that the influenza B binding antibodies CR8033, CR8059, CR8071, CR10032 and CR10051 showed binding to all six tested influenza B HAs (Table 6).

Example 6

Competition for Binding to HA of Cross-Reactive Anti-Influenza B IgGs

The anti-influenza B IgG antibodies described above were validated for competition for epitopes on influenza B HA. Hereto, B/Brisbane/60/2008, B/Florida/04/2006 and B/Jillin/20/2003 were labeled with biotin using the EZ-link Sulpho-NHS-LC-LC-biotin kit (Pierce). 1 µl of the 10 mM biotin solution was added to 110 µg of recombinant HA, which is a six-fold molar excess of biotin, and incubated for 30 to 40 minutes at room temperature. The free unincorporated biotin was removed using an Amicon Ultra centrifugal filter (0.5 ml, 10 K Ultracel-10 K membrane; Millipore, cat#: UFC501096). Hereto the sample (300 µA) was loaded on the column and spun for 10 minutes at 14000 RPM in an Eppendorf tabletop centrifuge (20800 rcf). The flow trough was discarded and 0.4 ml DPBS buffer was loaded on the column and spun again. This step was repeated two times. The labeled sample was recovered by turning the column upside down into a new collector tube; then 200 µA DPBS was loaded and spun for 1 minute at 1000 rpm in a table top centrifuge. The HA concentration was measured using a Nanodrop ND-1000 apparatus (Thermo Scientific).

The actual competition experiment was done on an Octet-QK bio-layer interferometry instrument (ForteBio) according to the settings in Table 7 using streptavidin-coated biosensors (ForteBio, cat#18-5019) that were pre-wetted for 30 minutes in kinetic buffer at room temperature. When the second antibody was able to bind the Influenza B HA in the presence of the first, this was considered as non-competing (see Table 8). As controls, stem-binding antibody CR9114 (as described in co-pending application EP11173953.8) and non-binding antibody CR8057 (as described in WO2010/130636) were used.

Antibodies CR10023 and CR10049 compete for binding CR8033. Antibodies CR10032 and CR10051 compete for binding with CR8059. Antibody CR10049 competes for binding with CR10032. None of the tested antibodies compete with stem-binding antibody CR9114. These results indicate the presence of at least three to four different epitopes on the influenza B HA (FIG. 1).

Example 7

Cross-Neutralizing Activity of IgGs

In order to determine whether the selected IgGs were capable of blocking multiple influenza B strains, in vitro virus neutralization assays (VNAs) were performed. The VNAs were performed on MDCK cells (ATCC CCL-34) that were cultured in MDCK cell culture medium (MEM medium supplemented with 20 mM Hepes and 0.15% (w/v) sodium bicarbonate (complete MEM medium), supplemented with 10% (v/v) fetal bovine serum). The influenza B Yamagata-like (B/Harbin/7/1994 and B/Florida/04/2006) and Victoria-like (B/Malaysia/2506/2004 and B/Brisbane/60/2008) strains used in the assay were all diluted to a titer of $5.7 \times 10^3$ TCID50/ml (50% tissue culture infective dose per ml), with the titer calculated according to the method of Spearman and Karber. The IgG preparations (100 µg/ml) were serially two-fold diluted (1:2 to 1:512) in complete MEM medium in quadruplicate wells. 50 µl of the respective IgG dilution was mixed with 50 µl of virus suspension (100 TCID50/35 µl) and incubated for one hour at 37° C. The suspension was then transferred in quadruplicate into 96-well plates containing confluent MDCK cultures in 100 µl complete MEM medium. Prior to use, MDCK cells were seeded at $2 \times 10^4$ cells per well in MDCK cell culture medium, grown until cells had reached confluence, washed with 300 to 350 µl PBS, pH 7.4 and finally 100 µl complete MEM medium was added to each well. The inoculated cells were cultured for three to four days at 37° C. and observed daily for the development of cytopathogenic effect (CPE). CPE was compared to the positive control.

CR8032, CR8033, CR8034, CR8035, CR8059, CR8071, CR10023, CR10032, CR10049, CR10051, CR11035, CR11036, CR11038 and CR11039 all showed cross-neutralizing activity to representative strains of both, Yamagata and Victoria-like influenza B virus strains. See Table 9.

Example 8

Receptor Binding Blocking Activity of IgGs

In order to determine whether the selected IgGs were capable of blocking the receptor mediated binding of influenza B strains to host cells, hemagglutination inhibition (HI) assays were performed. The influenza B Yamagata-like (B/Harbin/7/1994 and B/Florida/04/2006) and Victoria-like (B/Malaysia/2506/2004 and B/Brisbane/60/2008) virus strains were diluted to 8 HA units, as determined in an HAU assay, and combined with an equal volume of serially diluted IgG and incubated for 1 hour at room temperature. An equal volume of 0.5% Turkey red blood cells (TRBC) was added to the wells and incubation continued for 30 minutes. Button formation was scored as evidence of hemagglutination.

CR8059, CR8071, CR10032, CR10051 and CR11036 did not show HI activity to any of the tested influenza B virus strains (>10 µg/ml for CR11036, >50 µg/ml for the other antibodies), indicating that they do not block the receptor binding. Antibodies CR8033 and CR10023 show HI activity to representative strains of only the Yamagata-, but not the Victoria-like influenza B virus strains. Antibody CR11035 shows HI activity to a representative strain of only the Victoria-, but not the Yamagata-like influenza B virus strains. Antibodies CR10049, CR11038 and CR11039 show HI activity to representative strains of both Yamagata and Victoria-like influenza B virus strains. See Table 10.

Figure 2:
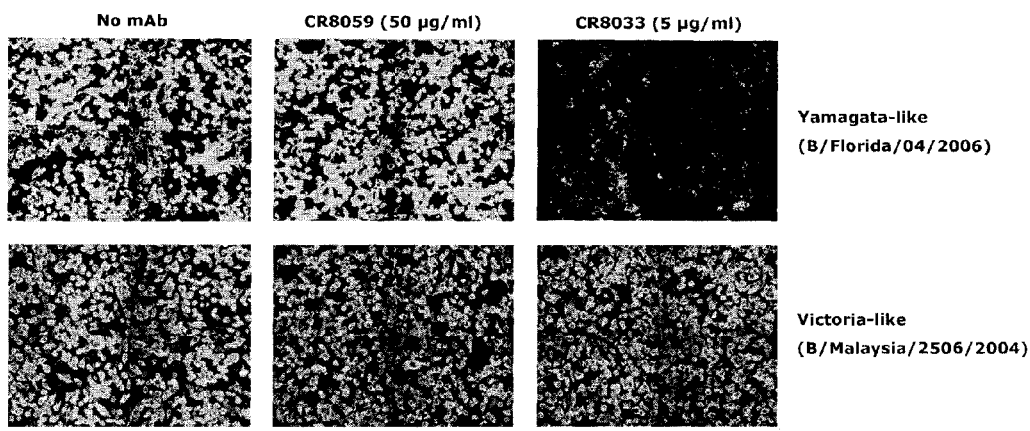
FIG. 2 shows the results of an immunofluorescence entry assay designed to analyze the ability of the binding molecules to block receptor binding and internalization of the influenza virus. A. Inhibition of viral entry by immune-fluorescence read-out; B. Infection of MDCK cells with B/Florida/04/2006.
Figure 2:
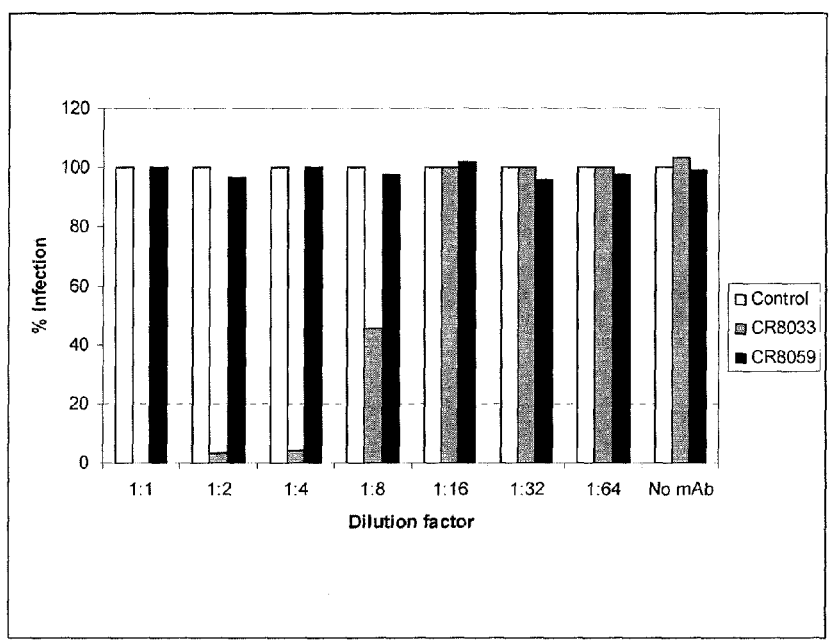

Alternatively, an immunofluorescence entry assay was designed to analyze the ability of a given antibody to block receptor binding and internalization of the virus. Therefore, the virus was pre-incubated with the antibody in serial, two-fold dilution steps before being added to a confluent monolayer of MDCK cells plated in a 96-well dish in infection medium (DMEM+200 mM glutamine) for two to three hours. The inoculum was subsequently removed and replaced with antibody at indicated concentrations for 16 to 18 hours at 37° C., 5% CO2. After this time, the supernatants were removed and the plates were fixed in 80% acetone for subsequent immunofluorescence detection by labeling infected cells using a mouse monoclonal anti-NP primary antibody (Santa Cruz, sc-52027) and an Alexa488-coupled anti-mouse secondary antibody (Invitrogen A11017) followed by DAPI labeling of cellular nuclei (see FIG. 2a). As was seen with the HI assay, antibody CR8033 specifically blocked the viral entry of Yamagata-like virus B/Florida/04/2006 but not Victoria-like virus B/Malaysia/2506/2004. Antibody CR8059 did not block the entry of the tested influenza B viruses. Some of the plates were subsequently analyzed using a BD Pathway 855 bioimager. To assess the level of entry inhibition, the fluorescence intensities per given well above a defined background and amount of infected cells (using DAPI stain to define a cell) was analyzed using BD Pathway imaging analysis tools. The percentage of infected cells treated with indicated dilutions of antibody compared to infected cells treated with a non-binding control antibody is displayed in FIG. 2b.

Example 9

Egress Inhibition of Anti-HA IgGs

To investigate the mechanism of action of the antibody, an egress assay was designed to analyze the amount of virus particles released into the supernatant 18 hours post-infection under antibody treatment conditions. The detection (or absence) of an anti-HA signal after gel electrophoresis followed by Western blot of such supernatants is taken as indication for the presence (or absence) of released virus particles.

Figure 3:
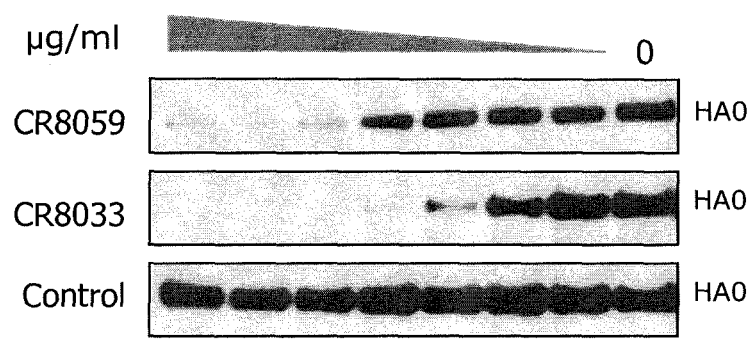
FIG. 3 shows inhibition of viral egress by the binding molecule.

Four hours prior to the experiment, 40,000 MDCK cells per well were seeded in DMEM/glutamine into 96-well plates. The amount of virus needed to achieve 90 to 100% infection was titrated in a separate experiment. The required amount of virus was added to the cells and incubated at 37° C., 5% $CO_2$. After three hours, the supernatants were removed and cells were washed thrice with PBS to remove non-internalized virus particles. Cells were replenished with infection medium containing mAbs (serial dilution starting at 20 µg/ml). After 16 to 18 hours at 37° C., 5% $CO_2$, the supernatants were harvested and the remaining cells were lysed (Tris HCl pH 7.5, 150 mM NaCl, 5 mM EDTA, 1% (v/v) TRITON®-X). Samples were subjected to SDS-PAGE/Western blot to analyze the amount of virions released into the supernatant measured by developing the WB using a rabbit polyclonal anti-HA staining (Protein Sciences) followed by an HRP-coupled anti-rabbit F(ab')$_2$-fragment (Jackson Immuno Research Laboratories, 111-036-047). As shown in FIG. 3, both antibodies CR8033 and CR8059 inhibit the release of viral particles in a concentration dependent manner. Further experiments have shown that at least CR8071 and CR10051 also inhibit the release of viral particles.

Proper infection of the cells was checked by fixing identically treated wells with 80% acetone. The amount of infection was assessed using immunofluorescence labeling using a mouse monoclononal anti-NP primary antibody (Santa Cruz, sc-52027) and an Alexa488-coupled anti-mouse secondary antibody (Invitrogen A11017). The plates were subsequently analyzed using a BD Pathway 855 bioimager (results not shown).

Example 10

Scanning Electron Microscopy of Influenza B Infected Cells

MDCK cells were seeded on glass coverslips one day prior to the experiment. The next day, cells were infected with different amounts of virus to determine the amount that yielded 90 to 100% infected cells after 18 hours post-infection. Three hours after the initial infection, the supernatants were removed; cells were washed thrice with PBS, before media containing the indicated concentration of antibodies were added. After an additional 15 to 18 hours, the cell culture medium was removed and cells were fixed in 2.5% glutaraldehyde buffer and stored at 4° C. until further analysis. The samples were subjected to further chemical fixation using glutaraldehyde (GA) and/or osmium tetroxid (OsO4). Prior to SEM imaging, the specimens were subjected to acetone dehydration and critical-point-drying. Finally, the cells were be mounted on alumina stubs and coated with thin layer of carbon and examined in a Zeiss Ultra 55 SEM microscope.

Figure 4:
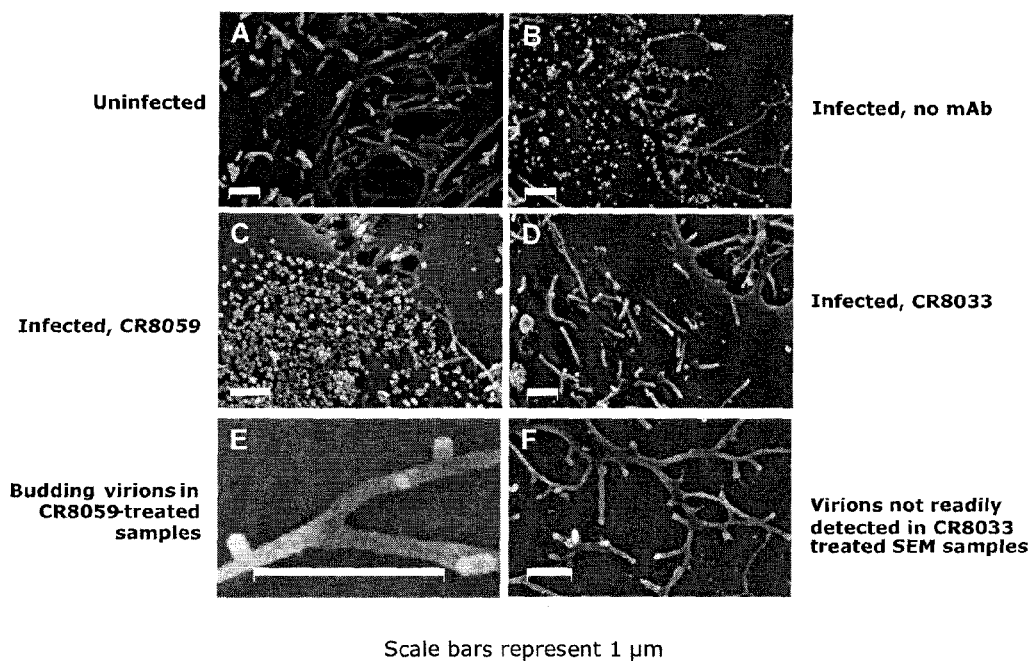
FIG. 4 shows the results of scanning EM of influenza B infected cells.

The surface of influenza B infected MDCK cells is covered with electron dense spherical particles (FIG. 4b), in contrast to uninfected controls (FIG. 4a). Incubation with antibody CR8059 does not prevent the formation of these spherical particles (FIG. 4c) whereas incubation with antibody CR8033 greatly diminishes the formation of particles (FIG. 4d). In contrast to CR8059 incubated cells, budding virions cannot readily be detected on CR8033 incubated cells (FIGS. 4e and f).

Example 11

Figure 5:
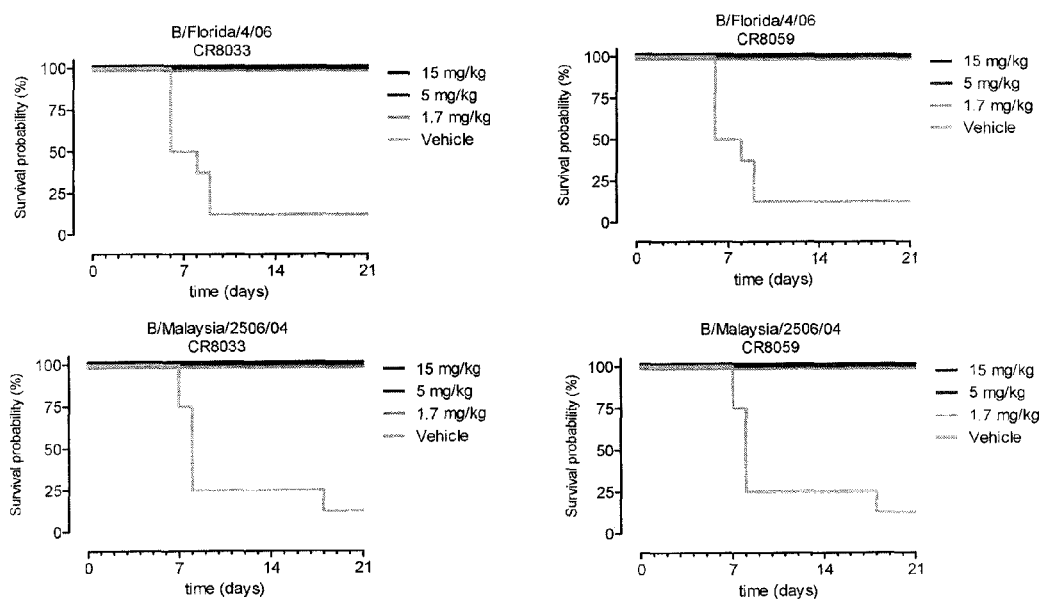
FIG. 5 shows in vivo protection by CR8033 against lethal influenza B infection (B/Florida/04/2006 and B/Malaysia/2506/2004) in mice.

Prophylactic Activity of Human IgG Monoclonal Antibodies Against Lethal Influenza B Challenge In Vivo A study was performed to test the prophylactic effect of the monoclonal antibodies CR8033 and CR8071 against a lethal challenge with two influenza B viruses in vivo. MAbs CR8033 and CR8071 were tested for prophylactic efficacy in a mouse lethal challenge model with mouse-adapted influenza B/Florida/04/2006 virus. The B/Florida/04/2006 virus was adapted to mice after five lung-to-lung passages. The mouse-adapted influenza B passage 5 virus was propagated in embryonated chicken eggs. All mice (Balb/c, female, age 6 to 8 weeks, n=8 per group) were acclimatized and maintained for a period of at least four days prior to the start of the experiment. MAbs CR8033 and CR8071 were dosed at 0.06, 0.2, 0.6, 1.7, and 5 mg/kg intravenously into the tail vein (vena coccygeus) at day −1 before challenge, assuming an average weight of 18 g per mouse and a fixed dose volume of 0.2 ml. A control group was taken along dosed with vehicle control. The mice were then challenged at day 0 with 25 $LD_{50}$ mouse-adapted B/Florida/04/2006 influenza B virus by intranasal inoculation. FIG. 5 shows the survival rates of the mice, following mAb administration. Mice dosed with dosages as low as 0.2 mg/kg for CR8033 and 0.6 mg/kg for CR8071 showed significantly higher survival rates than the vehicle treated control animals.

Alternatively, mAbs CR8033 and CR8071 were tested for prophylactic efficacy in a mouse lethal challenge model with mouse-adapted influenza B/Malaysia/2506/2004 virus. The B/Malaysia/2506/2004 virus was adapted to mice after four lung-to-lung passages. The mouse-adapted influenza B passage 4 virus was propagated in embryonated chicken eggs. All mice (Balb/c, female, age 6 to 8 weeks, n=8 per group) were acclimatized and maintained for a period of at least four days prior to the start of the experiment. MAbs CR8033 and CR8071 were dosed at 0.06, 0.2, 0.6, 1.7 and 5 mg/kg intravenously in the tail vein (vena coccygeus) at day −1 before challenge, assuming an average weight of 18 g per mouse and a fixed dose volume of 0.2 ml. A control group was taken along dosed with vehicle control. The mice were then challenged at day 0 with 25 $LD_{50}$ mouse-adapted B/Malaysia/2506/2004 influenza B virus by intranasal inoculation. FIG. 5 shows the survival rates of the mice, following mAb administration. Mice dosed with dosages as low as 0.2 mg/kg for CR8033 and 0.6 mg/kg for CR8071 showed significantly higher survival rates than the vehicle treated control animals.

These results show that human anti-influenza antibodies CR8033 and CR8071, identified and developed as disclosed herein, are able to provide in vivo protection against a lethal dose of influenza B viruses of both the B/Yamagata and the B/Victoria lineages when administered one day prior to infection at a dose equal to or higher than 0.2 or 0.6 mg/kg, respectively.

TABLE 1

Second round VL regions amplification overview

| TEMPLATE | 5' PRIMER | 3' PRIMER | PRODUCT | SHARE IN PK/PL (%) | POOL | SHARE IN VL (%) |
|---|---|---|---|---|---|---|
| K1 | OK1S | OJK1 | K1J1 | 25 | PK1 | 30 |
|  | OK1S | OJK2 | K1J2 | 25 |  |  |
|  | OK1S | OJK3 | K1J3 | 10 |  |  |
|  | OK1S | OJK4 | K1J4 | 25 |  |  |
|  | OK1S | OJK5 | K1J5 | 15 |  |  |
| K2 | OK2S | OJK1 | K2J1 | 25 | PK2 | 4 |
|  | OK2S | OJK2 | K2J2 | 25 |  |  |
|  | OK2S | OJK3 | K2J3 | 10 |  |  |
|  | OK2S | OJK4 | K2J4 | 25 |  |  |
|  | OK2S | OJK5 | K2J5 | 15 |  |  |
| K3 | OK3S | OJK1 | K3J1 | 25 | PK3 | 1 |
|  | OK3S | OJK2 | K3J2 | 25 |  |  |
|  | OK3S | OJK3 | K3J3 | 10 |  |  |
|  | OK3S | OJK4 | K3J4 | 25 |  |  |
|  | OK3S | OJK5 | K3J5 | 15 |  |  |
| K4 | OK4S | OJK1 | K4J1 | 25 | PK4 | 19 |
|  | OK4S | OJK2 | K4J2 | 25 |  |  |
|  | OK4S | OJK3 | K4J3 | 10 |  |  |
|  | OK4S | OJK4 | K4J4 | 25 |  |  |
|  | OK4S | OJK5 | K4J5 | 15 |  |  |
| K5 | OK5S | OJK1 | K5J1 | 25 | PK5 | 1 |
|  | OK5S | OJK2 | K5J2 | 25 |  |  |
|  | OK5S | OJK3 | K5J3 | 10 |  |  |
|  | OK5S | OJK4 | K5J4 | 25 |  |  |
|  | OK5S | OJK5 | K5J5 | 15 |  |  |
| K6 | OK6S | OJK1 | K6J1 | 25 | PK6 | 5 |
|  | OK6S | OJK2 | K6J2 | 25 |  |  |
|  | OK6S | OJK3 | K6J3 | 10 |  |  |
|  | OK6S | OJK4 | K6J4 | 25 |  |  |
|  | OK6S | OJK5 | K6J5 | 15 |  |  |
| L1 | OL1S | OJL1 | L1J1 | 30 | PL1 | 14 |
|  | OL1S | OJL2 | L1J2 | 60 |  |  |
|  | OL1S | OJL3 | L1J3 | 10 |  |  |

TABLE 1-continued

Second round VL regions amplification overview

| TEMPLATE | 5' PRIMER | 3' PRIMER | PRODUCT | SHARE IN PK/PL (%) | POOL | SHARE IN VL (%) |
|---|---|---|---|---|---|---|
| L2 | OL2S | OJL1 | L2J1 | 30 | PL2 | 10 |
|  | OL2S | OJL2 | L2J2 | 60 |  |  |
|  | OL2S | OJL3 | L2J3 | 10 |  |  |
| L3 | OL3S | OJL1 | L3J1 | 30 | PL3 | 10 |
|  | OL3S | OJL2 | L3J2 | 60 |  |  |
|  | OL3S | OJL3 | L3J3 | 10 |  |  |
| L4 | OL4S | OJL1 | L4J1 | 30 | PL4 | 1 |
|  | OL4S | OJL2 | L4J2 | 60 |  |  |
|  | OL4S | OJL3 | L4J3 | 10 |  |  |
| L5 | OL5S | OJL1 | L5J1 | 30 | PL5 | 1 |
|  | OL5S | OJL2 | L5J2 | 60 |  |  |
|  | OL5S | OJL3 | L5J3 | 10 |  |  |
| L6 | OL6S | OJL1 | L6J1 | 30 | PL6 | 1 |
|  | OL6S | OJL2 | L632 | 60 |  |  |
|  | OL6S | OJL3 | L6J3 | 10 |  |  |
| L7 | OL7S | OJL1 | L7J1 | 30 | PL7 | 1 |
|  | OL7S | OJL2 | L7J2 | 60 |  |  |
|  | OL7S | OJL3 | L7J3 | 10 |  |  |
| L8 | OL8S | OJL1 | L8J1 | 30 | PL8 | 1 |
|  | OL8S | OJL2 | L8J2 | 60 |  |  |
|  | OL8S | OJL3 | L8J3 | 10 |  |  |
| L9 | OL9S | OJL1 | L9J1 | 30 | PL9 | 1 |
|  | OL9S | OJL2 | L9J2 | 60 |  |  |
|  | OL9S | OJL3 | L9J3 | 10 |  |  |
|  |  |  |  |  | VL | 100% |

TABLE 2

Second round VH regions amplification overview

| TEMPLATE | 5' PRIMER | 3' PRIMER | PRODUCT | SHARE IN PK/PL (%) | POOL | SHARE IN VH (%) |
|---|---|---|---|---|---|---|
| H1 | OH1S | OJH1 | H1J1 | 10 | PH1 | 25 |
|  | OH1S | OJH2 | H1J2 | 10 |  |  |
|  | OH1S | OJH3 | H1J3 | 60 |  |  |
|  | OH1S | OJH4 | H1J4 | 20 |  |  |
| H2 | OH2S | OJH1 | H2J1 | 10 | PH2 | 2 |
|  | OH2S | OJH2 | H2J2 | 10 |  |  |
|  | OH2S | OJH3 | H2J3 | 60 |  |  |
|  | OH2S | OJH4 | H2J4 | 20 |  |  |
| H3 | OH3S | OJH1 | H3J1 | 10 | PH3 | 25 |
|  | OH3S | OJH2 | H3J2 | 10 |  |  |
|  | OH3S | OJH3 | H3J3 | 60 |  |  |
|  | OH3S | OJH4 | H3J4 | 20 |  |  |
| H4 | OH4S | OJH1 | H4J1 | 10 | PH4 | 25 |
|  | OH4S | OJH2 | H4J2 | 10 |  |  |
|  | OH4S | OJH3 | H4J3 | 60 |  |  |
|  | OH4S | OJH4 | H4J4 | 20 |  |  |
| H5 | OH5S | OJH1 | H5J1 | 10 | PH5 | 2 |
|  | OH5S | OJH2 | H5J2 | 10 |  |  |
|  | OH5S | OJH3 | H5J3 | 60 |  |  |
|  | OH5S | OJH4 | H5J4 | 20 |  |  |
| H6 | OH6S | OJH1 | H6J1 | 10 | PH6 | 20 |
|  | OH6S | OJH2 | H6J2 | 10 |  |  |
|  | OH6S | OJH3 | H6J3 | 60 |  |  |
|  | OH6S | OJH4 | H6J4 | 20 |  |  |
| H7 | OH7S | OJH1 | H7J1 | 10 | PH7 | 1 |
|  | OH7S | OJH2 | H7J2 | 10 |  |  |
|  | OH7S | OJH3 | H7J3 | 60 |  |  |
|  | OH7S | OJH4 | H7J4 | 20 |  |  |
|  |  |  |  |  | VH | 100% |

TABLE 3

Characteristics of the individual IgM memory B cell libraries.

| Library | Cells Used | Library size | Intact Orf |
|---|---|---|---|
| MEM-05-M08 | 540,000 IgM memory cells Facs sorted from 1 donor | 5.9E+07 |  |
| MEM-05-M09 | 775,000 IgM memory cells Facs sorted from 1 donor | 2.35E+07 |  |
| MEM-05-M10 | 700,000 IgM memory cells Facs sorted from 1 donor | 1.7E+07 |  |
| Flu-PBMC-09-M02 | 1E+07 total PBMCs from 1 donor | 1.0E+07 | 75% |
| Flu-Bcell-09-M03 | 280,000 Macs sorted B cells from 1 donor | 2.0E+07 | 76% |
| Flu-MEM-09-M08 | 800,000 IgM memory cells Facs sorted from 1 donor | 2.4E+07 | 85% |
| Flu-PBMC-10-M03 | 3E+07 total PBMCs from 3 donors (1E+07 PBMCs per donor) | 2.8E+07 | 82% |
| Flu-PBMC-10-M04 | 3E+07 total PBMCs from 3 donors (1E+07 PBMCs per donor) | 3.1E+07 | 87% |
| Flu-PBMC-10-M05 | 3E+07 total PBMCs from 3 donors (1E+07 PBMCs per donor) | 3.3E+07 | 89% |
| Flu-PBMC-11-G01 | 4E+07 total PBMCs from 4 donors (1E+07 PBMCs per donor) | >1E+07 | 82% |

TABLE 4

Binding of scFv-phages to recombinant Influenza B HA

| | Yamagata | | Victoria | | |
|---|---|---|---|---|---|
| | B/Jilin/ 20/03 | B/Florida/ 04/06 | B/Malaysia/ 2506/04 | B/ohio/ 01/05 | B/Brisbane/60/08 |
| sc08-031 | ++ | nt | ++ | ++ | nt |
| sc08-032 | ++ | nt | ++ | ++ | nt |
| sc08-033 | ++ | ++ | ++ | +++ | ++ |
| sc08-034 | ++ | nt | ++ | ++ | nt |
| sc08-035 | ++ | nt | ++ | ++ | nt |
| sc08-059 | ++ | ++ | ++ | ++ | ++ |
| sc10-023 | ++ | ++ | + | ++ | + |
| sc10-032 | +++ | +++ | ++ | +++ | +++ |
| sc10-049 | +++ | +++ | +++ | +++ | +++ |
| sc10-051 | +++ | +++ | +++ | +++ | +++ |
| se11-035 | nt | +++ | nt | ++ | ++ |
| se11-036 | nt | +++ | nt | +++ | +++ |
| sc11-038 | nt | ++ | nt | ++ | +++ |
| se11-039 | nt | +++ | nt | ++ | +++ |

+++ strong binding
++ binding weak
+ binding
— no binding
nt not tested

TABLE 5A

Peptides of HC CDRs of selected antibodies

| CR # | VH locus | CDR1-HC (SEQ ID NO) | CDR2-HC (SEQ ID NO) | CDR3-HC (SEQ ID NO) |
|---|---|---|---|---|
| CR8033 | IGHV3-9*01 | GFSFDEYT (1) | INWKGNFM (2) | AKDRLESSAMDILEGGTFDI (3) |
| CR8059 | IGHV1-18*01 | GYIFTESG (7) | ISGYSGDT (8) | ARDVQYSGSYLGAYYFDY (9) |
| CR8071 | IGHV1-18*01 | GYIFTESG (7) | ISGYSGDT (8) | ARDVQYSGSYLGAYYFDY (9) |
| CR10023 | IGHV3-9*01 | GFTFDDYA (14) | INWVSTTM (15) | AKDRLESAAIDILEGGTFDI (16) |
| CR10032 | IGHV4-39*02 | GGSINSSPYK (20) | FYYDGST (21) | AAYCSSISCHAYYDYMNV (22) |
| CR10049 | IGHV3-23*04 | GFTFSSYA (26) | LSDESTT (27) | AEDLGTVMDSYYYGMNV (28) |
| CR10051 | IGHV1-46*01 | GDTFTNYH (31) | INPISGDT (32) | ATDESPGLLTGLRDYWYYYGMDV (33) |
| CR11024 | IGHV1-2*02 | GYSFTGYY (35) | INPISGDT (36) | ARVAGEDWFGDLDY (37) |
| CR11035 | IGHV1-18*01 | GYAFNGYG (40) | INTYKVNT (41) | ARDWGGPFGNAFDF (42) |
| CR11036 | IGHV1-46*01 | GYAFTSYY (45) | MNLHGGST (46) | ARESPDSSGYPGYYGMDV (47) |
| CR11038 | IGHV1-46*01 | GYAFTSYY (45) | IVINPHGGST (50) | ARESPDSSGYPGYYGMDV (47) |
| CR11039 | GHV1-18*01 | GYAFTGYG (54) | INTYKFNT (55) | ARDWAGPFGNAFDV (56) |
| CR08031 | IGHV3-9*01 | GFTFDEYI (59) | INWKGNFM (2) | AKDRLESSAMDILEGGTFDI (3) |
| CR08032 | IGHV3-9*01 | GFSFDEYI (61) | INWKGNFM (2) | AKDRLESSAMDILEGGTFDI (3) |
| CR08034 | IGHV3-9*01 | GFTFDEYI (59) | INWKGNFM (2) | AKDRLESSAMDILEGGTFDI (3) |
| CR08035 | IGHV3-9*01 | GFTFDEYI (59) | INWKGNFM (2) | AKDRLESSAMDILEGGTFDI (3) |

TABLE 5B

Peptides of LC CDRs of selected antibodies

| CR # | VL locus | CDR1-LC (SEQ ID NO) | CDR2-LC (SEQ ID NO) | CDR3-LC (SEQ ID NO) |
|---|---|---|---|---|
| CR8033 | IGKV3-20*01 | QSVSSSY (4) | GAS (5) | QQYGSSPWT (6) |
| CR8059 | IGLV1-47*01 | SSNIGTNY (10) | RSY (11) | ATWDDSLNGWV (12) |
| CR8071 | IGLV1-47*01 | SSNIGTNY (10) | RSY (11) | ATWDDSLDGWV (13) |
| CR10023 | IGLV2-8*01 | SSDVGGYNY (17) | DVS (18) | SSYASGSTYV (19) |
| CR10032 | IGKV2-28*01 | QSLRHENGYNY (23) | LGS (24) | MQALTQTLT (25) |
| CR10049 | IGKV2-28*01 | QSLLHSNGLNY (29) | LGS (24) | MQALQTPFT (30) |
| CR10051 | IGKV3-20*01 | QSVSSSY (4) | GAS (5) | QQYGSSPLCS (34) |
| CR11024 | IGKV3-20*01 | QSVSSSY (4) | GTS (38) | QQYGSSPRT (39) |
| CR11035 | IGKV1-39*01 | QSVGSY (43) | GAS (5) | QQSYSTPRT (44) |
| CR11036 | IGKV3-20*01 | QSVSSDF (48) | GTS (38) | QQYGSSTWT (49) |
| CR11038 | IGLV1-44*01 | RSNIGSNP (51) | TND (52) | AAWDDSLKGWV (53) |
| CR11039 | GHV1-18*01 | QDISDY (57) | GAS (5) | QQYGNLPPT (58) |
| CR08031 | IGLV2-14*01 | SSDVGGYNY (17) | DVS (18) | SSYTSSSTHV (60) |
| CR08032 | IGLV2-14*01 | RRDVGDYKY (62) | DVS (18) | SSYTTSNTRV (63) |
| CR08034 | IGKV1-17*01 | QGIRND (64) | AAS (65) | QQANTYPLT (66) |
| CR08035 | IGLV3-19*01 | SLRSYY (67) | GKN (68) | DSRDSSGTHYV (69) |

TABLE 6

Binding of purified IgG to cell expressed Influenza B HA

| | Yamagata | | | Victoria | | |
|---|---|---|---|---|---|---|
| | Nashville/ 45/91 | Mississippi/ 04/08 | Houston/ B0/97 | Mississippi/ 07/08 | Florida/ 01/09 | Ohio/ 01/05 |
| CR8031 | ++ | NT | NT | NT | — | NT |
| CR8032 | +++ | + | NT | ++ | — | NT |
| CR8033 | ++ | ++ | ++ | ++ | ++ | ++ |
| CR8034 | ++ | NT | NT | NT | — | NT |
| CR8035 | +++ | + | +++ | + | — | ++ |
| CR8059 | +++ | +++ | +++ | +++ | +++ | +++ |
| CR8071 | +++ | +++ | +++ | +++ | +++ | +++ |
| CR10023 | +++ | — | +++ | — | — | — |
| CR10032 | +++ | +++ | +++ | +++ | +++ | +++ |
| CR10049 | + | — | + | — | — | + |
| CR10051 | ++ | ++ | ++ | ++ | ++ | ++ |

+++ strong binding
++ binding
+ weak binding
— no binding

TABLE 7

Plate layout octet competition experiment

| | Step | | | | |
|---|---|---|---|---|---|
| | Base line 1 | Loading HA | Baseline 2 | Association 1st IgG (15 µg/ml) | Association/ competition 2nd IgG (15 µg/ml) |
| Duration (seconds) | 60 | 1200 | 60 | 700 | 700 |
| Row A | Kinetic buffer | A Biotine labeled influenza B HA 10 ug/ml | Kinetic buffer | CR8033 | CR8033 |
| Row B | | | | CR8059 | In 2nd |
| Row C | | | | CR10023 | measurement |
| Row D | | | | CR10032 | CR8059 etc. |
| Row E | | | | CR10049 | |
| Row F | | | | CR10051 | |
| Row G | | | | CR9114* | |
| Row I | | | | CR8057* | |

*control antibodies (CR9114: binding, CR8057 non-binding)

TABLE 8

Competition experiment on influenza B HA

|  | CR8033 | CR8059 | CR10023 | CR10032 | CR10049 | CR10051 | CR9114 | CR8057 |
|---|---|---|---|---|---|---|---|---|
| CR8033 | X | N | Y | N | Y | N | N | N |
| CR8059 | N | X | N | Y | N | Y | N | N |
| CR10023 | Y | N | X | Y | Y | N | N | N |
| CR10032 | N | Y | Y | X | Y | Y | N | N |
| CR10049 | Y | N | Y | N | X | N | N | N |
| CR10051 | N | Y | N | Y | N | X | N | N |
| CR9114 | N | N | N | N | N | N | X | N |
| CR8057 | — | — | — | — | — | — | — | — |

Y: competition;
N: no competition;
X: self-competition;
—: No binding

TABLE 9

Virus neutralization assays on influenza B virus strains

| VNA titers in µg/ml | Yamagata | | Victoria | |
|---|---|---|---|---|
| | B/Harbin/ 7/1994 | B/Florida/ 04/2006 | B/Malaysia/ 2506/2004 | B/Brisbane/ 60/2008 |
| CR8031 | 1.24 | 0.88 | >50* | NT |
| CR8032 | 0.69 | 0.69 | 3.88* | NT |
| CR8033 | 0.03 | 0.02 | 0.88* | 5.95 |
| CR8034 | 0.29 | 0.12 | 2.31* | NT |
| CR8035 | 0.66 | 0.66 | 4.46* | NT |
| CR8059 | 2.39 | 3.23 | 17.68* | 4.55 |
| CR8071 | 2.34 | 2.12 | 14.87* | 3.72 |
| CR10023 | 0.26 | ≤0.55 | 12.5* | 7.07 |
| CR10032 | 12.5 | 21.02 | 53.03* | 35.36 |
| CR10049 | 4.42 | 1.3 | 25* | 35.36 |
| CR10051 | 0.28 | 0.63 | 1.77* | 1.51 |
| CR11035 | 0.16 | ≤0.06 | 0.53* | 0.93 |
| CR11036 | 0.02 | ≤0.06 | 0.22* | ≤0.14 |
| CR11038 | 0.05 | ≤0.06 | 2.1* | 0.55 |
| CR11039 | 0.02 | ≤0.06 | 0.06* | ≤0.14 |

NT: not tested;
*assay was done with 25TCIDs

TABLE 10

Hemagglutination inhibition assay on influenza B virus strains

| HI titers in µg/ml | Yamagata | | Victoria | |
|---|---|---|---|---|
| | B/Harbin/ 7/1994 | B/Florida/ 04/2006 | B/Malaysia/ 2506/2004 | B/Brisbane/ 60/2008 |
| CR8033 | 0.39 | 0.22 | >50 | >50 |
| CR8059 | >50 | >50 | >50 | >50 |
| CR8071 | >50 | >50 | >50 | >50 |
| CR10023 | 1.1 | 1.56 | >50 | >50 |
| CR10032 | >50 | >50 | >50 | >50 |
| CR10049 | >50 | 1.1 | 4.42 | 35.36 |
| CR10051 | >50 | >50 | >50 | >50 |
| CR11035 | NT | >10 | NT | 0.26 |
| CR11036 | NT | >10 | NT | >10 |
| CR11038 | NT | 1.25 | NT | 0.31 |
| CR11039 | NT | 0.63 | NT | 0.44 |

NT: not tested

SEQUENCES

>SC08-033 VH DNA
(SEQ ID NO: 70)
GAGGTGCAGCTGGTGGAGACTGGGGGAGGCCTGGTACAGCCTGGCAGGTCCCTGAGACTGTCCTGT
GCAGCCTCTGGATTCAGCTTTGATGAGTACACCATGCATTGGGTCCGGCAAGCTCCAGGGAAGGGC
CTGGAGTGGGTCGCAGGTATTAATTGGAAAGGTAATTTCATGGGTTATGCGGACTCTGTCCAGGGC
CGATTCACCATCTCCAGAGACAACGGCAAGAACTCCCTCTATCTGCAAATGAACAGTCTGAGAGCT
GAGGACACGGCCTTGTATTACTGTGCAAAAGACCGGCTGGAGAGTTCAGCTATGGACATTCTAGAA
GGGGGTACTTTTGATATCTGGGGCCAAGGGACAATGGTCACC

>SC08-033 VH PROTEIN
(SEQ ID NO: 71)
EVQLVETGGGLVQPGRSLRLSCAASGFSFDEYTMHWVRQAPGKGLEWVAGINWKGNFMGYADSVQG
RFTISRDNGKNSLYLQMNSLRAEDTALYYCAKDRLESSAMDILEGGTFDIWGQGTMVT

>SC08-033 VL DNA
(SEQ ID NO: 72)
GAAATTGTGTTGACGCAGTCTCCAGGCACCCTGTCTTTGTCTCCAGGGGAAAGAGCCACCCTCTCC
TGCAGGGCCAGTCAGAGTGTTAGCAGCAGCTACTTAGCCTGGTACCAGCAGAAACCTGGCCAGGCT
CCCAGGCTCCTCATCTATGGTGCATCCACCAGGGCCACTGGTATCCCAGCCAGGTTCAGTGGCAGT

| SEQUENCES |
| --- |
| GGGTCTGGGACAGACTTCACTCTCACCATCAGCAGACTGGAGCCTGAAGATCTTGCAGTGTATTAC |
| TGTCAGCAGTATGGTAGCTCACCGTGGACGTTCGGCCAAGGGACCAAGGTGGAAATCAAAC |

>SC08-033 VL PROTEIN (SEQ ID NO: 73)

EIVLTQSPGTLSLSPGERATLSCRASQSVSSSYLAWYQQKPGQAPRLLIYGASTRATGIPARFSGS
GSGTDFTLTISRLEPEDLAVYYCQQYGSSPWTFGQGTKVEIK

>SC08-059 VH DNA (SEQ ID NO: 74)

GAGGTCCAGCTGGTACAGTCTGGAGCTGAGGTGAAGAAGCCTGGGGCCTCAGTGAGGGTCTCCTGC
AGGGCCTCTGGTTACATCTTTACCGAATCTGGTATCACCTGGGTGCGCCAGGCCCCTGGACAAGGG
CTTGAGTGGATGGGATGGATCAGCGGTTACAGTGGTGACACAAAATATGCACAGAAACTCCAGGGC
AGAGTCACCATGACCAAAGACACATCCACGACCACAGCCTACATGGAATTGAGGAGCCTGAGATAT
GACGACACGGCCGTATATTACTGTGCGAGAGACGTCCAGTACAGTGGGAGTTATTGGGCGCCTAC
TACTTTGACTATTGGAGCCCGGGAACCCTGGTCACCGTCTCGAGC

>SC08-059 VH PROTEIN (SEQ ID NO: 75)

EVQLVQSGAEVKKPGASVRVSCRASGYIFTESGITWVRQAPGQGLEWMGWISGYSGDTKYAQKLQG
RVTMTKDTSTTTAYMELRSLRYDDTAVYYCARDVQYSGSYLGAYYFDYWSPGTLVTVSS

>SC08-059 VL DNA (SEQ ID NO: 76)

TCCTATGTGCTGACTCAGCCACCCTCAGCGTCTGGGACCCCCGGGCAGAGGGTCACCATCTCTTGT
TCTGGAAGCAGCTCCAACATCGGAACTAATTATGTATACTGGTACCAGCAGTTCCCAGGAACGGCC
CCCAAACTCCTCATCTATAGGAGTTATCAGCGGCCCTCAGGGGTCCCTGACCGATTCTCTGGCTCC
AAGTCTGGCTCCTCAGCCTCCCTGGCCATCAGTGGGCTCCAGICTGAGGATGAGGCTGATTATTAC
TGTGCAACATGGGATGACAGCCTGAATGGTTGGGTGTTCGGCGGAGGGACCAAGCTGACCGTCCTA
G

>SC08-059 VL PROTEIN (SEQ ID NO: 77)

SYVLTQPPSASGTPGQRVTISCSGSSSNIGTNYVYWYQQFPGTAPKLLIYRSYQRPSGVPDRFSGS
KSGSSASLAISGLQSEDEADYYCATWDDSLNGWVFGGGTKLTVL

>CR08071 VH PROTEIN (SEQ ID NO: 78)

QVQLVQSGAEVKKPGASVRVSCRASGYIFTESGITWVRQAPGQGLEWMGWISGYSGDTKYAQKLQG
RVTMTKDTSTTTAYMELRSLRYDDTAVYYCARDVQYSGSYLGAYYFDYWSPGTLVTVSS

>CR08071 VL PROTEIN (SEQ ID NO: 79)

QSVLTQPPSASGTPGQRVTISCSGSSSNIGTNYVYWYQQFPGTAPKLLIYRSYQRPSGVPDRFSGS
KSGSSASLAISGLQSEDEADYYCATWDDSLDGWVFGGGTKLTVLRK

>SC10-051 VH DNA (SEQ ID NO: 80)

GAGGTCCAGCTGGTGCAGTCTGGAGCTGAGGTGAAGAAGCCTGGGGCCTCAGTAGAACTTTCCTGC
AAGGCATCTGGAGACACCTTCACCAACTACCATATACACTGGGTGCGACAGGCCCCTGGACAAGGG
CTTGAGTGGATGGGAATAATCAATCCTAGTGGTGGTGACACAGACTACTCACAGAAGTTCCAGGGC
AGAGTCACCCTGACCAGGGACAGGTCCACAAACACATTCTATATGAAGTTGGCCAGCCTGAGATCT
GAGGACACGGCCGTGTATTACTGTGCGACAGATGAGAGTCCCGGACTTTTGACTGGCCTTCGGGAT
TACTGGTACTACTACGGTATGGACGTCTGGGGCCAGGGGACCACGGTCACCGTCTCGAG

| SEQUENCES |
| --- |

>SC10-051 VH PROTEIN (SEQ ID NO: 81)

EVQLVQSGAEVKKPGASVELSCKASGDTFTNYHIHWVRQAPGQGLEWMGIINPSGGDTDYSQKFQG

RVTLTRDRSTNTFYMKLASLRSEDTAVYYCATDESPGLLTGLRDYWYYYGMDVWGQGTTVTVS

>SC10-051 VL DNA (SEQ ID NO: 82)

GAAATTGTGTTGACGCAGTCTCCAGGCACCCTGTCTTTGTCTCCAGGGGAAAGAGCCACCCTCTCC

TGCAGGGCCAGTCAGAGTGTTAGCAGCAGCTACTTAGCCTGGTACCAGCAGAAACCTGGCCAGGCT

CCCAGGCTCCTCATCTATGGTGCATCCAGCAGGGCCACTGGCATCCCAGACAGGTTCAGTGGCAGT

GGGTCTGGGACAGACTTCACTCTCACCATCAGCAGACTGGAGCCTGAAGATTTTGCAGTGTATTAC

TGTCAGCAGTATGGTAGCTCACCTCTGTGCAGTTTTGGCCAGGGGACCAAGCTGGAGATCAAAC

>SC10-051 VL PROTEIN (SEQ ID NO: 83)

EIVLTQSPGTLSLSPGERATLSCRASQSVSSSYLAWYQQKPGQAPRLLIYGASSRATGIPDRFSGS

GSGTDFTLTISRLEPEDFAVYYCQQYGSSPLCSFGQGTKLEIK

>SC10-049 VH DNA (SEQ ID NO: 84)

GAGGTGCAGCTGGTGGAGTCTGGGGGAGGCTTGGTACAGCCTGGGGGGTCCCTGAGACTCTCCTGT

GCAGCCTCTGGATTCACCTTTAGCAGCTATGCCATGAGCTGGGTCCGCCAGGCTCCAGGGAAGGGG

CTGGAGTGGGTCTCACGTCTTAGTGATGAAAGTACCACATACTATGCAGACTCCGTGAAGGGCCGA

TTCACTATCTCCAGAGACAATTCCAAGAACACACTGTATCTGCAGATGAACAGCCTGAAAGCCGAC

GACACGGCCATATATTACTGTGCGAGGATCTGGGGACGGTGATGGACTCCTACTACTACGGTATG

AACGTCTGGGGCCCAGGGACCACGGTCACCGTCTCGAG

>SC10-049 VH PROTEIN (SEQ ID NO: 85)

EVQLVESGGGLVQPGGSLRLSCAASGFTFSSYAMSWVRQAPGKGLEWVSRLSDESTTYYADSVKGR

FTISRDNSKNTLYLQMNSLKADDTAIYYCAEDLGTVMDSYYYGMNVWGPGTTVTVS

>SC10-049 VL DNA (SEQ ID NO: 86)

GATGTTGTGATGACTCAGTCTCCACTCTCCCTGCCCGTCACCCCTGGAGAGCCGGCCTCCATCTCC

TGCAGGTCTAGTCAGAGCCTCCTGCATAGTAATGGACTCAATTATTTGGATTGGTACCTGCAGAAG

CCAGGGCAGTCTCCACAGCTCCTGATCTATTTGGGTTCTAATCGGGCCTCCGGGGTCCCTGACAGG

TTCAGTGGCAGTGGATCAGGCACAGATTTTACACTGAAAATCAGCAGAGTGGAGGCTGAGGATGTT

GGGGTTTATTACTGCATGCAAGCTCTACAAACTCCTTTCACTTTCGGCGGAGGGACCAAGGTGGAG

ATCAAAC

>SC10-049 VH PROTEIN (SEQ ID NO: 87)

DVVMTQSPLSLPVTPGEPASISCRSSQSLLHSNGLNYLDWYLQKPGQSPQLLIYLGSNRASGVPDR

FSGSGSGTDFTLKISRVEAEDVGVYYCMQALQTPFTFGGGTKVEIK

>SC10-023 VH DNA (SEQ ID NO: 88)

GAGGTGCAGCTGGTGGAGACTGGGGGAGGCTTGGTACAGCCTGGCAGGTCCCTGAGACTCTCCTGT

GCAGCCTCTGGATTCACCTTTGATGATTATGCCATGCATTGGGTCCGGCAAGCTCCAGGGAAGGGC

CTGGAGTGGGTCTCAGGTATTAATTGGGTTAGTACTACCATGGGCTATGCGGACTCTGTGAAGGGC

CGATTCACCATCTCCAGAGACAACGCCAAGAACTCCCTGTATCTGCAAATGAACAGTCTGAGAGCT

| SEQUENCES |
|---|
| GAGGACACGGCCTTGTATTACTGTGCAAAAGATAGGCTGGAGAGTGCAGCTATAGACATTCTAGAA |
| GGGGGTACTTTTGATATCAGGGGCCAAGGGACAATGGTCACCGTCTCGAGCG |
| >SC10-023 VH PROTEIN (SEQ ID NO: 89) |
| EVQLVETGGGLVQPGRSLRLSCAASGFTFDDYAMHWVRQAPGKGLEWVSGINWVSTTMGYADSVKG |
| RFTISRDNAKNSLYLQMNSLRAEDTALYYCAKDRLESAAIDILEGGTFDIRGQGTMVTVSS |
| >SC10-023 VL DNA (SEQ ID NO: 90) |
| CAGTCTGCCCTGACTCAGCCTCCCTCCGCGTCCGGCTCTCCTGGACAGTCAGTCACCATCTCCTGC |
| ACTGGAACCAGCAGTGATGTTGGTGGTTATAACTATGTCTCCTGGTACCAACAGCACCCAGGCAAA |
| GCCCCCAAACTCATGATTTATGATGTCAGTAAGCGGCCCTCAGGGGTCCCTGATCGCTTCTCTGGG |
| TCCAAGTCTGGCAACACGGCCTCCCTGACCATCTCTGGGCTCCAGGCTGAGGACGAGGCTGAATAT |
| TACTGCAGCTCATATGCAAGCGGCAGCACTTATGTCTTCGGAACTGGGACCAAGGTCACCGTCCTA |
| G |
| >SC10-023 VL PROTEIN (SEQ ID NO: 91) |
| QSALTQPPSASGSPGQSVTISCTGTSSDVGGYNYVSWYQQHPGKAPKLMIYDVSKRPSGVPDRFSG |
| SKSGNTASLTISGLQAEDEAEYYCSSYASGSTYVFGTGTKVTVL |
| >SC10-032 VH DNA (SEQ ID NO: 92) |
| CAGGTGCAGCTGCAGGAGTCGGGCCCAGGACTGGTGAAGCCTTCGGGCACCCTGTCCCTCACCTGC |
| AATGTCTCTGGTGGCTCCATCAACAGTAGTCCCTATAAGTGGGCCTGGATCCGCCAGTCCCCAGGG |
| AAGGGGCTGGAGTGGATTGGGACTTTCTATTATGATGGGAGCACCGACTACAACCCGTCCCTCCAG |
| AGTCGACTCACCATTTCCGGAGACATGTCCAGTAACCACTTCTCCTTGAGGCTGAGGTCTGTGACC |
| GCCGCAGACACGGCTGTGTATTACTGTGCGGCCTATTGTAGTAGTATAAGCTGCCATGCCTATTAC |
| GACTACATGAACGTCTGGGGCAAAGGGACCACGGTCACCGTCTCGAGC |
| >SC10-032 VH PROTEIN (SEQ ID NO: 93) |
| QVQLQESGPGLVKPSGTLSLTCNVSGGSINSSPYKWAWIRQSPGKGLEWIGTFYYDGSTDYNPSLQ |
| SRLTISGDMSSNHFSLRLRSVTAADTAVYYCAAYCSSISCHAYYDYMNVWGKGTTVTVSS |
| >SC10-032 VL DNA (SEQ ID NO: 94) |
| GAAATTGTGCTGACTCAGTCTCCACTCTCCCTGCCCGTCACCCCTGGAGAGCCGGCCTCCATCTCC |
| TGCAGGTCTAGTCAGAGCCTCCGACATGAGAATGGATACAACTATTTGGATTGGTACCTGCAGAAG |
| CCAGGGCAGTCTCCACAGCTCCTGATGTATTTGGGTTCTGTTCGGGCCTCCGGGGTCCCTGACAGG |
| TTCAGTGGCAGTGGATCAGGCACAGATTTTACACTGAAAATCAGCAGAGTGGAGGCTGAGGATGTT |
| GGGGTTTATTACTGCATGCAAGCTCTACAAACGCTCACTTTCGGCGGAGGGACCAAGCTGGAGATC |
| AAAC |
| >SC10-032 VL PROTEIN (SEQ ID NO: 95) |
| EIVLTQSPLSLPVTPGEPASISCRSSQSLRHENGYNYLDWYLQKPGQSPQLLMYLGSVRASGVPDR |
| FSGSGSGTDFTLKISRVEAEDVGVYYCMQALQTLTFGGGTKLEIK |
| >SC11-024 VH DNA (SEQ ID NO: 96) |
| GAGGTGCAGCTGGTGCAGTCTGGGGCTGAAATTAAGAAGCCTGGGGCCTCAGTGAAGGTCTCCTGC |
| AAGGCTTCTGGATACAGCTTCACCGGCTACTATATGCACTGGGTGCGACAGGCCCCTGGACAAGGA |
| CCTGAGTGGATGGGGCGGATCAACCCTATCAGTGGTGACACAAACTATGCACAGAGGTTTCAGGGC |

| SEQUENCES |
|---|

AGGGTCACCTTGACCAGGGACAGGTCCACCAGCACAGCCTACATGGAGCTGAGCGGGCTGAAATCT

GACGACACGGCCGTATATTTCTGTGCGAGAGTCGCGGGTGAAGATTGGTTCGGGGATCTTGACTAT

TGGGGCCAGGGAACCCTGGTCACCGTCTCGAGCG

>SC11-24 VH PROTEIN
(SEQ ID NO: 97)
EVQLVQSGAEIKKPGASVKVSCKASGYSFTGYYMHWVRQAPGQGPEWMGRINPISGDTNYAQRFQG

RVTLTRDRSTSTAYMELSGLKSDDTAVYFCARVAGEDWFGDLDYWGQGTLVTVSS

>SC11-024 VL DNA
(SEQ ID NO: 98)
GAAATTGTGTTGACGCAGTCTCCAGCCACCCTGTCTGTGTCTCCAGGGGAAAGAGCCACCCTCTCC

TGCAGGGCCAGTCAGAGTGTTAGCAGCAGCTACTTAGCCTGGTACCAGCAGAAACCTGGCCAGGCT

CCCAGGCTCCTCATCTTTGGAACATCCAGCAGGGCCACTGGCATCCCAGACAGGTTCAGTGGCAGT

GGGTCTGGGACAGACTTCACTCTCACCATCAGCAGGCTGGAGCCTGAAGATTTTGCAGTGTATTAC

TGTCAGCAGTATGGTAGCTCACCTCGGACGTTCGGCCAAGGGACCAAGGTGGAGATCAAAC

>SC11-024 VL PROTEIN
(SEQ ID NO: 99)
EIVLTQSPATLSVSPGERATLSCRASQSVSSSYLAWYQQKPGQAPRLLIFGTSSRATGIPDRFSGS

GSGTDFTLTISRLEPEDFAVYYCQQYGSSPRTFGQGTKVEIK

>SC11-035 VH DNA
(SEQ ID NO: 100)
CAGGTGCAGCTGGTACAGTCTGGAGCTGAGGTGAAGAAGCCTGGGTCCTCGGTGAAGGTCTCCTGC

AAGACCTCTGGTTACGCCTTTAACGGCTACGGTATCAGCTGGGTGCGACAGGCCCCTGGACAAGGG

CTTGAGTGGGTGGCATGGATCAACACTTACAAAGTTAACACACATTATGCACAGAATCTCCGGGGC

AGGGTCACCGTGAGCATAGACACATCCACGACCACAGCCTATATGGAACTGAGGAGCCTGAGATCT

GACGACACGGCCGTCTATTACTGTGCGAGAGACTGGGGTGGGCCGTTTGGGAACGCTTTTGATTTC

TGGGGCCAAGGGACAATGGTCACCGTCTCGAGCG

>SC11-035 VH PROTEIN
(SEQ ID NO: 101)
QVQLVQSGAEVKKPGSSVKVSCKTSGYAFNGYGISWVRQAPGQGLEWVAWINTYKVNTHYAQNLRG

RVTVSIDTSTTTAYMELRSLRSDDTAVYYCARDWGGPFGNAFDFWGQGTMVTVSS

>SC11-035 VL DNA
(SEQ ID NO: 102)
GACATCCAGATGACCCAGTCTCCATCCTCCCTGGCTGCATCTATAGGAGACAGTGTCACCATCACT

TGCCGGGCAAGTCAGAGCGTTGGCTCTTACTTAAATTGGTATCAGCAAAAACCAGGGAAAGCCCCT

AAGTTGTTGATCTATGGTGCATCCAATGTGCAAAGTGGGGTCCCATCAAGGTTTAGTGGCAGTGAG

TCTGGGACAGAGTCCACACTCACCATCAACAATCTGCAGCCTGAAGATTCTGCAACTTACTACTGT

CAACAGAGTTACAGTACCCCTAGAACGTTCGGCCAAGGGACCAAGGTGGAAATCAAAC

>SC11-035 VL PROTEIN
(SEQ ID NO: 103)
DIQMTQSPSSLAASIGDSVTITCRASQSVGSYLNWYQQKPGKAPKLLIYGASNVQSGVPSRFSGSE

SGTESTLTINNLQPEDSATYYCQQSYSTPRTFGQGTKVEIK

>SC11-036 VH DNA
(SEQ ID NO: 104)
GAGGTGCAGCTGGTGCAGTCTGGGGCTGAGGTGAAGAAGCCTGGGGCCTCAGTGACGGTTTCCTGC

AAGGCATCTGGATACGCCTTCACCAGCTACTATTTACACTGGGTGCGACAGGCCCCTGGACAAGGG

CTTGAGTGGATGGGGATAATGAATCTTCATGGTGGTAGCACAACCTACGCACAGAAGTTCCAGGGC

| SEQUENCES |
| --- |
| AGAGTCACCATGACCAGGGACACGTCCACGAGGACAGTTTACATGGAGCTGAGCGGCCTGAGATCT |
| GAGGACTCGGCCGTATATTACTGTGCCCGAGAGAGTCCCGATAGCAGTGGTTATCCTGGCTACTAC |
| GGTATGGACGTCTGGGGCCAGGGGACCACGGTCACCGTCTCGAGC |
| >SC11-036 VH PROTEIN (SEQ ID NO: 105) |
| EVQLVQSGAEVKKPGASVTVSCKASGYAFTSYYLHWVRQAPGQGLEWMGIMNLHGGSTTYAQKFQG |
| RVTMTRDTSTRTVYMELSGLRSEDSAVYYCARESPDSSGYPGYYGMDVWGQGTTVTVSS |
| >SC11-036 VL DNA (SEQ ID NO: 106) |
| GAAATTGTGTTGACGCAGTCTCCAGGCACCCTGTCTTTGTCTCCAGGGGAAAGAGCCACCCTCTCC |
| TGCAGGGCCAGTCAGAGTGTTAGCAGCGACTTCTTCGCCTGGTACCAGCAGAAACGTGGCCAGACT |
| CCCACCCTCCTCATCTATGGTACATCCACCAGGGCCACTGGCATCCCAGACAGGTTCAGTGGCAGT |
| GGGTCTGGGACAGACTTCACACTCAGCGTCGCCAGACTGGAGCCTGAAGATTTTGCAGTGTATTAC |
| TGTCAGCAGTATGGTAGCTCGACGTGGACGTTCGGCCAAGGGACCAAGGTGGAAATCAAAC |
| >SC11-036 VL PROTEIN (SEQ ID NO: 107) |
| EIVLTQSPGTLSLSPGERATLSCRASQSVSSDFFAWYQQKRGQTPTLLIYGTSTRATGIPDRFSGS |
| GSGTDFTLSVARLEPEDFAVYYCQQYGSSTWTFGQGTKVEIK |
| >SC11-038 VH DNA (SEQ ID NO: 108) |
| GAGGTGCAGCTGGTGGAGTCTGGGGCTGAGGTGAAGAAGCCTGGGGCCTCAGTGAAGGTTTCCTGC |
| AAGGCATCTGGATACGCCTTCACCAGCTACTATTTGCACTGGGTGCGACAGGCCCCTGGACAAGGG |
| CTTGAGTGGATGGGGATAATGAACCCTCATGGTGGTAGCACAACCTACGCACAGAAGTTCCAGGGC |
| AGAGTCACCATGACCAGGGACACGTCCACGAGCACAGTCTACATGGAGCTGAGCAGCCTGAGATCT |
| GAGGACACGGCCGTGTATTACTGTGCCCGAGAGAGTCCCGATAGTAGTGGTTATCCTGGCTACTAC |
| GGTATGGACGTCTGGGGCCAAGGGACCACGGTCACCGTCTCGAGC |
| >SC11-038 VH PROTEIN (SEQ ID NO: 109) |
| EVQLVESGAEVKKPGASVKVSCKASGYAFTSYYLHWVRQAPGQGLEWMGIMNPHGGSTTYAQKFQG |
| RVTMTRDTSTSTVYMELSSLRSEDTAVYYCARESPDSSGYPGYYGMDVWGQGTTVTVSS |
| >SC11-038 VL DNA (SEQ ID NO: 110) |
| TCCTATGAGCTGACTCAGCCACCCTCAGCGTCTGGGACCCCCGGGCAGAGGGTCACCATGTCTTGT |
| TCTGGAAGCAGATCCAACATCGGATCTAATCCTGTAAGCTGGTTCCAGCAACTCCCGGGAATGGTC |
| CCCAAACTCCTCATCTATACTAATGATCAGCGGCCCTCAGGGGTCCCTGACCGATTCTCTGGCTCC |
| AAGTCTGGCCCCTCAGCCTCCCTGGCCATCAGTGGGCTCCAGTCTGAGGATGAGGCTGATTATTAC |
| TGTGCAGCATGGGATGACAGCCTGAAAGGTTGGGTGTTCGGCGGAGGGACCAAGCTGACCGTCCTA |
| G |
| >SC11-038 VL PROTEIN (SEQ ID NO: 111) |
| SYELTQPPSASGTPGQRVTMSCSGSRSNIGSNPVSWFQQLPGMVPKLLIYTNDQRPSGVPDRFSGS |
| KSGPSASLAISGLQSEDEADYYCAAWDDSLKGWVFGGGTKLTVL |
| >SC11-039 VH DNA (SEQ ID NO: 112) |
| GAGGTCCAGCTGGTACAGTCTGGAGCAGAGGTGAAAAAGCCCGGGGAGTCTGTGAAGATCTCCTGT |
| AAGACTTCTGGTTACGCCTTTACCGGCTACGGTATCAGCTGGGTGCGACAGGCCCCTGGACAAGGC |
| CTTGAGTGGATGGGATGGATCAACACTTACAAATTTAACACAAATTATGCACAGAACCTGCAGGGC |

| SEQUENCES |
|---|

AGAGTCACCATGACCATAGACACATCCACGAGCGCAGCCTACATGGAGCTGAGGAGCCTGAGATAT

GAGGACACGGCCGTATATTTCTGTGCGAGAGACTGGGCTGGGCCGTTTGGGAATGCTTTTGATGTC

TGGGGCCAGGGGACAATGGTCACCGTCTCGAGCG

>SC11-039 VH PROTEIN
(SEQ ID NO: 113)
EVQLVQSGAEVKKPGESVKISCKTSGYAFTGYGISWVRQAPGQGLEWMGWINTYKFNTNYAQNLQG

RVTMTIDTSTSAAYMELRSLRYEDTAVYFCARDWAGPFGNAFDVWGQGTMVTVSS

>SC11-039 VL DNA
(SEQ ID NO: 114)
ACATCCAGATGACCCAGTCTCCATCTTCCCTGTCTGCATCTATAGGAGACAGAGTCGCCATCACTT

GCCAGGCGAGTCAGGACATTAGCGACTATTTAAATTGGTATCAGCAACAACCAGGGAAAGCCCCTA

AGCTCCTGCTCTACGGTGCATCCAATTTGGAAACAGGGGTCCCATCAAGGTTCAGTGGAAGTGGAT

CTGGGACAGATTTTACTTTCACCATCAGCAGCCTGCAGCCTGAAGACATTGCAACATATTATTGTC

AACAGTATGGTAATCTCCCTCCGACTTTCGGCGGGGGGACCAAGCTGGAGATCAAAC

>SC11-039 VL PROTEIN
(SEQ ID NO: 115)
IQMTQSPSSLSASIGDRVAITCQASQDISDYLNWYQQPGKAPKLLLYGASNLETGVPSRFSGSGS

GTDFTFTISSLQPEDIATYYCQQYGNLPPTFGGGTKLEIK

>SC09-114 VH PROTEIN
(SEQ ID NO: 116)
QVQLVQSGAEVKKPGSSVKVSCKSSGGTSNNYAISWVRQAPGQGLDWMGGISPIFGSTAYAQKFQG

RVTISADIFSNTAYMELNSLTSEDTAVYFCARHGNYYYYSGMDVWGQGTTVTVSS

>SC09-114 VL PROTEIN
(SEQ ID NO: 117)
SYVLTQPPAVSGTPGQRVTISCSGSDSNIGRRSVNWYQQFPGTAPKLLIYSNDQRPSVVPDRFSGS

KSGTSASLAISGLQSEDEAEYYCAAWDDSLKGAVFGGGTQLTVL

>SC08-031 VH DNA
(SEQ ID NO: 118)
GAGGTGCAGCTGGTGGAGTCTGGGGGAGGCCTGGTACAGCCTGGCAGGTCCCTGAGACTCTCCTGT

GCAGCCTCTGGATTCACCTTTGATGAGTATATCATGCATTGGGTCCGGCAAGCTCCCGGGAAGGGC

CCGGAATGGGTCGCAGGTATTAATTGGAAAGGTAATTTCATGGGTTATGCGGACTCTGTCCAGGGC

CGATTCACCATCTCCAGAGACAACGCCAAGAACTCCCTCTATCTGCAAATGAACAGTCTGAGAGCT

GACGACACGGCCTTATATTACTGTGCAAAAGACCGGCTGGAGAGTTCAGCTATGGACATTCTAGAA

GGGGGTACTTTTGATATCTGGGGCCAAGGGACAATGGTCACC

>SC08-031 VH PROTEIN
(SEQ ID NO: 119)
EVQLVESGGGLVQPGRSLRLSCAASGFTFDEYIMHWVRQAPGKGPEWVAGINWKGNFMGYADSVQG

RFTISRDNAKNSLYLQMNSLRADDTALYYCAKDRLESSAMDILEGGTEDIWGQGTMVT

>SC08-031 VL DNA
(SEQ ID NO: 120)
CAGTCTGCCCTGACTCAGCCTGCCTCCGTGTCTGGGTCTCCTGGACAGTCGATCACCATCTCCTGC

ACTGGAACCAGCAGTGACGTTGGTGGTTATAACTATGTCTCCTGGTACCAACAGCACCCAGGCAAA

GCCCCCAAACTCATGATTTATGATGTCAGTAGTCGGCCCTCAGGGGTTTCTAATCGCTTCTCTGGC

TCCAAGTCTGGCGACACGGCCTCCCTGAGCATCTCTGGGCTCCAGGCTGAGGACGAGGCTGATTAT

TACTGCAGCTCATATACAAGCAGCAGCACTCATGTCTTCGGAACTGGGACCAAGGTCACCGTCCTA

G

| SEQUENCES |
| --- |

>SC08-031 VL PROTEIN
(SEQ ID NO: 121)
QSALTQPASVSGSPGQSITISCTGTSSDVGGYNYVSWYQQHPGKAPKLMIYDVSSRPSGVSNRFSG

SKSGDTASLSISGLQAEDEADYYCSSYTSSSTHVFGTGTKVTVL

>SC08-032 VH DNA
(SEQ ID NO: 122)
GAGGTGCAGCTGGTGGAGTCTGGGGGAGGCCTGGTACAGCCTGGCAGGTCCCTGAGACTGTCCTGT

GCAGCCTCTGGATTCAGCTTTGATGAGTACATCATGCATTGGGTCCGGCAAGCTCCAGGGAAGGGC

CTGGAGTGGGTCGCAGGTATTAATTGGAAAGGTAATTTCATGGGTTATGCGGACTCTGTCCAGGGC

CGATTCACCATCTCCAGAGACAACGGCAAGAACTCCCTCTATCTGCAAATGAACAGTCTGAGAGCT

GAGGACACGGCCTTGTATTACTGTGCAAAAGACCGGCTGGAGAGTTCAGCTATGGACATTCTAGAA

GGGGGTACTTTTGATATCTGGGGCCAAGGGACAATGGTCACCGTCTCGAGC

>SC08-032 VH PROTEIN
(SEQ ID NO: 123)
EVQLVESGGGLVQPGRSLRLSCAASGFSFDEYIMHWVRQAPGKGLEWVAGINWKGNFMGYADSVQG

RFTISRDNGKNSLYLQMNSLRAEDTALYYCAKDRLESSAMDILEGGTFDIWGQGTMVTVSS

>SC08-032 VL DNA
(SEQ ID NO: 124)
CAGTCTGCCCTGACTCAGCCTGCCTCCGTGTCTGGGTCTCCTGGACAGTCGATCACCATCTCCTGC

ACTGGAACCCGCAGGGACGTTGGTGATTATAAGTATGTCTCCTGGTACCAACAACACCCAGGCAAA

GCCCCCAAACTCATGATTTATGATGTCAGTAATCGGCCCTCAGGGGTCTCTAATCGCTTCTCTGGC

TCCAAGTCTGGCACCACGGCCTCCCTGACCATCTCTGGGCTCCAGGCTGAGGACGAGGCTGATTAT

TATTGCAGTTCATACACAACCAGCAACACTCGGGTGTTCGGCGGAGGGACCAAGCTGACCGTCCTA

G

>SC08-032 VL PROTEIN
(SEQ ID NO: 125)
QSALTQPASVSGSPGQSITISCTGTRRDVGDYKYVSWYQQHPGKAPKLMIYDVSNRPSGVSNRF

SGSKSGTTASLTISGLQAEDEADYYCSSYTTSNTRVFGGGTKLTVL

>SC08-034 VH DNA
(SEQ ID NO: 126)
GAGGTGCAGCTGGTGGAGACTGGGGGAGGCCTGGTACAGCCTGGCAGGTCCCTGAGACTCTCCTGT

GCAGCCTCTGGATTCACCTTTGATGAGTATATCATGCATTGGGTCCGGCAAGCTCCCGGGAAGGGC

CCGGAATGGGTCGCAGGTATTAATTGGAAAGGTAATTTCATGGGTTATGCGGACTCTGTCCAGGGC

CGATTCACCATCTCCAGAGACAACGCCAAGAACTCCCTCTATCTGCAAATGAACAGTCTGAGAGCT

GACGACACGGCCTTATATTACTGTGCAAAAGACCGGCTGGAGAGTTCAGCTATGGACATTCTAGAA

GGGGGTACTTTTGATATCTGGGGCCAAGGGACAATGGTCACCGTCTCGAGC

>SC08-034 VH PROTEIN
(SEQ ID NO: 127)
EVQLVETGGGLVQPGRSLRLSCAASGFTFDEYIMHWVRQAPGKGPEWVAGINWKGNFMGYADSVQG

RFTISRDNAKNSLYLQMNSLRADDTALYYCAKDRLESSAMDILEGGTFDIWGQGTMVTVSS

>SC08-034 VL DNA
(SEQ ID NO: 128)
GACATCCAGATGACCCAGTCTCCATCCTCCCTGTCTGCATCTGTGGGAGACAGAGTCACCATCACT

TGCCGGGCAAGTCAGGGCATTAGAAATGATTTAGGCTGGTATCAGCAGAAACCAGGGAAAGCCCCT

AAGCGCCTGATCTATGCTGCATCCAGTTTGCAAAGTGGGGTCCCATCAAGGTTCAGTGGCAGTGGA

TCTGGGACAGATTTCACTCTCACCATCAGCAGTCTGCAACCTGAAGATTTTGCAACTTACTATTGT

CAACAGGCTAACACTTATCCACTCACTTTCGGCGGAGGGACCAAGCTGGAGATCAAAC

-continued

SEQUENCES

>SC08-034 VL PROTEIN
(SEQ ID NO: 129)
DIQMTQSPSSLSASVGDRVTITCRASQGIRNDLGWYQQKPGKAPKRLIYAASSLQSGVPSRFSGSG

SGTDFTLTISSLQPEDFATYYCQQANTYPLTFGGGTKLEIK

>SC08-035 VH DNA
(SEQ ID NO: 130)
GAGGTGCAGCTGGTGGAGTCTGGGGGAGGCCTGGTACAGCCTGGCAGGTCCCTGAGACTCTCCTGT

GCAGCCTCTGGATTCACCTTTGATGAGTATATCATGCATTGGGTCCGGCAAGCTCCCGGGAAGGGC

CCGGAATGGGTCGCAGGTATTAATTGGAAAGGTAATTTCATGGGTTATGCGGACTCTGTCCAGGGC

CGATTCACCATCTCCAGAGACAACGCCAAGAACTCCCTCTATCTGCAAATGAACAGTCTGAGAGCT

GACGACACGGCCTTATATTACTGTGCAAAAGACCGGCTGGAGAGTTCAGCTATGGACATTCTAGAA

GGGGGTACTTTTGATATCTGGGGCCAAGGGACAATGGTCACCGTCTCGAGC

>SC08-035 VH PROTEIN
(SEQ ID NO: 131)
EVQLVESGGGLVQPGRSLRLSCAASGFTFDEYIMHWVRQAPGKGPEWVAGINWKGNFMGYADSVQG

RFTISRDNAKNSLYLQMNSLRADDTALYYCAKDRLESSAMDILEGGTFDIWGQGTMVTVSS

>SC08-035 VL DNA
(SEQ ID NO: 132)
TCTTCTGAGCTGACTCAGGACCCTGCTGTGTCTGTGGCCTTGGGACAGACAGTCAGGATCACATGC

CAAGGAGACAGCCTCAGAAGCTATTATGCAAGCTGGTACCAGCAGAAGCCAGGACAGGCCCCTGTA

CTTGTCATCTATGGTAAAAACAACCGGCCCTCAGGGATCCCAGACCGATTCTCTGGCTCCAGCTCA

AGAAACACAGCTTCCTTGACCATCACTGGGGCTCAGGCGGAAGATGAGGCTGACTATTATTGTGAC

TCCCGGGACAGCAGTGGAACCCATTATGTCTTCGGAGGTGGGACCAAGGTCACCGTCCTAG

>SC08-035 VL PROTEIN
(SEQ ID NO: 133)
SSELTQDPAVSVALGQTVRITCQGDSLRSYYASWYQQKPGQAPVLVIYGKNNRPSGIPDRFSGSSS

RNTASLTITGAQAEDEADYYCDSRDSSGTHYVFGGGTKVTVL

REFERENCES

Brochet et al., *Nucl. Acids Res.* 36, W503-508 (2008).
De Kruif J. et al., *Proc. Natl. Acad. Sci. USA* 92:3938 (1995).
Kanegae et al., *J. Virol.* 64:2860-2865 (1990).
Kubota-Koketsu et al., *Biochem. Biophys. Res. Comm.* 387: 180-185 (2009).
Rota et al., *J. Gen. Virol.* 73:2737-2742 (1992).
Thompson et al., *JAMA* 289(2):179-186 (2003).
Thompson et al., *JAMA* 292(11):1333-1340 (2004).
Wrammert et al., *Nature* 453:667-672 (2008).

What is claimed is:

1. A binding molecule able to:
specifically bind to hemagglutinin (HA) of influenza B virus strains of the B/Yamagata and B/Victoria lineage, and
neutralize the influenza B virus strains of the B/Yamagata and/or B/Victoria lineage,
wherein the binding molecule does not bind to HA of influenza A viruses and wherein the binding molecule comprises the heavy chain CDR1 of SEQ ID NO: 54, the heavy chain CDR2 of SEQ ID NO: 55, the heavy chain CDR3 of SEQ ID NO: 56, the light chain CDR1 of SEQ ID NO: 57, the light chain CDR2 of SEQ ID NO: 5, and the light chain CDR3 of SEQ ID NO: 58.

2. The binding molecule of claim 1, which binds to the head region of HA of influenza B virus.

3. The binding molecule of claim 2, wherein the binding molecule comprises a heavy chain variable region comprising SEQ ID NO: 113.

4. The binding molecule of claim 3, wherein the binding molecule comprises a light chain variable region comprising SEQ ID NO: 115.

5. The binding molecules of claim 1, wherein the binding molecule comprises:
the heavy chain variable region of SEQ ID NO: 113, and
the light chain variable region of SEQ ID NO: 115.

6. The binding molecule of claim 1, wherein the binding molecule inhibits egress of influenza B virus from a cell infected therewith.

7. The binding molecule of claim 1, wherein the binding molecule is an isolated antibody or an antigen binding fragment thereof.

8. An immunoconjugate comprising:
at least one binding molecule of claim 1, and
at least one tag, wherein at least one tag is conjugated to the binding molecule.

9. An isolated polynucleotide encoding the binding molecule of claim 1.

10. A pharmaceutical composition comprising:
the binding molecule of claim 1, and
a pharmaceutically acceptable carrier or excipient.

11. A pharmaceutical composition comprising:
the immunoconjugate of claim 8, and
a pharmaceutically acceptable carrier or excipient.

12. A pharmaceutical composition comprising:
the isolated polynucleotide of claim 9, and
a pharmaceutically acceptable carrier or excipient.

13. A method of detecting an influenza B virus infection in a subject, the method comprising:
assaying the level of influenza B virus antigen in a biological sample of the subject utilizing the immunoconjugate of claim 8; and
comparing the assayed level of influenza B virus antigen in the biological sample with a control level, wherein an increase in the assayed level of influenza B virus antigen compared to the control level of the influenza B virus antigen is indicative of an influenza B virus infection in the subject.

14. The method according to claim 13, wherein when the assayed level indicates influenza B infection, the subject is treated for influenza B infection.

15. The binding molecule of claim 2, which binds to the head region of HA1 of an influenza B virus.

16. A method of inhibiting an influenza infection caused by influenza B virus in a subject, the method comprising:
administering the pharmaceutical composition of claim 10 to inhibit the influenza infection in the subject.

* * * * *

SEQUENCE LISTING

```
<160> NUMBER OF SEQ ID NOS: 133

<210> SEQ ID NO 1
<211> LENGTH: 8
<212> TYPE: PRT
<213> ORGANISM: Artificial
<220> FEATURE:
<223> OTHER INFORMATION: CR8033 HC CDR1

<400> SEQUENCE: 1

Gly Phe Ser Phe Asp Glu Tyr Thr
1               5

<210> SEQ ID NO 2
<211> LENGTH: 8
<212> TYPE: PRT
```

-continued

<213> ORGANISM: Artificial
<220> FEATURE:
<223> OTHER INFORMATION: CR8033 HC CDR2

<400> SEQUENCE: 2

Ile Asn Trp Lys Gly Asn Phe Met
1               5

<210> SEQ ID NO 3
<211> LENGTH: 20
<212> TYPE: PRT
<213> ORGANISM: Artificial
<220> FEATURE:
<223> OTHER INFORMATION: CR8033 HC CDR3

<400> SEQUENCE: 3

Ala Lys Asp Arg Leu Glu Ser Ser Ala Met Asp Ile Leu Glu Gly Gly
1               5                   10                  15

Thr Phe Asp Ile
            20

<210> SEQ ID NO 4
<211> LENGTH: 7
<212> TYPE: PRT
<213> ORGANISM: Artificial
<220> FEATURE:
<223> OTHER INFORMATION: CR8033 LC CDR1

<400> SEQUENCE: 4

Gln Ser Val Ser Ser Ser Tyr
1               5

<210> SEQ ID NO 5
<211> LENGTH: 3
<212> TYPE: PRT
<213> ORGANISM: Artificial
<220> FEATURE:
<223> OTHER INFORMATION: CR8033 LC CDR2

<400> SEQUENCE: 5

Gly Ala Ser
1

<210> SEQ ID NO 6
<211> LENGTH: 9
<212> TYPE: PRT
<213> ORGANISM: Artificial
<220> FEATURE:
<223> OTHER INFORMATION: CR8033 LC CDR3

<400> SEQUENCE: 6

Gln Gln Tyr Gly Ser Ser Pro Trp Thr
1               5

<210> SEQ ID NO 7
<211> LENGTH: 8
<212> TYPE: PRT
<213> ORGANISM: Artificial
<220> FEATURE:
<223> OTHER INFORMATION: HC CDR1

<400> SEQUENCE: 7

Gly Tyr Ile Phe Thr Glu Ser Gly
1               5

<210> SEQ ID NO 8

```
<211> LENGTH: 8
<212> TYPE: PRT
<213> ORGANISM: Artificial
<220> FEATURE:
<223> OTHER INFORMATION: HC CDR2

<400> SEQUENCE: 8

Ile Ser Gly Tyr Ser Gly Asp Thr
1               5

<210> SEQ ID NO 9
<211> LENGTH: 18
<212> TYPE: PRT
<213> ORGANISM: Artificial
<220> FEATURE:
<223> OTHER INFORMATION: HC CDR3

<400> SEQUENCE: 9

Ala Arg Asp Val Gln Tyr Ser Gly Ser Tyr Leu Gly Ala Tyr Tyr Phe
1               5                   10                  15
Asp Tyr

<210> SEQ ID NO 10
<211> LENGTH: 8
<212> TYPE: PRT
<213> ORGANISM: Artificial
<220> FEATURE:
<223> OTHER INFORMATION: LC CDR1

<400> SEQUENCE: 10

Ser Ser Asn Ile Gly Thr Asn Tyr
1               5

<210> SEQ ID NO 11
<211> LENGTH: 3
<212> TYPE: PRT
<213> ORGANISM: Artificial
<220> FEATURE:
<223> OTHER INFORMATION: LC CDR2

<400> SEQUENCE: 11

Arg Ser Tyr
1

<210> SEQ ID NO 12
<211> LENGTH: 11
<212> TYPE: PRT
<213> ORGANISM: Artificial
<220> FEATURE:
<223> OTHER INFORMATION: LC CDR3

<400> SEQUENCE: 12

Ala Thr Trp Asp Asp Ser Leu Asn Gly Trp Val
1               5                   10

<210> SEQ ID NO 13
<211> LENGTH: 11
<212> TYPE: PRT
<213> ORGANISM: Artificial
<220> FEATURE:
<223> OTHER INFORMATION: LC CDR3

<400> SEQUENCE: 13

Ala Thr Trp Asp Asp Ser Leu Asp Gly Trp Val
1               5                   10
```

```
<210> SEQ ID NO 14
<211> LENGTH: 8
<212> TYPE: PRT
<213> ORGANISM: Artificial
<220> FEATURE:
<223> OTHER INFORMATION: HC CDR1

<400> SEQUENCE: 14

Gly Phe Thr Phe Asp Asp Tyr Ala
1               5

<210> SEQ ID NO 15
<211> LENGTH: 8
<212> TYPE: PRT
<213> ORGANISM: Artificial
<220> FEATURE:
<223> OTHER INFORMATION: HC CDR2

<400> SEQUENCE: 15

Ile Asn Trp Val Ser Thr Thr Met
1               5

<210> SEQ ID NO 16
<211> LENGTH: 20
<212> TYPE: PRT
<213> ORGANISM: Artificial
<220> FEATURE:
<223> OTHER INFORMATION: HC CDR3

<400> SEQUENCE: 16

Ala Lys Asp Arg Leu Glu Ser Ala Ala Ile Asp Ile Leu Glu Gly Gly
1               5                   10                  15

Thr Phe Asp Ile
            20

<210> SEQ ID NO 17
<211> LENGTH: 9
<212> TYPE: PRT
<213> ORGANISM: Artificial
<220> FEATURE:
<223> OTHER INFORMATION: LC CDR1

<400> SEQUENCE: 17

Ser Ser Asp Val Gly Gly Tyr Asn Tyr
1               5

<210> SEQ ID NO 18
<211> LENGTH: 3
<212> TYPE: PRT
<213> ORGANISM: Artificial
<220> FEATURE:
<223> OTHER INFORMATION: LC CDR2

<400> SEQUENCE: 18

Asp Val Ser
1

<210> SEQ ID NO 19
<211> LENGTH: 10
<212> TYPE: PRT
<213> ORGANISM: Artificial
<220> FEATURE:
<223> OTHER INFORMATION: LC CDR3

<400> SEQUENCE: 19

Ser Ser Tyr Ala Ser Gly Ser Thr Tyr Val
1               5                   10
```

```
<210> SEQ ID NO 20
<211> LENGTH: 10
<212> TYPE: PRT
<213> ORGANISM: Artificial
<220> FEATURE:
<223> OTHER INFORMATION: HC CDR1

<400> SEQUENCE: 20

Gly Gly Ser Ile Asn Ser Ser Pro Tyr Lys
1               5                   10

<210> SEQ ID NO 21
<211> LENGTH: 7
<212> TYPE: PRT
<213> ORGANISM: Artificial
<220> FEATURE:
<223> OTHER INFORMATION: HC CDR2

<400> SEQUENCE: 21

Phe Tyr Tyr Asp Gly Ser Thr
1               5

<210> SEQ ID NO 22
<211> LENGTH: 18
<212> TYPE: PRT
<213> ORGANISM: Artificial
<220> FEATURE:
<223> OTHER INFORMATION: HC CDR3

<400> SEQUENCE: 22

Ala Ala Tyr Cys Ser Ser Ile Ser Cys His Ala Tyr Tyr Asp Tyr Met
1               5                   10                  15

Asn Val

<210> SEQ ID NO 23
<211> LENGTH: 11
<212> TYPE: PRT
<213> ORGANISM: Artificial
<220> FEATURE:
<223> OTHER INFORMATION: LC CDR1

<400> SEQUENCE: 23

Gln Ser Leu Arg His Glu Asn Gly Tyr Asn Tyr
1               5                   10

<210> SEQ ID NO 24
<211> LENGTH: 3
<212> TYPE: PRT
<213> ORGANISM: Artificial
<220> FEATURE:
<223> OTHER INFORMATION: LC CDR2

<400> SEQUENCE: 24

Leu Gly Ser
1

<210> SEQ ID NO 25
<211> LENGTH: 9
<212> TYPE: PRT
<213> ORGANISM: Artificial
<220> FEATURE:
<223> OTHER INFORMATION: LC CDR3

<400> SEQUENCE: 25

Met Gln Ala Leu Thr Gln Thr Leu Thr
```

```
1               5

<210> SEQ ID NO 26
<211> LENGTH: 8
<212> TYPE: PRT
<213> ORGANISM: Artificial
<220> FEATURE:
<223> OTHER INFORMATION: LC CDR1

<400> SEQUENCE: 26

Gly Phe Thr Phe Ser Ser Tyr Ala
1               5

<210> SEQ ID NO 27
<211> LENGTH: 7
<212> TYPE: PRT
<213> ORGANISM: Artificial
<220> FEATURE:
<223> OTHER INFORMATION: LC CDR2

<400> SEQUENCE: 27

Leu Ser Asp Glu Ser Thr Thr
1               5

<210> SEQ ID NO 28
<211> LENGTH: 17
<212> TYPE: PRT
<213> ORGANISM: Artificial
<220> FEATURE:
<223> OTHER INFORMATION: LC CDR3

<400> SEQUENCE: 28

Ala Glu Asp Leu Gly Thr Val Met Asp Ser Tyr Tyr Tyr Gly Met Asn
1               5                   10                  15
Val

<210> SEQ ID NO 29
<211> LENGTH: 11
<212> TYPE: PRT
<213> ORGANISM: Artificial
<220> FEATURE:
<223> OTHER INFORMATION: LC CDR1

<400> SEQUENCE: 29

Gln Ser Leu Leu His Ser Asn Gly Leu Asn Tyr
1               5                   10

<210> SEQ ID NO 30
<211> LENGTH: 9
<212> TYPE: PRT
<213> ORGANISM: Artificial
<220> FEATURE:
<223> OTHER INFORMATION: LC CDR3

<400> SEQUENCE: 30

Met Gln Ala Leu Gln Thr Pro Phe Thr
1               5

<210> SEQ ID NO 31
<211> LENGTH: 8
<212> TYPE: PRT
<213> ORGANISM: Artificial
<220> FEATURE:
<223> OTHER INFORMATION: HC CDR1

<400> SEQUENCE: 31
```

Gly Asp Thr Phe Thr Asn Tyr His
1               5

<210> SEQ ID NO 32
<211> LENGTH: 8
<212> TYPE: PRT
<213> ORGANISM: Artificial
<220> FEATURE:
<223> OTHER INFORMATION: HC CDR2

<400> SEQUENCE: 32

Ile Asn Pro Ser Gly Gly Asp Thr
1               5

<210> SEQ ID NO 33
<211> LENGTH: 23
<212> TYPE: PRT
<213> ORGANISM: Artificial
<220> FEATURE:
<223> OTHER INFORMATION: HC CDR3

<400> SEQUENCE: 33

Ala Thr Asp Glu Ser Pro Gly Leu Leu Thr Gly Leu Arg Asp Tyr Trp
1               5                   10                  15

Tyr Tyr Tyr Gly Met Asp Val
            20

<210> SEQ ID NO 34
<211> LENGTH: 10
<212> TYPE: PRT
<213> ORGANISM: Artificial
<220> FEATURE:
<223> OTHER INFORMATION: LC CDR3

<400> SEQUENCE: 34

Gln Gln Tyr Gly Ser Ser Pro Leu Cys Ser
1               5                   10

<210> SEQ ID NO 35
<211> LENGTH: 8
<212> TYPE: PRT
<213> ORGANISM: Artificial
<220> FEATURE:
<223> OTHER INFORMATION: HC CDR1

<400> SEQUENCE: 35

Gly Tyr Ser Phe Thr Gly Tyr Tyr
1               5

<210> SEQ ID NO 36
<211> LENGTH: 8
<212> TYPE: PRT
<213> ORGANISM: Artificial
<220> FEATURE:
<223> OTHER INFORMATION: HC CDR2

<400> SEQUENCE: 36

Ile Asn Pro Ile Ser Gly Asp Thr
1               5

<210> SEQ ID NO 37
<211> LENGTH: 14
<212> TYPE: PRT
<213> ORGANISM: Artificial
<220> FEATURE:
<223> OTHER INFORMATION: HC CDR3

```
<400> SEQUENCE: 37

Ala Arg Val Ala Gly Glu Asp Trp Phe Gly Asp Leu Asp Tyr
1               5                   10

<210> SEQ ID NO 38
<211> LENGTH: 3
<212> TYPE: PRT
<213> ORGANISM: Artificial
<220> FEATURE:
<223> OTHER INFORMATION: LC CDR2

<400> SEQUENCE: 38

Gly Thr Ser
1

<210> SEQ ID NO 39
<211> LENGTH: 9
<212> TYPE: PRT
<213> ORGANISM: Artificial
<220> FEATURE:
<223> OTHER INFORMATION: LC CDR3

<400> SEQUENCE: 39

Gln Gln Tyr Gly Ser Ser Pro Arg Thr
1               5

<210> SEQ ID NO 40
<211> LENGTH: 8
<212> TYPE: PRT
<213> ORGANISM: Artificial
<220> FEATURE:
<223> OTHER INFORMATION: HC CDR1

<400> SEQUENCE: 40

Gly Tyr Ala Phe Asn Gly Tyr Gly
1               5

<210> SEQ ID NO 41
<211> LENGTH: 8
<212> TYPE: PRT
<213> ORGANISM: Artificial
<220> FEATURE:
<223> OTHER INFORMATION: HC CDR2

<400> SEQUENCE: 41

Ile Asn Thr Tyr Lys Val Asn Thr
1               5

<210> SEQ ID NO 42
<211> LENGTH: 14
<212> TYPE: PRT
<213> ORGANISM: Artificial
<220> FEATURE:
<223> OTHER INFORMATION: HC CDR3

<400> SEQUENCE: 42

Ala Arg Asp Trp Gly Gly Pro Phe Gly Asn Ala Phe Asp Phe
1               5                   10

<210> SEQ ID NO 43
<211> LENGTH: 6
<212> TYPE: PRT
<213> ORGANISM: Artificial
<220> FEATURE:
<223> OTHER INFORMATION: LC CDR1

<400> SEQUENCE: 43
```

```
Gln Ser Val Gly Ser Tyr
1               5

<210> SEQ ID NO 44
<211> LENGTH: 9
<212> TYPE: PRT
<213> ORGANISM: Artificial
<220> FEATURE:
<223> OTHER INFORMATION: LC CDR3

<400> SEQUENCE: 44

Gln Gln Ser Tyr Ser Thr Pro Arg Thr
1               5

<210> SEQ ID NO 45
<211> LENGTH: 8
<212> TYPE: PRT
<213> ORGANISM: Artificial
<220> FEATURE:
<223> OTHER INFORMATION: HC CDR1

<400> SEQUENCE: 45

Gly Tyr Ala Phe Thr Ser Tyr Tyr
1               5

<210> SEQ ID NO 46
<211> LENGTH: 8
<212> TYPE: PRT
<213> ORGANISM: Artificial
<220> FEATURE:
<223> OTHER INFORMATION: HC CDR2

<400> SEQUENCE: 46

Met Asn Leu His Gly Gly Ser Thr
1               5

<210> SEQ ID NO 47
<211> LENGTH: 18
<212> TYPE: PRT
<213> ORGANISM: Artificial
<220> FEATURE:
<223> OTHER INFORMATION: HC CDR3

<400> SEQUENCE: 47

Ala Arg Glu Ser Pro Asp Ser Ser Gly Tyr Pro Gly Tyr Tyr Gly Met
1               5                   10                  15

Asp Val

<210> SEQ ID NO 48
<211> LENGTH: 7
<212> TYPE: PRT
<213> ORGANISM: Artificial
<220> FEATURE:
<223> OTHER INFORMATION: LC CDR1

<400> SEQUENCE: 48

Gln Ser Val Ser Ser Asp Phe
1               5

<210> SEQ ID NO 49
<211> LENGTH: 9
<212> TYPE: PRT
<213> ORGANISM: Artificial
<220> FEATURE:
<223> OTHER INFORMATION: LC CDR3
```

```
<400> SEQUENCE: 49

Gln Gln Tyr Gly Ser Ser Thr Trp Thr
1               5

<210> SEQ ID NO 50
<211> LENGTH: 8
<212> TYPE: PRT
<213> ORGANISM: Artificial
<220> FEATURE:
<223> OTHER INFORMATION: LC CDR2

<400> SEQUENCE: 50

Met Asn Pro His Gly Gly Ser Thr
1               5

<210> SEQ ID NO 51
<211> LENGTH: 8
<212> TYPE: PRT
<213> ORGANISM: Artificial
<220> FEATURE:
<223> OTHER INFORMATION: LC CDR1

<400> SEQUENCE: 51

Arg Ser Asn Ile Gly Ser Asn Pro
1               5

<210> SEQ ID NO 52
<211> LENGTH: 3
<212> TYPE: PRT
<213> ORGANISM: Artificial
<220> FEATURE:
<223> OTHER INFORMATION: LC CDR2

<400> SEQUENCE: 52

Thr Asn Asp
1

<210> SEQ ID NO 53
<211> LENGTH: 11
<212> TYPE: PRT
<213> ORGANISM: Artificial
<220> FEATURE:
<223> OTHER INFORMATION: LC CDR3

<400> SEQUENCE: 53

Ala Ala Trp Asp Asp Ser Leu Lys Gly Trp Val
1               5                   10

<210> SEQ ID NO 54
<211> LENGTH: 8
<212> TYPE: PRT
<213> ORGANISM: Artificial
<220> FEATURE:
<223> OTHER INFORMATION: LC CDR1

<400> SEQUENCE: 54

Gly Tyr Ala Phe Thr Gly Tyr Gly
1               5

<210> SEQ ID NO 55
<211> LENGTH: 8
<212> TYPE: PRT
<213> ORGANISM: Artificial
<220> FEATURE:
<223> OTHER INFORMATION: HC CDR2

<400> SEQUENCE: 55
```

Ile Asn Thr Tyr Lys Phe Asn Thr
1               5

<210> SEQ ID NO 56
<211> LENGTH: 14
<212> TYPE: PRT
<213> ORGANISM: Artificial
<220> FEATURE:
<223> OTHER INFORMATION: HC CDR3

<400> SEQUENCE: 56

Ala Arg Asp Trp Ala Gly Pro Phe Gly Asn Ala Phe Asp Val
1               5                   10

<210> SEQ ID NO 57
<211> LENGTH: 6
<212> TYPE: PRT
<213> ORGANISM: Artificial
<220> FEATURE:
<223> OTHER INFORMATION: LC CDR1

<400> SEQUENCE: 57

Gln Asp Ile Ser Asp Tyr
1               5

<210> SEQ ID NO 58
<211> LENGTH: 9
<212> TYPE: PRT
<213> ORGANISM: Artificial
<220> FEATURE:
<223> OTHER INFORMATION: LC CDR3

<400> SEQUENCE: 58

Gln Gln Tyr Gly Asn Leu Pro Pro Thr
1               5

<210> SEQ ID NO 59
<211> LENGTH: 8
<212> TYPE: PRT
<213> ORGANISM: Artificial
<220> FEATURE:
<223> OTHER INFORMATION: HC CDR1

<400> SEQUENCE: 59

Gly Phe Thr Phe Asp Glu Tyr Ile
1               5

<210> SEQ ID NO 60
<211> LENGTH: 10
<212> TYPE: PRT
<213> ORGANISM: Artificial
<220> FEATURE:
<223> OTHER INFORMATION: LC CDR3

<400> SEQUENCE: 60

Ser Ser Tyr Thr Ser Ser Ser Thr His Val
1               5                   10

<210> SEQ ID NO 61
<211> LENGTH: 8
<212> TYPE: PRT
<213> ORGANISM: Artificial
<220> FEATURE:
<223> OTHER INFORMATION: HC CDR1

<400> SEQUENCE: 61

```
Gly Phe Ser Phe Asp Glu Tyr Ile
1               5

<210> SEQ ID NO 62
<211> LENGTH: 9
<212> TYPE: PRT
<213> ORGANISM: Artificial
<220> FEATURE:
<223> OTHER INFORMATION: LC CDR1

<400> SEQUENCE: 62

Arg Arg Asp Val Gly Asp Tyr Lys Tyr
1               5

<210> SEQ ID NO 63
<211> LENGTH: 10
<212> TYPE: PRT
<213> ORGANISM: Artificial
<220> FEATURE:
<223> OTHER INFORMATION: LC CDR3

<400> SEQUENCE: 63

Ser Ser Tyr Thr Thr Ser Asn Thr Arg Val
1               5                   10

<210> SEQ ID NO 64
<211> LENGTH: 6
<212> TYPE: PRT
<213> ORGANISM: Artificial
<220> FEATURE:
<223> OTHER INFORMATION: LC CDR1

<400> SEQUENCE: 64

Gln Gly Ile Arg Asn Asp
1               5

<210> SEQ ID NO 65
<211> LENGTH: 3
<212> TYPE: PRT
<213> ORGANISM: Artificial
<220> FEATURE:
<223> OTHER INFORMATION: LC CDR2

<400> SEQUENCE: 65

Ala Ala Ser
1

<210> SEQ ID NO 66
<211> LENGTH: 9
<212> TYPE: PRT
<213> ORGANISM: Artificial
<220> FEATURE:
<223> OTHER INFORMATION: LC CDR3

<400> SEQUENCE: 66

Gln Gln Ala Asn Thr Tyr Pro Leu Thr
1               5

<210> SEQ ID NO 67
<211> LENGTH: 6
<212> TYPE: PRT
<213> ORGANISM: Artificial
<220> FEATURE:
<223> OTHER INFORMATION: LC CDR1

<400> SEQUENCE: 67

Ser Leu Arg Ser Tyr Tyr
```

<210> SEQ ID NO 68
<211> LENGTH: 3
<212> TYPE: PRT
<213> ORGANISM: Artificial
<220> FEATURE:
<223> OTHER INFORMATION: LC CDR2

<400> SEQUENCE: 68

Gly Lys Asn
1

<210> SEQ ID NO 69
<211> LENGTH: 11
<212> TYPE: PRT
<213> ORGANISM: Artificial
<220> FEATURE:
<223> OTHER INFORMATION: LC CDR3

<400> SEQUENCE: 69

Asp Ser Arg Asp Ser Ser Gly Thr His Tyr Val
1               5                   10

<210> SEQ ID NO 70
<211> LENGTH: 372
<212> TYPE: DNA
<213> ORGANISM: Artificial
<220> FEATURE:
<223> OTHER INFORMATION: SC08-033 VH DNA

<400> SEQUENCE: 70

```
gaggtgcagc tggtggagac tgggggaggc ctggtacagc ctggcaggtc cctgagactg        60
tcctgtgcag cctctggatt cagctttgat gagtacacca tgcattgggt ccggcaagct       120
ccagggaagg gcctggagtg ggtcgcaggt attaattgga aggtaatttt catgggttat       180
gcggactctg tccagggccg attcaccatc tccagagaca cggcaagaa  ctccctctat       240 ctgcaaatga acagtctgag agctgaggac acggccttgt attactgtgc aaaagaccgg       300
ctggagagtt cagctatgga cattctagaa gggggtactt ttgatatctg gggccaaggg       360
acaatggtca cc                                                           372
```

<210> SEQ ID NO 71
<211> LENGTH: 124
<212> TYPE: PRT
<213> ORGANISM: Artificial
<220> FEATURE:
<223> OTHER INFORMATION: SC08-033 VH PROTEIN

<400> SEQUENCE: 71

Glu Val Gln Leu Val Glu Thr Gly Gly Gly Leu Val Gln Pro Gly Arg
1               5                   10                  15

Ser Leu Arg Leu Ser Cys Ala Ala Ser Gly Phe Ser Phe Asp Glu Tyr
            20                  25                  30

Thr Met His Trp Val Arg Gln Ala Pro Gly Lys Gly Leu Glu Trp Val
        35                  40                  45

Ala Gly Ile Asn Trp Lys Gly Asn Phe Met Gly Tyr Ala Asp Ser Val
    50                  55                  60

Gln Gly Arg Phe Thr Ile Ser Arg Asp Asn Gly Lys Asn Ser Leu Tyr
65                  70                  75                  80

Leu Gln Met Asn Ser Leu Arg Ala Glu Asp Thr Ala Leu Tyr Tyr Cys
                85                  90                  95

```
Ala Lys Asp Arg Leu Glu Ser Ser Ala Met Asp Ile Leu Glu Gly Gly
            100                 105                 110

Thr Phe Asp Ile Trp Gly Gln Gly Thr Met Val Thr
            115                 120
```

<210> SEQ ID NO 72
<211> LENGTH: 325
<212> TYPE: DNA
<213> ORGANISM: Artificial
<220> FEATURE:
<223> OTHER INFORMATION: SC08-033 VL DNA

<400> SEQUENCE: 72

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca ccagggccac tggtatccca     180
gccaggttca gtggcagtgg gtctgggaca gacttcactc tcaccatcag cagactggag     240
cctgaagatc ttgcagtgta ttactgtcag cagtatggta gctcaccgtg gacgttcggc     300
caagggacca aggtggaaat caaac                                           325
```

<210> SEQ ID NO 73
<211> LENGTH: 108
<212> TYPE: PRT
<213> ORGANISM: Artificial
<220> FEATURE:
<223> OTHER INFORMATION: SC08-033 VL PROTEIN

<400> SEQUENCE: 73

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Arg Leu Glu
65                  70                  75                  80

Pro Glu Asp Leu Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 74
<211> LENGTH: 375
<212> TYPE: DNA
<213> ORGANISM: Artificial
<220> FEATURE:
<223> OTHER INFORMATION: SC08-059 VH DNA

<400> SEQUENCE: 74

```
gaggtccagc tggtacagtc tggagctgag gtgaagaagc ctggggcctc agtgagggtc      60
tcctgcaggg cctctggtta catctttacc gaatctggta tcacctgggt gcgccaggcc     120
cctggacaag gcttgagtg gatgggatgg atcagcggtt acagtggtga cacaaaatat     180
gcacagaaac tccagggcag agtcaccatg accaaagaca catccacgac cacagcctac     240
atggaattga ggagcctgag atatgacgac acggccgtat attactgtgc gagagacgtc     300
```

```
cagtacagtg ggagttattt gggcgcctac tactttgact attggagccc gggaaccctg    360
gtcaccgtct cgagc                                                     375

<210> SEQ ID NO 75
<211> LENGTH: 125
<212> TYPE: PRT
<213> ORGANISM: Artificial
<220> FEATURE:
<223> OTHER INFORMATION: SC08-059 VH PROTEIN

<400> SEQUENCE: 75

Glu Val Gln Leu Val Gln Ser Gly Ala Glu Val Lys Lys Pro Gly Ala
1               5                   10                  15

Ser Val Arg Val Ser Cys Arg Ala Ser Gly Tyr Ile Phe Thr Glu Ser
            20                  25                  30

Gly Ile Thr Trp Val Arg Gln Ala Pro Gly Gln Gly Leu Glu Trp Met
        35                  40                  45

Gly Trp Ile Ser Gly Tyr Ser Gly Asp Thr Lys Tyr Ala Gln Lys Leu
    50                  55                  60

Gln Gly Arg Val Thr Met Thr Lys Asp Thr Ser Thr Thr Thr Ala Tyr
65                  70                  75                  80

Met Glu Leu Arg Ser Leu Arg Tyr Asp Asp Thr Ala Val Tyr Tyr Cys
                85                  90                  95

Ala Arg Asp Val Gln Tyr Ser Gly Ser Tyr Leu Gly Ala Tyr Tyr Phe
            100                 105                 110

Asp Tyr Trp Ser Pro Gly Thr Leu Val Thr Val Ser Ser
        115                 120                 125

<210> SEQ ID NO 76
<211> LENGTH: 331
<212> TYPE: DNA
<213> ORGANISM: Artificial
<220> FEATURE:
<223> OTHER INFORMATION: SC08-059 VL DNA

<400> SEQUENCE: 76
tcctatgtgc tgactcagcc accctcagcg tctgggaccc ccgggcagag ggtcaccatc    60
tcttgttctg gaagcagctc caacatcgga actaattatg tatactggta ccagcagttc   120
ccaggaacgg ccccccaaact cctcatctat aggagttatc agcggccctc aggggtccct  180
gaccgattct ctggctccaa gtctggctcc tcagcctccc tggccatcag tgggctccag   240
tctgaggatg aggctgatta ttactgtgca acatgggatg acagcctgaa tggttgggtg   300
ttcggcggag ggaccaagct gaccgtccta g                                  331

<210> SEQ ID NO 77
<211> LENGTH: 110
<212> TYPE: PRT
<213> ORGANISM: Artificial
<220> FEATURE:
<223> OTHER INFORMATION: SC08-059 VL PROTEIN

<400> SEQUENCE: 77

Ser Tyr Val Leu Thr Gln Pro Pro Ser Ala Ser Gly Pro Gly Gln
1               5                   10                  15

Arg Val Thr Ile Ser Cys Ser Gly Ser Ser Asn Ile Gly Thr Asn
            20                  25                  30

Tyr Val Tyr Trp Tyr Gln Gln Phe Pro Gly Thr Ala Pro Lys Leu Leu
        35                  40                  45
```

Ile Tyr Arg Ser Tyr Gln Arg Pro Ser Gly Val Pro Asp Arg Phe Ser
            50                  55                  60

Gly Ser Lys Ser Gly Ser Ser Ala Ser Leu Ala Ile Ser Gly Leu Gln
 65                  70                  75                  80

Ser Glu Asp Glu Ala Asp Tyr Tyr Cys Ala Thr Trp Asp Ser Leu
                85                  90                  95

Asn Gly Trp Val Phe Gly Gly Gly Thr Lys Leu Thr Val Leu
            100                 105                 110

<210> SEQ ID NO 78
<211> LENGTH: 125
<212> TYPE: PRT
<213> ORGANISM: Artificial
<220> FEATURE:
<223> OTHER INFORMATION: CR08071 VH PROTEIN

<400> SEQUENCE: 78

Gln Val Gln Leu Val Gln Ser Gly Ala Glu Val Lys Lys Pro Gly Ala
 1               5                  10                  15

Ser Val Arg Val Ser Cys Arg Ala Ser Gly Tyr Ile Phe Thr Glu Ser
                20                  25                  30

Gly Ile Thr Trp Val Arg Gln Ala Pro Gly Gln Gly Leu Glu Trp Met
            35                  40                  45

Gly Trp Ile Ser Gly Tyr Ser Gly Asp Thr Lys Tyr Ala Gln Lys Leu
        50                  55                  60

Gln Gly Arg Val Thr Met Thr Lys Asp Thr Ser Thr Thr Thr Ala Tyr
 65                  70                  75                  80

Met Glu Leu Arg Ser Leu Arg Tyr Asp Asp Thr Ala Val Tyr Tyr Cys
                85                  90                  95

Ala Arg Asp Val Gln Tyr Ser Gly Ser Tyr Leu Gly Ala Tyr Tyr Phe
            100                 105                 110

Asp Tyr Trp Ser Pro Gly Thr Leu Val Thr Val Ser Ser
        115                 120                 125

<210> SEQ ID NO 79
<211> LENGTH: 112
<212> TYPE: PRT
<213> ORGANISM: Artificial
<220> FEATURE:
<223> OTHER INFORMATION: CR08071 VL PROTEIN

<400> SEQUENCE: 79

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Thr Asn
                20                  25                  30

Tyr Val Tyr Trp Tyr Gln Gln Phe Pro Gly Thr Ala Pro Lys Leu Leu
            35                  40                  45

Ile Tyr Arg Ser Tyr Gln Arg Pro Ser Gly Val Pro Asp Arg Phe Ser
        50                  55                  60

Gly Ser Lys Ser Gly Ser Ser Ala Ser Leu Ala Ile Ser Gly Leu Gln
 65                  70                  75                  80

Ser Glu Asp Glu Ala Asp Tyr Tyr Cys Ala Thr Trp Asp Ser Leu
                85                  90                  95

Asp Gly Trp Val Phe Gly Gly Gly Thr Lys Leu Thr Val Leu Arg Lys
            100                 105                 110

<210> SEQ ID NO 80
<211> LENGTH: 389
<212> TYPE: DNA
<213> ORGANISM: Artificial
<220> FEATURE:
<223> OTHER INFORMATION: SC10-051 VH DNA

<400> SEQUENCE: 80

| | | | | | |
|---|---|---|---|---|---|
| gaggtccagc | tggtgcagtc | tggagctgag | gtgaagaagc | ctggggcctc | agtagaactt | 60 |
| tcctgcaagg | catctggaga | caccttcacc | aactaccata | tacactgggt | gcgacaggcc | 120 |
| cctggacaag | ggcttgagtg | gatgggaata | atcaatccta | gtggtggtga | cacagactac | 180 |
| tcacagaagt | tccagggcag | agtcaccctg | accaggggaca | ggtccacaaa | cacattctat | 240 |
| atgaagttgg | ccagcctgag | atctgaggac | acggccgtgt | attactgtgc | gacagatgag | 300 |
| agtcccggac | ttttgactgg | ccttcgggat | tactggtact | actacggtat | ggacgtctgg | 360 |
| ggccagggga | ccacggtcac | cgtctcgag | | | | 389 |

<210> SEQ ID NO 81
<211> LENGTH: 129
<212> TYPE: PRT
<213> ORGANISM: Artificial
<220> FEATURE:
<223> OTHER INFORMATION: SC10-051 VH PROTEIN

<400> SEQUENCE: 81

Glu Val Gln Leu Val Gln Ser Gly Ala Glu Val Lys Lys Pro Gly Ala
1               5                   10                  15

Ser Val Glu Leu Ser Cys Lys Ala Ser Gly Asp Thr Phe Thr Asn Tyr
            20                  25                  30

His Ile His Trp Val Arg Gln Ala Pro Gly Gln Gly Leu Glu Trp Met
        35                  40                  45

Gly Ile Ile Asn Pro Ser Gly Gly Asp Thr Asp Tyr Ser Gln Lys Phe
    50                  55                  60

Gln Gly Arg Val Thr Leu Thr Arg Asp Arg Ser Thr Asn Thr Phe Tyr
65                  70                  75                  80

Met Lys Leu Ala Ser Leu Arg Ser Glu Asp Thr Ala Val Tyr Tyr Cys
                85                  90                  95

Ala Thr Asp Glu Ser Pro Gly Leu Leu Thr Gly Leu Arg Asp Tyr Trp
            100                 105                 110

Tyr Tyr Tyr Gly Met Asp Val Trp Gly Gln Gly Thr Thr Val Thr Val
        115                 120                 125

Ser

<210> SEQ ID NO 82
<211> LENGTH: 328
<212> TYPE: DNA
<213> ORGANISM: Artificial
<220> FEATURE:
<223> OTHER INFORMATION: SC10-051 VL DNA

<400> SEQUENCE: 82

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gagtgttagc | agcagctact | tagcctggta | ccagcagaaa | 120 |
| cctggccagg | ctcccaggct | cctcatctat | ggtgcatcca | gcagggccac | tggcatccca | 180 |
| gacaggttca | gtggcagtgg | gtctgggaca | gacttcactc | tcaccatcag | cagactggag | 240 |
| cctgaagatt | ttgcagtgta | ttactgtcag | cagtatggta | gctcacctct | gtgcagtttt | 300 |

```
ggccagggga ccaagctgga gatcaaac                                       328
```

<210> SEQ ID NO 83
<211> LENGTH: 109
<212> TYPE: PRT
<213> ORGANISM: Artificial
<220> FEATURE:
<223> OTHER INFORMATION: SC10-051 VL PROTEIN

<400> SEQUENCE: 83

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Cys Ser Phe Gly Gln Gly Thr Lys Leu Glu Ile Lys
            100                 105
```

<210> SEQ ID NO 84
<211> LENGTH: 368
<212> TYPE: DNA
<213> ORGANISM: Artificial
<220> FEATURE:
<223> OTHER INFORMATION: SC10-049 VH DNA

<400> SEQUENCE: 84

```
gaggtgcagc tggtggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcacgt cttagtgatg aaagtaccac atactatgca    180
gactccgtga agggccgatt cactatctcc agagacaatt ccaagaacac actgtatctg    240
cagatgaaca gcctgaaagc cgacgacacg gccatatatt actgtgcgga ggatctgggg    300
acggtgatgg actcctacta ctacggtatg aacgtctggg gcccagggac cacggtcacc    360
gtctcgag                                                            368
```

<210> SEQ ID NO 85
<211> LENGTH: 122
<212> TYPE: PRT
<213> ORGANISM: Artificial
<220> FEATURE:
<223> OTHER INFORMATION: SC10-049 VH PROTEIN

<400> SEQUENCE: 85

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Leu Ser Asp Glu Ser Thr Thr Tyr Tyr Ala Asp Ser Val Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Lys Ala Asp Asp Thr Ala Ile Tyr Tyr Cys Ala
                85                  90                  95

Glu Asp Leu Gly Thr Val Met Asp Ser Tyr Tyr Tyr Gly Met Asn Val
            100                 105                 110

Trp Gly Pro Gly Thr Thr Val Thr Val Ser
            115                 120

<210> SEQ ID NO 86
<211> LENGTH: 337
<212> TYPE: DNA
<213> ORGANISM: Artificial
<220> FEATURE:
<223> OTHER INFORMATION: SC10-049 VL DNA

<400> SEQUENCE: 86
gatgttgtga tgactcagtc tccactctcc ctgcccgtca cccctggaga gccggcctcc      60
atctcctgca ggtctagtca gagcctcctg catagtaatg gactcaatta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
ttcactttcg gcggagggac caaggtggag atcaaac                             337

<210> SEQ ID NO 87
<211> LENGTH: 112
<212> TYPE: PRT
<213> ORGANISM: Artificial
<220> FEATURE:
<223> OTHER INFORMATION: SC10-049 VH PROTEIN

<400> SEQUENCE: 87

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Leu Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Gly Gly Thr Lys Val Glu Ile Lys
            100                 105                 110

<210> SEQ ID NO 88
<211> LENGTH: 382
<212> TYPE: DNA
<213> ORGANISM: Artificial
<220> FEATURE:
<223> OTHER INFORMATION: SC10-023 VH DNA

<400> SEQUENCE: 88
gaggtgcagc tggtggagac tggggaggc ttggtacagc ctggcaggtc cctgagactc      60
tcctgtgcag cctctggatt cacctttgat gattatgcca tgcattgggt ccggcaagct    120

```
ccagggaagg gcctggagtg ggtctcaggt attaattggg ttagtactac catgggctat    180
gcggactctg tgaagggccg attcaccatc tccagagaca acgccaagaa ctccctgtat    240
ctgcaaatga acagtctgag agctgaggac acggccttgt attactgtgc aaaagatagg    300
ctggagagtg cagctataga cattctagaa gggggtactt ttgatatcag gggccaaggg    360
acaatggtca ccgtctcgag cg                                             382
```

<210> SEQ ID NO 89
<211> LENGTH: 127
<212> TYPE: PRT
<213> ORGANISM: Artificial
<220> FEATURE:
<223> OTHER INFORMATION: SC10-023 VH PROTEIN

<400> SEQUENCE: 89

```
Glu Val Gln Leu Val Glu Thr Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Val Ser Thr Thr Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Leu Glu Ser Ala Ala Ile Asp Ile Leu Glu Gly Gly
            100                 105                 110

Thr Phe Asp Ile Arg Gly Gln Gly Thr Met Val Thr Val Ser Ser
        115                 120                 125
```

<210> SEQ ID NO 90
<211> LENGTH: 331
<212> TYPE: DNA
<213> ORGANISM: Artificial
<220> FEATURE:
<223> OTHER INFORMATION: SC10-023 VL DNA

<400> SEQUENCE: 90

```
cagtctgccc tgactcagcc tccctccgcg tccggctctc tggacagtc agtcaccatc      60 tcctgcactg gaaccagcag tgatgttggt ggttataact atgtctcctg gtaccaacag    120
cacccaggca aagcccccaa actcatgatt tatgatgtca gtaagcggcc ctcagggtc     180 cctgatcgct tctctgggtc caagtctggc aacacggcct ccctgaccat ctctgggctc    240
caggctgagg acgaggctga atattactgc agctcatatg caagcggcag cacttatgtc    300
ttcggaactg ggaccaaggt caccgtccta g                                   331
```

<210> SEQ ID NO 91
<211> LENGTH: 110
<212> TYPE: PRT
<213> ORGANISM: Artificial
<220> FEATURE:
<223> OTHER INFORMATION: SC10-023 VL PROTEIN

<400> SEQUENCE: 91

```
Gln Ser Ala Leu Thr Gln Pro Pro Ser Ala Ser Gly Pro Gly Gln
1               5                   10                  15
```

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
         35                  40                  45

Met Ile Tyr Asp Val Ser Lys Arg Pro Ser Gly Val Pro Asp Arg Phe
     50                  55                  60

Ser Gly Ser Lys Ser Gly Asn Thr Ala Ser Leu Thr Ile Ser Gly Leu
65                  70                  75                  80

Gln Ala Glu Asp Glu Ala Glu Tyr Tyr Cys Ser Ser Tyr Ala Ser Gly
                 85                  90                  95

Ser Thr Tyr Val Phe Gly Thr Gly Thr Lys Val Thr Val Leu
            100                 105                 110

<210> SEQ ID NO 92
<211> LENGTH: 378
<212> TYPE: DNA
<213> ORGANISM: Artificial
<220> FEATURE:
<223> OTHER INFORMATION: SC10-032 VH DNA

<400> SEQUENCE: 92
caggtgcagc tgcaggagtc gggcccagga ctggtgaagc cttcgggcac cctgtccctc    60
acctgcaatg tctctggtgg ctccatcaac agtagtccct ataagtgggc ctggatccgc   120
cagtccccag ggaaggggct ggagtggatt gggactttct attatgatgg agcaccgac   180 tacaacccgt ccctccagag tcgactcacc atttccggag acatgtccag taaccacttc   240
tccttgaggc tgaggtctgt gaccgccgca gacacggctg tgtattactg tgcggcctat   300
tgtagtagta aagctgcca tgcctattac gactacatga acgtctgggg caaagggacc   360
acggtcaccg tctcgagc                                                 378

<210> SEQ ID NO 93
<211> LENGTH: 126
<212> TYPE: PRT
<213> ORGANISM: Artificial
<220> FEATURE:
<223> OTHER INFORMATION: SC10-032 VH PROTEIN

<400> SEQUENCE: 93

Gln Val Gln Leu Gln Glu Ser Gly Pro Gly Leu Val Lys Pro Ser Gly
1               5                   10                  15

Thr Leu Ser Leu Thr Cys Asn Val Ser Gly Gly Ser Ile Asn Ser Ser
            20                  25                  30

Pro Tyr Lys Trp Ala Trp Ile Arg Gln Ser Pro Gly Lys Gly Leu Glu
         35                  40                  45

Trp Ile Gly Thr Phe Tyr Tyr Asp Gly Ser Thr Asp Tyr Asn Pro Ser
     50                  55                  60

Leu Gln Ser Arg Leu Thr Ile Ser Gly Asp Met Ser Ser Asn His Phe
65                  70                  75                  80

Ser Leu Arg Leu Arg Ser Val Thr Ala Ala Asp Thr Ala Val Tyr Tyr
                 85                  90                  95

Cys Ala Ala Tyr Cys Ser Ser Ile Ser Cys His Ala Tyr Tyr Asp Tyr
            100                 105                 110

Met Asn Val Trp Gly Lys Gly Thr Thr Val Thr Val Ser Ser
         115                 120                 125

<210> SEQ ID NO 94
<211> LENGTH: 334

<212> TYPE: DNA
<213> ORGANISM: Artificial
<220> FEATURE:
<223> OTHER INFORMATION: SC10-032 VL DNA

<400> SEQUENCE: 94

```
gaaattgtgc tgactcagtc tccactctcc ctgcccgtca cccctggaga gccggcctcc    60
atctcctgca ggtctagtca gagcctccga catgagaatg gatacaacta tttggattgg   120
tacctgcaga agccagggca gtctccacag ctcctgatgt atttgggttc tgttcgggcc   180
tccggggtcc ctgacaggtt cagtggcagt ggatcaggca cagattttac actgaaaatc   240
agcagagtgg aggctgagga tgttggggtt tattactgca tgcaagctct acaaacgctc   300
actttcggcg gagggaccaa gctggagatc aaac                               334
```

<210> SEQ ID NO 95
<211> LENGTH: 111
<212> TYPE: PRT
<213> ORGANISM: Artificial
<220> FEATURE:
<223> OTHER INFORMATION: SC10-032 VL PROTEIN

<400> SEQUENCE: 95

```
Glu Ile Val Leu Thr Gln Ser Pro Leu Ser Leu Pro Val Thr Pro Gly
1               5                   10                  15
Glu Pro Ala Ser Ile Ser Cys Arg Ser Ser Gln Ser Leu Arg His Glu
            20                  25                  30
Asn Gly Tyr Asn Tyr Leu Asp Trp Tyr Leu Gln Lys Pro Gly Gln Ser
        35                  40                  45
Pro Gln Leu Leu Met Tyr Leu Gly Ser Val Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Leu Thr Phe Gly Gly Gly Thr Lys Leu Glu Ile Lys
            100                 105                 110
```

<210> SEQ ID NO 96
<211> LENGTH: 364
<212> TYPE: DNA
<213> ORGANISM: Artificial
<220> FEATURE:
<223> OTHER INFORMATION: SC11-024 VH DNA

<400> SEQUENCE: 96

```
gaggtgcagc tggtgcagtc tggggctgaa attaagaagc ctggggcctc agtgaaggtc    60
tcctgcaagg cttctggata cagcttcacc ggctactata tgcactgggt gcgacaggcc   120
cctggacaag acctgagtg gatggggcgg atcaaccct tcagtggtga cacaaactat   180
gcacagaggt ttcagggcag ggtcaccttg accaggggaca ggtccaccag cacagcctac   240
atggagctga gcgggctgaa atctgacgac acggccgtat atttctgtgc gagagtcgcg   300
ggtgaagatt ggttcgggga tcttgactat tggggccagg gaaccctggt caccgtctcg   360
agcg                                                                364
```

<210> SEQ ID NO 97
<211> LENGTH: 121
<212> TYPE: PRT
<213> ORGANISM: Artificial

<220> FEATURE:
<223> OTHER INFORMATION: SC11-24 VH PROTEIN

<400> SEQUENCE: 97

Glu Val Gln Leu Val Gln Ser Gly Ala Glu Ile Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Pro Glu Trp Met
        35                  40                  45

Gly Arg Ile Asn Pro Ile Ser Gly Asp Thr Asn Tyr Ala Gln Arg Phe
    50                  55                  60

Gln Gly Arg Val Thr Leu Thr Arg Asp Arg Ser Thr Ser Thr Ala Tyr
65                  70                  75                  80

Met Glu Leu Ser Gly Leu Lys Ser Asp Asp Thr Ala Val Tyr Phe Cys
                85                  90                  95

Ala Arg Val Ala Gly Glu Asp Trp Phe Gly Asp Leu Asp Tyr Trp Gly
            100                 105                 110

Gln Gly Thr Leu Val Thr Val Ser Ser
        115                 120

<210> SEQ ID NO 98
<211> LENGTH: 325
<212> TYPE: DNA
<213> ORGANISM: Artificial
<220> FEATURE:
<223> OTHER INFORMATION: SC11-024 VL  DNA

<400> SEQUENCE: 98
gaaattgtgt tgacgcagtc tccagccacc ctgtctgtgt ctccagggga aagagccacc      60
ctctcctgca gggccagtca gagtgttagc agcagctact tagcctggta ccagcagaaa     120
cctggccagg ctcccaggct cctcatcttt ggaacatcca gcagggccac tggcatccca     180
gacaggttca gtggcagtgg gtctgggaca gacttcactc tcaccatcag caggctggag     240
cctgaagatt ttgcagtgta ttactgtcag cagtatggta gctcacctcg acgttcggc      300 caagggacca aggtggagat caaac                                           325

<210> SEQ ID NO 99
<211> LENGTH: 108
<212> TYPE: PRT
<213> ORGANISM: Artificial
<220> FEATURE:
<223> OTHER INFORMATION: SC11-024 VL  PROTEIN

<400> SEQUENCE: 99

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

```
Arg Thr Phe Gly Gln Gly Thr Lys Val Glu Ile Lys
            100                 105
```

<210> SEQ ID NO 100
<211> LENGTH: 364
<212> TYPE: DNA
<213> ORGANISM: Artificial
<220> FEATURE:
<223> OTHER INFORMATION: SC11-035 VH DNA

<400> SEQUENCE: 100

```
caggtgcagc tggtacagtc tggagctgag gtgaagaagc ctgggtcctc ggtgaaggtc    60
tcctgcaaga cctctggtta cgcctttaac ggctacggta tcagctgggt gcgacaggcc   120
cctggacaag gcttgagtg gatggcatgg atcaacactt acaaagttaa cacacattat   180
gcacagaatc tccggggcag ggtcaccgtg agcatagaca catccacgac acagcctat   240 atggaactga ggagcctgag atctgacgac acggccgtct attactgtgc gagagactgg   300
ggtgggccgt ttgggaacgc ttttgatttc tggggccaag ggacaatggt caccgtctcg   360
agcg                                                                364
```

<210> SEQ ID NO 101
<211> LENGTH: 121
<212> TYPE: PRT
<213> ORGANISM: Artificial
<220> FEATURE:
<223> OTHER INFORMATION: SC11-035 VH PROTEIN

<400> SEQUENCE: 101

```
Gln Val Gln Leu Val Gln Ser Gly Ala Glu Val Lys Lys Pro Gly Ser
1               5                   10                  15

Ser Val Lys Val Ser Cys Lys Thr Ser Gly Tyr Ala Phe Asn Gly Tyr
            20                  25                  30

Gly Ile Ser Trp Val Arg Gln Ala Pro Gly Gln Gly Leu Glu Trp Val
        35                  40                  45

Ala Trp Ile Asn Thr Tyr Lys Val Asn Thr His Tyr Ala Gln Asn Leu
    50                  55                  60

Arg Gly Arg Val Thr Val Ser Ile Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Trp Gly Gly Pro Phe Gly Asn Ala Phe Asp Phe Trp Gly
            100                 105                 110

Gln Gly Thr Met Val Thr Val Ser Ser
        115                 120
```

<210> SEQ ID NO 102
<211> LENGTH: 322
<212> TYPE: DNA
<213> ORGANISM: Artificial
<220> FEATURE:
<223> OTHER INFORMATION: SC11-035 VL  DNA

<400> SEQUENCE: 102

```
gacatccaga tgacccagtc tccatcctcc ctggctgcat ctataggaga cagtgtcacc    60
atcacttgcc gggcaagtca gagcgttggc tcttacttaa attggtatca gcaaaaacca   120
gggaaagccc ctaagttgtt gatctatggt gcatccaatg tgcaaagtgg ggtcccatca   180
aggtttagtg gcagtgagtc tgggacagag tccacactca ccatcaacaa tctgcagcct   240
```

```
gaagattctg caacttacta ctgtcaacag agttacagta ccctagaac gttcggccaa      300 gggaccaagg tggaaatcaa ac                                              322
```

<210> SEQ ID NO 103
<211> LENGTH: 107
<212> TYPE: PRT
<213> ORGANISM: Artificial
<220> FEATURE:
<223> OTHER INFORMATION: SC11-035 VL PROTEIN

<400> SEQUENCE: 103

```
Asp Ile Gln Met Thr Gln Ser Pro Ser Leu Ala Ala Ser Ile Gly
1               5                   10                  15

Asp Ser Val Thr Ile Thr Cys Arg Ala Ser Gln Ser Val Gly Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Asn Val Gln Ser Gly Val Pro Ser Arg Phe Ser Gly
    50                  55                  60

Ser Glu Ser Gly Thr Glu Ser Thr Leu Thr Ile Asn Asn Leu Gln Pro
65                  70                  75                  80

Glu Asp Ser Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105
```

<210> SEQ ID NO 104
<211> LENGTH: 375
<212> TYPE: DNA
<213> ORGANISM: Artificial
<220> FEATURE:
<223> OTHER INFORMATION: SC11-036 VH DNA

<400> SEQUENCE: 104

```
gaggtgcagc tggtgcagtc tggggctgag gtgaagaagc ctggggcctc agtgacggtt      60
tcctgcaagg catctggata cgccttcacc agctactatt tacactgggt gcgacaggcc     120
cctggacaag gcttgagtg gatggggata atgaatcttc atggtggtag cacaacctac      180
gcacagaagt tccagggcag agtcaccatg accagggaca cgtccacgag acagttttac     240
atggagctga gcgcctgag atctgaggac tcggccgtat attactgtgc ccgagagagt      300
cccgatagca gtggttatcc tggctactac ggtatggacg tctggggcca ggggaccacg     360
gtcaccgtct cgagc                                                      375
```

<210> SEQ ID NO 105
<211> LENGTH: 125
<212> TYPE: PRT
<213> ORGANISM: Artificial
<220> FEATURE:
<223> OTHER INFORMATION: SC11-036 VH PROTEIN

<400> SEQUENCE: 105

```
Glu Val Gln Leu Val Gln Ser Gly Ala Glu Val Lys Lys Pro Gly Ala
1               5                   10                  15

Ser Val Thr Val Ser Cys Lys Ala Ser Gly Tyr Ala Phe Thr Ser Tyr
            20                  25                  30

Tyr Leu His Trp Val Arg Gln Ala Pro Gly Gln Gly Leu Glu Trp Met
        35                  40                  45

Gly Ile Met Asn Leu His Gly Gly Ser Thr Thr Tyr Ala Gln Lys Phe
```

```
                      50                  55                  60
Gln Gly Arg Val Thr Met Thr Arg Asp Thr Ser Thr Arg Thr Val Tyr
 65                  70                  75                  80

Met Glu Leu Ser Gly Leu Arg Ser Glu Asp Ser Ala Val Tyr Tyr Cys
                 85                  90                  95

Ala Arg Glu Ser Pro Asp Ser Ser Gly Tyr Pro Gly Tyr Tyr Gly Met
                100                 105                 110

Asp Val Trp Gly Gln Gly Thr Thr Val Thr Val Ser Ser
            115                 120                 125

<210> SEQ ID NO 106
<211> LENGTH: 325
<212> TYPE: DNA
<213> ORGANISM: Artificial
<220> FEATURE:
<223> OTHER INFORMATION: SC11-036 VL  DNA

<400> SEQUENCE: 106
gaaattgtgt tgacgcagtc tccaggcacc ctgtctttgt ctccagggga aagagccacc       60
ctctcctgca gggccagtca gagtgttagc agcgacttct tcgcctggta ccagcagaaa      120
cgtggccaga ctcccaccct cctcatctat ggtacatcca ccagggccac tggcatccca      180
gacaggttca gtggcagtgg gtctgggaca gacttcacac tcagcgtcgc cagactggag      240
cctgaagatt ttgcagtgta ttactgtcag cagtatggta gctcgacgtg gacgttcggc      300
caagggacca aggtggaaat caaac                                            325

<210> SEQ ID NO 107
<211> LENGTH: 108
<212> TYPE: PRT
<213> ORGANISM: Artificial
<220> FEATURE:
<223> OTHER INFORMATION: SC11-036 VL  PROTEIN

<400> SEQUENCE: 107

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asp
                20                  25                  30

Phe Phe Ala Trp Tyr Gln Gln Lys Arg Gly Gln Thr Pro Thr Leu Leu
            35                  40                  45

Ile Tyr Gly Thr Ser Thr Arg Ala Thr Gly Ile Pro Asp Arg Phe Ser
    50                  55                  60

Gly Ser Gly Ser Gly Thr Asp Phe Thr Leu Ser Val Ala Arg Leu Glu
 65                  70                  75                  80

Pro Glu Asp Phe Ala Val Tyr Tyr Cys Gln Gln Tyr Gly Ser Ser Thr
                85                  90                  95

Trp Thr Phe Gly Gln Gly Thr Lys Val Glu Ile Lys
            100                 105

<210> SEQ ID NO 108
<211> LENGTH: 375
<212> TYPE: DNA
<213> ORGANISM: Artificial
<220> FEATURE:
<223> OTHER INFORMATION: SC11-038 VH  DNA

<400> SEQUENCE: 108
gaggtgcagc tggtggagtc tgggggctgag gtgaagaagc ctggggcctc agtgaaggtt       60
```

```
tcctgcaagg catctggata cgccttcacc agctactatt tgcactgggt gcgacaggcc    120
cctggacaag gcttgagtg gatggggata tgaaccctc atggtggtag cacaacctac      180
gcacagaagt tccagggcag agtcaccatg accagggaca cgtccacgag cacagtctac    240
atggagctga gcagcctgag atctgaggac acggccgtgt attactgtgc ccgagagagt    300
cccgatagta gtggttatcc tggctactac ggtatggacg tctggggcca agggaccacg    360
gtcaccgtct cgagc                                                      375
```

<210> SEQ ID NO 109
<211> LENGTH: 125
<212> TYPE: PRT
<213> ORGANISM: Artificial
<220> FEATURE:
<223> OTHER INFORMATION: SC11-038 VH PROTEIN

<400> SEQUENCE: 109

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Leu His Trp Val Arg Gln Ala Pro Gly Gln Gly Leu Glu Trp Met
        35                  40                  45

Gly Ile Met Asn Pro His Gly Gly Ser Thr Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Asp Ser Ser Gly Tyr Pro Gly Tyr Tyr Gly Met
            100                 105                 110

Asp Val Trp Gly Gln Gly Thr Thr Val Thr Val Ser Ser
        115                 120                 125
```

<210> SEQ ID NO 110
<211> LENGTH: 331
<212> TYPE: DNA
<213> ORGANISM: Artificial
<220> FEATURE:
<223> OTHER INFORMATION: SC11-038 VL  DNA

<400> SEQUENCE: 110

```
tcctatgagc tgactcagcc accctcagcg tctgggaccc ccgggcagag ggtcaccatg     60
tcttgttctg gaagcagatc caacatcgga tctaatcctg taagctggtt ccagcaactc    120
ccgggaatgg tccccaaact cctcatctat actaatgatc agcggccctc aggggtccct    180
gaccgattct ctggctccaa gtctggcccc tcagcctccc tggccatcag tgggctccag    240
tctgaggatg aggctgatta ttactgtgca gcatgggatg acagcctgaa aggttgggtg    300
ttcggcggag ggaccaagct gaccgtccta g                                    331
```

<210> SEQ ID NO 111
<211> LENGTH: 110
<212> TYPE: PRT
<213> ORGANISM: Artificial
<220> FEATURE:
<223> OTHER INFORMATION: SC11-038 VL  PROTEIN

<400> SEQUENCE: 111

Ser Tyr Glu Leu Thr Gln Pro Pro Ser Ala Ser Gly Thr Pro Gly Gln

```
1               5                  10                 15
Arg Val Thr Met Ser Cys Ser Gly Ser Arg Ser Asn Ile Gly Ser Asn
                20                 25                 30

Pro Val Ser Trp Phe Gln Gln Leu Pro Gly Met Val Pro Lys Leu Leu
                35                 40                 45

Ile Tyr Thr Asn Asp Gln Arg Pro Ser Gly Val Pro Asp Arg Phe Ser
        50                 55                 60

Gly Ser Lys Ser Gly Pro Ser Ala Ser Leu Ala Ile Ser Gly Leu Gln
65                  70                 75                 80

Ser Glu Asp Glu Ala Asp Tyr Tyr Cys Ala Ala Trp Asp Asp Ser Leu
                85                 90                 95

Lys Gly Trp Val Phe Gly Gly Gly Thr Lys Leu Thr Val Leu
                100                105                110

<210> SEQ ID NO 112
<211> LENGTH: 364
<212> TYPE: DNA
<213> ORGANISM: Artificial
<220> FEATURE:
<223> OTHER INFORMATION: SC11-039 VH DNA

<400> SEQUENCE: 112
gaggtccagc tggtacagtc tggagcagag gtgaaaaagc ccggggagtc tgtgaagatc        60
tcctgtaaga cttctggtta cgcctttacc ggctacggta tcagctgggt gcgacaggcc       120
cctggacaag gccttgagtg gatgggatgg atcaacactt acaaatttaa cacaaattat       180
gcacagaacc tgcagggcag agtcaccatg accatagaca catccacgag cgcagcctac       240
atggagctga ggagcctgag atatgaggac acggccgtat atttctgtgc gagagactgg       300
gctgggccgt ttgggaatgc ttttgatgtc tggggccagg ggacaatggt caccgtctcg       360
agcg                                                                    364

<210> SEQ ID NO 113
<211> LENGTH: 121
<212> TYPE: PRT
<213> ORGANISM: Artificial
<220> FEATURE:
<223> OTHER INFORMATION: SC11-039 VH PROTEIN

<400> SEQUENCE: 113

Glu Val Gln Leu Val Gln Ser Gly Ala Glu Val Lys Lys Pro Gly Glu
1               5                  10                 15

Ser Val Lys Ile Ser Cys Lys Thr Ser Gly Tyr Ala Phe Thr Gly Tyr
                20                 25                 30

Gly Ile Ser Trp Val Arg Gln Ala Pro Gly Gln Gly Leu Glu Trp Met
                35                 40                 45

Gly Trp Ile Asn Thr Tyr Lys Phe Asn Thr Asn Tyr Ala Gln Asn Leu
        50                 55                 60

Gln Gly Arg Val Thr Met Thr Ile Asp Thr Ser Thr Ser Ala Ala Tyr
65                  70                 75                 80

Met Glu Leu Arg Ser Leu Arg Tyr Glu Asp Thr Ala Val Tyr Phe Cys
                85                 90                 95

Ala Arg Asp Trp Ala Gly Pro Phe Gly Asn Ala Phe Asp Val Trp Gly
                100                105                110

Gln Gly Thr Met Val Thr Val Ser Ser
        115                 120
```

<210> SEQ ID NO 114
<211> LENGTH: 321
<212> TYPE: DNA
<213> ORGANISM: Artificial
<220> FEATURE:
<223> OTHER INFORMATION: SC11-039 VL DNA

<400> SEQUENCE: 114

```
acatccagat gacccagtct ccatcttccc tgtctgcatc tataggagac agagtcgcca      60
tcacttgcca ggcgagtcag gacattagcg actatttaaa ttggtatcag caacaaccag     120
ggaaagcccc taagctcctg ctctacggtg catccaattt ggaaacaggg gtcccatcaa     180
ggttcagtgg aagtggatct gggacagatt ttactttcac catcagcagc ctgcagcctg     240
aagacattgc aacatattat tgtcaacagt atggtaatct ccctccgact ttcggcgggg     300
ggaccaagct ggagatcaaa c                                                321
```

<210> SEQ ID NO 115
<211> LENGTH: 106
<212> TYPE: PRT
<213> ORGANISM: Artificial
<220> FEATURE:
<223> OTHER INFORMATION: SC11-039 VL PROTEIN

<400> SEQUENCE: 115

Ile Gln Met Thr Gln Ser Pro Ser Ser Leu Ser Ala Ser Ile Gly Asp
1               5                   10                  15

Arg Val Ala Ile Thr Cys Gln Ala Ser Gln Asp Ile Ser Asp Tyr Leu
            20                  25                  30

Asn Trp Tyr Gln Gln Pro Gly Lys Ala Pro Lys Leu Leu Leu Tyr
        35                  40                  45

Gly Ala Ser Asn Leu Glu Thr Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Tyr Gly Asn Leu Pro Pro Thr
                85                  90                  95

Phe Gly Gly Gly Thr Lys Leu Glu Ile Lys
            100                 105

<210> SEQ ID NO 116
<211> LENGTH: 121
<212> TYPE: PRT
<213> ORGANISM: Artificial
<220> FEATURE:
<223> OTHER INFORMATION: SC09-114 VH PROTEIN

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

```
Ala Arg His Gly Asn Tyr Tyr Tyr Ser Gly Met Asp Val Trp Gly
            100                 105                 110
Gln Gly Thr Thr Val Thr Val Ser Ser
        115                 120

<210> SEQ ID NO 117
<211> LENGTH: 110
<212> TYPE: PRT
<213> ORGANISM: Artificial
<220> FEATURE:
<223> OTHER INFORMATION: SC09-114 VL PROTEIN

<400> SEQUENCE: 117

Ser Tyr Val Leu Thr Gln Pro Pro Ala Val Ser Gly Thr Pro Gly Gln
1               5                   10                  15
Arg Val Thr Ile Ser Cys Ser Gly Ser Asp Ser Asn Ile Gly Arg Arg
            20                  25                  30
Ser Val Asn Trp Tyr Gln Gln Phe Pro Gly Thr Ala Pro Lys Leu Leu
        35                  40                  45
Ile Tyr Ser Asn Asp Gln Arg Pro Ser Val Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Glu Tyr Tyr Cys Ala Ala Trp Asp Asp Ser Leu
                85                  90                  95
Lys Gly Ala Val Phe Gly Gly Gly Thr Gln Leu Thr Val Leu
            100                 105                 110

<210> SEQ ID NO 118
<211> LENGTH: 372
<212> TYPE: DNA
<213> ORGANISM: Artificial
<220> FEATURE:
<223> OTHER INFORMATION: SC08-031 VH DNA

<400> SEQUENCE: 118
gaggtgcagc tggtggagtc tgggggaggc ctggtacagc ctggcaggtc cctgagactc      60
tcctgtgcag cctctggatt cacctttgat gagtatatca tgcattgggt ccggcaagct     120
cccgggaagg gccgaatg gtcgcaggt attaattgga aggtaattt catgggttat        180 gcggactctg tccagggccg attcaccatc tccagagaca acgccaagaa ctccctctat     240
ctgcaaatga acagtctgag agctgacgac acggccttat attactgtgc aaaagaccgg     300
ctggagagtt cagctatgga cattctagaa gggggtactt ttgatatctg gggccaaggg     360
acaatggtca cc                                                         372

<210> SEQ ID NO 119
<211> LENGTH: 124
<212> TYPE: PRT
<213> ORGANISM: Artificial
<220> FEATURE:
<223> OTHER INFORMATION: SC08-031 VH PROTEIN

<400> SEQUENCE: 119

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Glu Tyr
            20                  25                  30
Ile Met His Trp Val Arg Gln Ala Pro Gly Lys Gly Pro Glu Trp Val
```

```
                35                  40                  45
Ala Gly Ile Asn Trp Lys Gly Asn Phe Met Gly Tyr Ala Asp Ser Val
         50                  55                  60
Gln Gly Arg Phe Thr Ile Ser Arg Asp Asn Ala Lys Asn Ser Leu Tyr
 65                  70                  75                  80
Leu Gln Met Asn Ser Leu Arg Ala Asp Asp Thr Ala Leu Tyr Tyr Cys
                 85                  90                  95
Ala Lys Asp Arg Leu Glu Ser Ser Ala Met Asp Ile Leu Glu Gly Gly
                100                 105                 110
Thr Phe Asp Ile Trp Gly Gln Gly Thr Met Val Thr
            115                 120
```

```
<210> SEQ ID NO 120
<211> LENGTH: 331
<212> TYPE: DNA
<213> ORGANISM: Artificial
<220> FEATURE:
<223> OTHER INFORMATION: SC08-031 VL DNA

<400> SEQUENCE: 120
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca agcccccaa actcatgatt tatgatgtca gtagtcggcc ctcaggggtt      180
tctaatcgct tctctggctc caagtctggc gacacggcct ccctgagcat ctctgggctc     240
caggctgagg acgaggctga ttattactgc agctcatata caagcagcag cactcatgtc     300
ttcggaactg ggaccaaggt caccgtccta g                                    331
```

```
<210> SEQ ID NO 121
<211> LENGTH: 110
<212> TYPE: PRT
<213> ORGANISM: Artificial
<220> FEATURE:
<223> OTHER INFORMATION: SC08-031 VL PROTEIN

<400> SEQUENCE: 121

Gln Ser Ala Leu Thr Gln Pro Ala Ser Val Ser Gly Ser Pro Gly Gln
  1               5                  10                  15
Ser Ile Thr Ile Ser Cys Thr Gly Thr Ser Ser Asp Val Gly Gly Tyr
             20                  25                  30
Asn Tyr Val Ser Trp Tyr Gln Gln His Pro Gly Lys Ala Pro Lys Leu
         35                  40                  45
Met Ile Tyr Asp Val Ser Ser Arg Pro Ser Gly Val Ser Asn Arg Phe
     50                  55                  60
Ser Gly Ser Lys Ser Gly Asp Thr Ala Ser Leu Ser Ile Ser Gly Leu
 65                  70                  75                  80
Gln Ala Glu Asp Glu Ala Asp Tyr Tyr Cys Ser Ser Tyr Thr Ser Ser
                 85                  90                  95
Ser Thr His Val Phe Gly Thr Gly Thr Lys Val Thr Val Leu
            100                 105                 110
```

```
<210> SEQ ID NO 122
<211> LENGTH: 381
<212> TYPE: DNA
<213> ORGANISM: Artificial
<220> FEATURE:
<223> OTHER INFORMATION: SC08-032 VH DNA

<400> SEQUENCE: 122
```

```
gaggtgcagc tggtggagtc tgggggaggc tggtacagc ctggcaggtc cctgagactg      60
tcctgtgcag cctctggatt cagctttgat gagtacatca tgcattgggt ccggcaagct    120
ccagggaagg gcctggagtg ggtcgcaggt attaattgga aaggtaattt catgggttat    180
gcggactctg tccagggccg attcaccatc tccagagaca cggcaagaa ctccctctat    240 ctgcaaatga acagtctgag agctgaggac acggccttgt attactgtgc aaaagaccgg    300
ctggagagtt cagctatgga cattctagaa gggggtactt ttgatatctg gggccaaggg    360
acaatggtca ccgtctcgag c                                              381
```

<210> SEQ ID NO 123
<211> LENGTH: 127
<212> TYPE: PRT
<213> ORGANISM: Artificial
<220> FEATURE:
<223> OTHER INFORMATION: SC08-032 VH PROTEIN

<400> SEQUENCE: 123

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Asp Glu Tyr
            20                  25                  30

Ile Met His Trp Val Arg Gln Ala Pro Gly Lys Gly Leu Glu Trp Val
        35                  40                  45

Ala Gly Ile Asn Trp Lys Gly Asn Phe Met Gly Tyr Ala Asp Ser Val
    50                  55                  60

Gln Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Leu Glu Ser Ser Ala Met Asp Ile Leu Glu Gly Gly
            100                 105                 110

Thr Phe Asp Ile Trp Gly Gln Gly Thr Met Val Thr Val Ser Ser
        115                 120                 125
```

<210> SEQ ID NO 124
<211> LENGTH: 331
<212> TYPE: DNA
<213> ORGANISM: Artificial
<220> FEATURE:
<223> OTHER INFORMATION: SC08-032 VL DNA

<400> SEQUENCE: 124

```
cagtctgccc tgactcagcc tgcctccgtg tctgggtctc ctggacagtc gatcaccatc      60
tcctgcactg gaacccgcag ggacgttggt gattataagt atgtctcctg gtaccaacaa    120
cacccaggca aagcccccaa actcatgatt tatgatgtca gtaatcggcc ctcaggggtc    180
tctaatcgct tctctggctc caagtctggc accacggcct ccctgaccat ctctgggctc    240
caggctgagg acgaggctga ttattattgc agttcataca caaccagcaa cactcgggtg    300
ttcggcggag ggaccaagct gaccgtccta g                                    331
```

<210> SEQ ID NO 125
<211> LENGTH: 110
<212> TYPE: PRT
<213> ORGANISM: Artificial
<220> FEATURE:
<223> OTHER INFORMATION: SC08-032 VL PROTEIN

<400> SEQUENCE: 125

Gln Ser Ala Leu Thr Gln Pro Ala Ser Val Ser Gly Ser Pro Gly Gln
1               5                   10                  15

Ser Ile Thr Ile Ser Cys Thr Gly Thr Arg Arg Asp Val Gly Asp Tyr
            20                  25                  30

Lys Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Thr Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Asn Thr Arg Val Phe Gly Gly Gly Thr Lys Leu Thr Val Leu
            100                 105                 110

<210> SEQ ID NO 126
<211> LENGTH: 381
<212> TYPE: DNA
<213> ORGANISM: Artificial
<220> FEATURE:
<223> OTHER INFORMATION: SC08-034 VH DNA

<400> SEQUENCE: 126
gaggtgcagc tggtggagac tgggggaggc ctggtacagc ctggcaggtc cctgagactc      60
tcctgtgcag cctctggatt cacctttgat gagtatatca tgcattgggt ccggcaagct    120
cccgggaagg gcccggaatg ggtcgcaggt attaattgga aaggtaattt catgggttat    180
gcggactctg tccagggccg attcaccatc tccagagaca cgccaagaa ctccctctat     240 ctgcaaatga acagtctgag agctgacgac acggcctat attactgtgc aaaagaccgg    300
ctggagagtt cagctatgga cattctagaa gggggtactt ttgatatctg gggccaaggg    360
acaatggtca ccgtctcgag c                                              381

<210> SEQ ID NO 127
<211> LENGTH: 127
<212> TYPE: PRT
<213> ORGANISM: Artificial
<220> FEATURE:
<223> OTHER INFORMATION: SC08-034 VH PROTEIN

<400> SEQUENCE: 127

Glu Val Gln Leu Val Glu Thr Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Ile Met His Trp Val Arg Gln Ala Pro Gly Lys Gly Pro Glu Trp Val
        35                  40                  45

Ala Gly Ile Asn Trp Lys Gly Asn Phe Met Gly Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Leu Tyr Tyr Cys
                85                  90                  95

Ala Lys Asp Arg Leu Glu Ser Ser Ala Met Asp Ile Leu Glu Gly Gly
            100                 105                 110

Thr Phe Asp Ile Trp Gly Gln Gly Thr Met Val Thr Val Ser Ser

<210> SEQ ID NO 128
<211> LENGTH: 322
<212> TYPE: DNA
<213> ORGANISM: Artificial
<220> FEATURE:
<223> OTHER INFORMATION: SC08-034 VL DNA

<400> SEQUENCE: 128

```
gacatccaga tgacccagtc tccatcctcc ctgtctgcat ctgtgggaga cagagtcacc    60
atcacttgcc gggcaagtca gggcattaga aatgatttag ctggtatca gcagaaacca    120
gggaaagccc ctaagcgcct gatctatgct gcatccagtt tgcaaagtgg ggtcccatca   180
aggttcagtg gcagtggatc tgggacagat ttcactctca ccatcagcag tctgcaacct   240
gaagattttg caacttacta ttgtcaacag gctaacactt atccactcac tttcggcgga   300
gggaccaagc tggagatcaa ac                                            322
```

<210> SEQ ID NO 129
<211> LENGTH: 107
<212> TYPE: PRT
<213> ORGANISM: Artificial
<220> FEATURE:
<223> OTHER INFORMATION: SC08-034 VL PROTEIN

<400> SEQUENCE: 129

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Thr Tyr Pro Leu
                85                  90                  95

Thr Phe Gly Gly Gly Thr Lys Leu Glu Ile Lys
            100                 105
```

<210> SEQ ID NO 130
<211> LENGTH: 381
<212> TYPE: DNA
<213> ORGANISM: Artificial
<220> FEATURE:
<223> OTHER INFORMATION: SC08-035 VH DNA

<400> SEQUENCE: 130

```
gaggtgcagc tggtggagtc tgggggaggc ctggtacagc ctggcaggtc cctgagactc    60
tcctgtgcag cctctggatt cacctttgat gagtatatca tgcattgggt ccggcaagct   120
cccgggaagg gcccggaatg ggtcgcaggt attaattgga aagtaattt catgggttat   180
gcggactctg tccagggccg attcaccatc tccagagaca cgccaagaa ctccctctat   240
ctgcaaatga acagtctgag agctgacgac acggcttat attactgtgc aaaagaccgg   300
ctggagagtt cagctatgga cattctagaa gggggtactt ttgatatctg ggccaaggg   360
acaatggtca ccgtctcgag c                                            381
```

```
<210> SEQ ID NO 131
<211> LENGTH: 127
<212> TYPE: PRT
<213> ORGANISM: Artificial
<220> FEATURE:
<223> OTHER INFORMATION: SC08-035 VH PROTEIN

<400> SEQUENCE: 131

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Ile Met His Trp Val Arg Gln Ala Pro Gly Lys Gly Pro Glu Trp Val
        35                  40                  45

Ala Gly Ile Asn Trp Lys Gly Asn Phe Met Gly Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Leu Tyr Tyr Cys
                85                  90                  95

Ala Lys Asp Arg Leu Glu Ser Ser Ala Met Asp Ile Leu Glu Gly Gly
            100                 105                 110

Thr Phe Asp Ile Trp Gly Gln Gly Thr Met Val Thr Val Ser Ser
        115                 120                 125

<210> SEQ ID NO 132
<211> LENGTH: 325
<212> TYPE: DNA
<213> ORGANISM: Artificial
<220> FEATURE:
<223> OTHER INFORMATION: SC08-035 VL DNA

<400> SEQUENCE: 132
tcttctgagc tgactcagga ccctgctgtg tctgtggcct tgggacagac agtcaggatc      60
acatgccaag agacagcct cagaagctat tatgcaagct ggtaccagca gaagccagga     120
caggcccctg tacttgtcat ctatggtaaa acaaccggc cctcagggat cccagaccga     180
ttctctggct ccagctcaag aaacacagct tccttgacca tcactggggc tcaggcggaa    240
gatgaggctg actattattg tgactcccgg gacagcagtg gaacccatta tgtcttcgga    300
ggtgggacca aggtcaccgt cctag                                          325

<210> SEQ ID NO 133
<211> LENGTH: 108
<212> TYPE: PRT
<213> ORGANISM: Artificial
<220> FEATURE:
<223> OTHER INFORMATION: SC08-035 VL PROTEIN

<400> SEQUENCE: 133

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Arg Asn Thr Ala Ser Leu Thr Ile Thr Gly Ala Gln Ala Glu
```

-continued

```
              65                  70                  75                  80
Asp Glu Ala Asp Tyr Tyr Cys Asp Ser Arg Asp Ser Ser Gly Thr His
                        85                  90                  95

Tyr Val Phe Gly Gly Gly Thr Lys Val Thr Val Leu
                100                 105
```